(12) United States Patent
Hubschwerlen et al.

(10) Patent No.: US 9,079,922 B2
(45) Date of Patent: Jul. 14, 2015

(54) 2-OXO-OXAZOLIDIN-3,5-DIYL ANTIBIOTIC DERIVATIVES

(71) Applicant: Actelion Pharmaceuticals Ltd., Allschwil (CH)

(72) Inventors: Christian Hubschwerlen, Durmenach (FR); Georg Rueedi, Allschwil (CH); Jean-Philippe Surivet, Kembs (FR); Cornelia Zumbrunn Acklin, Basel (CH)

(73) Assignee: Actelion Pharmaceuticals Ltd, Allschwil (CH)

( * ) Notice: Subject to any disclaimer, the term of this patent is extended or adjusted under 35 U.S.C. 154(b) by 0 days.

(21) Appl. No.: 14/356,896

(22) PCT Filed: Nov. 7, 2012

(86) PCT No.: PCT/IB2012/056236
§ 371 (c)(1),
(2) Date: May 8, 2014

(87) PCT Pub. No.: WO2013/068948
PCT Pub. Date: May 16, 2013

(65) Prior Publication Data
US 2015/0051188 A1 Feb. 19, 2015

(30) Foreign Application Priority Data

Nov. 8, 2011 (WO) .................. PCT/IB2011/054968

(51) Int. Cl.
| C07D 513/04 | (2006.01) |
| C07D 413/14 | (2006.01) |
| C07D 417/14 | (2006.01) |
| C07D 498/04 | (2006.01) |

(52) U.S. Cl.
CPC ............ C07D 513/04 (2013.01); C07D 413/14 (2013.01); C07D 417/14 (2013.01); C07D 498/04 (2013.01)

(58) Field of Classification Search
None
See application file for complete search history.

(56) References Cited

U.S. PATENT DOCUMENTS

| 8,217,029 B2 | 7/2012 | Bur et al. |
| 8,618,092 B2 | 12/2013 | Hubschwerlen et al. |
| 2007/0060558 A1 | 3/2007 | Sanchez et al. |

FOREIGN PATENT DOCUMENTS

| CN | 101792443 | 8/2010 |
| DE | 2362553 | 12/1973 |
| DE | 2840910 | 9/1978 |
| EP | 0132845 | 2/1985 |
| EP | 0235762 | 9/1987 |
| EP | 0241206 | 10/1987 |
| EP | 0607825 | 7/1994 |
| GB | 1426070 | 2/1976 |
| GB | 1598915 | 9/1981 |
| JP | 01165584 | 6/1989 |
| WO | 2004/002973 | 1/2004 |
| WO | 2006/024741 | 3/2006 |
| WO | 2007/118130 | 10/2007 |
| WO | 2008/126034 | 10/2008 |

(Continued)

OTHER PUBLICATIONS

Chang et al., "Triazolinones as Nonpeptide Angiotensin II Antagonists. 1. Synthesis and Evaluation of Potent 2,4,5-Trisubstituted Triazolinones," J. Med. Chem. (1993), vol. 36, pp. 2558-2568.

Chen et al., "1,1,1-Tris(hydroxymethyl)ethane as a New, Efficient, and Versatile Tripod Ligand for Copper-Catalyzed Cross-Coupling Reactions of Aryl Iodides with Amides, Thiols, and Phenols," Org. Lett. (2006), vol. 8, No. 24, pp. 5609-5612.

Chu et al., "Practical Synthesis of Iminochlorothioformates: Application of Iminochlorothioformates in the Synthesis of Novel 2,3,4,9-Tetrahydroisothiazolo[5,4-b][1,8]naphthyridine-3,4-diones and 2,3,49-tetrahydroisothiazolo[5,4-b] quinoline-3,4-dione Derivatives," J. Hetorocyclic Chem. (1990), vol. 27, pp. 1191-1195.

Gibson, Mark, Pharmaceutical Preformulation and Formulation: A Practical Guide from Candidate Drug Selection to Commercial Dosage Form (1st Edition, 2001) (7 pages, TOC).

(Continued)

Primary Examiner — Timothy R Rozof
(74) Attorney, Agent, or Firm — Hunton & Williams LLP

(57) ABSTRACT

The invention relates to antibacterial compounds of formula I

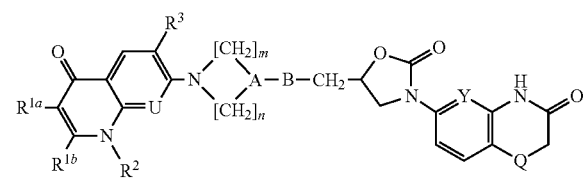

wherein
$R^{1a}$ represents H or carboxy and $R^{1b}$ represents H, or $R^{1a}$ and $R^{1b}$ represent together either the group *—C(O)—NH—S—# or the group *—C(OH)=N—S—# wherein "*" represents the point of attachment of $R^{1a}$ and "#" represents the point of attachment of $R^{1b}$;
$R^2$ represents H, $(C_1-C_3)$alkyl, hydroxy-$(C_1-C_3)$alkyl, benzyl or $(C_3-C_5)$cycloalkyl;
$R^3$ represents H or halogen;
U represents N or $CR^4$; wherein $R^4$ is H or $(C_1-C_3)$alkoxy;
A represents CH, B represents NH and m represents 1 or 2 and n represents 1 or 2; or A represents N, B is absent, m represents 2 and n represents 2;
Y represents CH or N; and
Q represents O or S;
and salts of such compounds.

16 Claims, No Drawings

(56) References Cited

FOREIGN PATENT DOCUMENTS

| WO | 2010/041194 | 4/2010 |
|---|---|---|
| WO | 2010/041218 | 4/2010 |
| WO | 2010/056633 | 5/2010 |
| WO | 2011/037433 | 3/2011 |

OTHER PUBLICATIONS

Gould, Philip, "Salt selection for basic drugs," International Journal of Pharmaceuticals (1986), vol. 33, pp. 201-217.

Greene, T. W. et al., "Protection for the Amino Group," in Protecting Groups in Organic Synthesis (3rd Edition,1999), pp. 494-653.

Greene, T. W. et al., "Protection for the Amino Group," in Protecting Groups in Organic Synthesis (3rd Edition,1999), pp. 564-566.

Greene, T. W. et al., "Protection for the Amino Group," in Protecting Groups in Organic Synthesis (3rd Edition,1999), (TOC + Index).

Hubschwerlen, C. et al, "Structure-Activity Relationship in the Oxazolidinone-Quinolone Hybrid Series: Influence of the Central Spacer on the Antibacterial Activity and the Mode of Action," Bioorganic & Medicinal Chemistry Letters (2002), vol. 13, No. 23, pp. 4229-4233.

Larock, R.C., Comprehensive Organic Transformations, A Guide to Functional Group Preparations (2nd Edition, 1999), p. 779.

Clinical & Lab Standards Institute, "Methods for Dilution Antimicrobial Susceptibility Tests for Bacteria that Grow Aerobically" (2006), vol. 26, No. 2.

Nishimura Y. et al., "Pyridonecarboxylic Acids as Antibacterial Agents XII. Synthesis and Antibacterial Activity of Enoxacin Analogues with a Variant at Position 1," Chemical & Pharmaceutical Bulletin (1988), vol. 36, No. 3, pp. 1223-1228.

Gennaro, Alfonso, Remington: The Science and Practice of Pharmacy (21st Edition, 2005) (3 pages, TOC).

Sato et al., "One-pot reductive amination of aldehydes and ketones with -picoline-borane in methanol, in water, and in neat conditions", Tetrahedron (2004), vol. 60, pp. 7899-7906.

Thompson, A. et al., "Direct Conversion of Activated Alcohols to Azides Using Diphenyl Phosphorazidate. A Practical Alternative to Mitsunobu Conditions," J. Org. Chem. (1993), vol. 58, pp. 5886-5888.

2-OXO-OXAZOLIDIN-3,5-DIYL ANTIBIOTIC DERIVATIVES

CROSS-REFERENCE TO RELATED APPLICATIONS

This application is the U.S. National Phase of International Patent Application No. PCT/IB2012/056236, filed Nov. 7, 2012, which claims priority to International Patent Application No. PCT/IB2011/054968, filed Nov. 8, 2011, the contents of each are hereby incorporated by reference in their entireties.

The present invention concerns 2-oxo-oxazolidin-3,5-diyl antibiotic derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram-positive and Gram-negative aerobic and anaerobic bacteria and mycobacteria.

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immune-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- *Enterobacteriacea* are cephalosporin and quinolone resistant;
- *P. aeruginosa* are β-lactam and quinolone resistant.

Furthermore, the incidence of multi-drug-resistant Gram-negative strains such as *Enterobacteriacae* and *Pseudomonas aeruginosa*, is steadily increasing and new emerging organisms like *Acinetobacter* spp. or *Clostridium difficile*, which have been selected during therapy with the currently used antibiotics, are becoming a real problem in hospital settings. Therefore, there is a high medical need for new antibacterial agents which overcome these multidrug-resistant bacilli.

In addition, microorganisms that are causing persistent infections are increasingly being recognized as causative agents or cofactors of severe chronic diseases like peptic ulcers or heart diseases.

WO 2006/024171 and US 2007/0060558 describe antibacterial compounds of formula (A1)

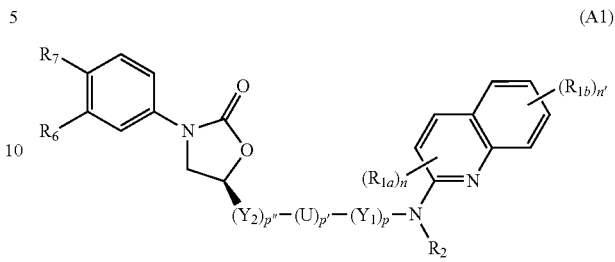

wherein
n and n' each independently represent 0, 1, 2 or 3;
$R_{1a}$ and $R_{1b}$ can (notably) each independently represent halogen, $(C_1$-$C_6)$alkyl or $(C_1$-$C_6)$alkoxy;
$R_2$ can notably represent H and the group —$(Y_1)_p$—$(U)_{p'}$—$(Y_2)_{p''}$— can notably represent 2-ethylamino, 2-propylamino or 3-propylamino, or also $R_2$ can form a cyclic structure with $Y_1$, U or $Y_2$;
$R_6$ and $R_7$ can (among other possibilities) form together a cyclic structure.

Besides, WO 2008/126034 describes antibacterial compounds of formula (A2)

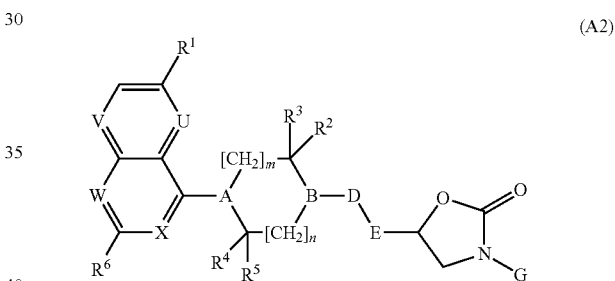

wherein
$R^1$ represents hydrogen, alkoxy, halogen or cyano;
one or two of U, V, W, and X represent(s) N and the remaining each represent CH, or, in the case of X, represent $CR^a$, $R^a$ representing H or halogen;
each of $R^2$, $R^3$, $R^4$ and $R^5$ can notably represent H;
$R^6$ represents H or $(C_1$-$C_4)$alkyl;
A, B, m, n, D and E can notably have the following respective meanings:
- A represents N, B represents N, D represents a bond, E represents $CH_2$ or *—$COCH_2$— wherein the asterisk indicates the bond which is attached to B, and m and n each represent 1; or
- A represents N, B represents C(OH), D represents a bond, E represents $CH_2$, and m and n each represent 1; or
- A represents N, B represents CH, D represents $NR^b$, E represents $CH_2$, $R^b$ represents H or $(C_1$-$C_4)$alkyl, and m and n each represent 1; or
- A represents N, B represents CH, D represents NH, E represents $CH_2$, m represents the integer 2, and n represents 0; or
- A represents N, B represents CH, D represents $NR^c$, E represents $CH_2$, CO or $CH_2CH_2$, $R^c$ represents H or $(C_1$-$C_4)$alkyl, m represents 1, and n represents 0; or
- A represents N, B represents CH, D represents *—CH($R^d$)—N($R^e$)— wherein the asterisk indicates the bond which is attached to B, E represents $CH_2$ or CO, $R^d$ represents H, $R^e$ represents H or $(C_1-C_4)$alkyl, m represents 1, and n represents 0; or A represents N, B represents CH, D represents *—CONH— wherein the asterisk indicates the bond which is attached to B, E represents $CH_2$, m represents 1, and n represents 0; or A represents N, B represents C(OH), D represents *—$CH_2$—NH— wherein the asterisk indicates the bond which is attached to B, E represents $CH_2$, m represents 1, and n represents 0; or A represents N, B represents CH, D represents *—CO—NH— wherein the asterisk indicates the bond which is attached to B, E represents $CH_2$, and m and n each represent 0; or A represents N, B represents CH, D represents *—$CH_2$—N($R^f$)— wherein the asterisk indicates the bond which is attached to B, E represents $CH_2$, $CH_2CH_2$ or CO, $R^f$ represents H or $(C_1-C_4)$alkyl, and m and n each represent 0; or A represents N, B represents CH, D represents $NR^g$, E represents $CH_2$, $CH_2CH_2$, CO or *—$COCH_2$— wherein the asterisk indicates the bond which is attached to B, $R^g$ represents H, $(C_1-C_4)$alkyl or $(C_2-C_4)$alkyl which is mono- or di-substituted with hydroxy, and m and n each represent 0;

G may notably represent a group

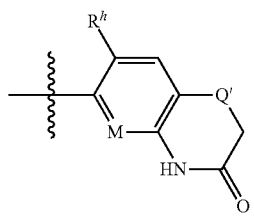

wherein $R^h$ represents H or fluorine, M represents CH or N and Q' represents O or S.

The instant invention provides further antibacterial compounds comprising a 2-oxo-oxazolidin-3,5-diyl motif, i.e. the compounds of formula I described herein.

Various embodiments of the invention are presented hereafter:

1) The invention relates to the compounds of formula I

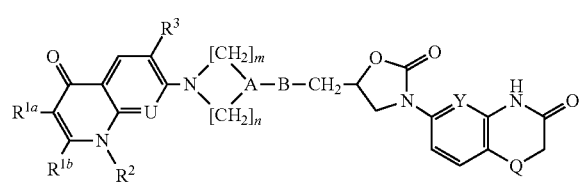

wherein
$R^{1a}$ represents H or carboxy and $R^{1b}$ represents H, or $R^{1a}$ and $R^{1b}$ represent together either the group *—C(O)—NH—S—# or the group *—C(OH)=N—S—# wherein "*" represents the point of attachment of $R^{1a}$ and "#" represents the point of attachment of $R^{1b}$;
$R^2$ represents H, $(C_1-C_3)$alkyl, hydroxy-$(C_1-C_3)$alkyl, benzyl or $(C_3-C_5)$cycloalkyl;
$R^3$ represents H or halogen (especially fluorine);

U represents N or $CR^4$, wherein $R^4$ is H or $(C_1-C_3)$alkoxy;
A represents CH, B represents NH, m represents 1 or 2 and n represents 1 or 2; or A represents N, B is absent (i.e. A is directly bound to the $CH_2$ group), m represents 2 and n represents 2;
Y represents CH or N; and
Q represents O or S.

2) The invention notably relates to the compounds of formula I according to embodiment 1) which are also compounds of formula $I_{E1}$

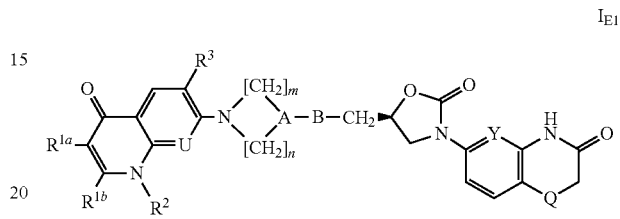

wherein the absolute configuration of the oxazolidinone moiety is as depicted in formula $I_{E1}$ [i.e. the absolute configuration of the oxazolidinone moiety is (R)].

3) The invention also notably relates to the compounds of formula I according to embodiment 1) which are also compounds of formula $I_{E2}$

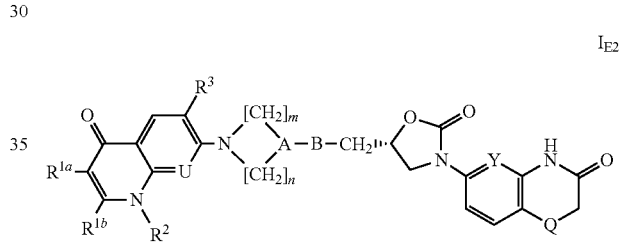

wherein the absolute configuration of the oxazolidinone moiety is as depicted in formula $I_{E2}$ [i.e. the absolute configuration of the oxazolidinone moiety is (S)].

4) The invention in particular relates to the compounds of formula I according to embodiment 1) which are also compounds of formula $I_P$

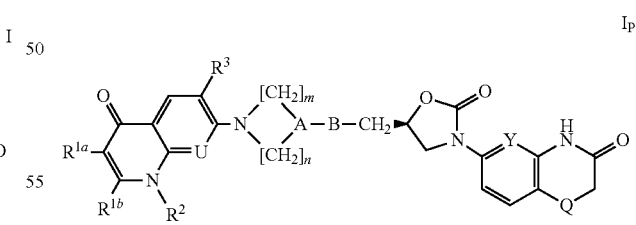

wherein
$R^{1a}$ represents H or carboxy;
$R^{1b}$ represents H;
$R^2$ represents H, $(C_1-C_3)$alkyl, hydroxy-$(C_1-C_3)$alkyl, benzyl or $(C_3-C_5)$cycloalkyl;
$R^3$ represents H or halogen (especially fluorine);
U represents N or $CR^4$; wherein $R^4$ is H or $(C_1-C_3)$alkoxy;
A represents CH, B represents NH and m represents 1 and n represent 1 or m represents 2 and n represents 2; or A represents N, B is absent (i.e. A is directly bound to the $CH_2$ group), m represents 2 and n represents 2;
Y represents CH or N; and
Q represents O or S.

5) Another embodiment of the invention relates to the compounds of formula $I_P$ according to embodiment 4) which are also compounds of formula $I_{PE1}$

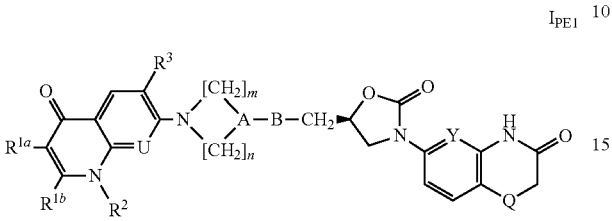

$I_{PE1}$ wherein the absolute configuration of the oxazolidinone moiety is as depicted in formula $I_{E1}$ [i.e. the absolute configuration of the oxazolidinone moiety is (R)].

6) Yet another embodiment of the invention relates to the compounds of formula $I_P$ according to embodiment 4) which are also compounds of formula $I_{PE2}$

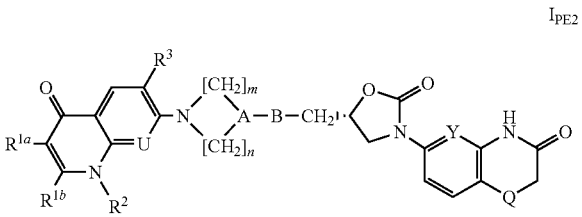

$I_{PE2}$ wherein the absolute configuration of the oxazolidinone moiety is as depicted in formula $I_{PE2}$ [i.e. the absolute configuration of the oxazolidinone moiety is (S)].

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a straight or branched chain alkyl group containing from one to four carbon atoms. The term "$(C_1-C_x)$alkyl" (x being an integer) refers to a straight or branched chain alkyl group containing 1 to x carbon atoms. For example, a $(C_1-C_3)$alkyl group contains from one to three carbon atoms. Representative examples of alkyl groups include methyl, ethyl, propyl, iso-propyl, n-butyl, iso-butyl, sec-butyl and tert-butyl. Preferred are methyl and ethyl.

The term "$(C_x-C_y)$hydroxyalkyl" (each of x and y being an integer) refers to a hydroxyalkyl group wherein the alkyl group contains x to y carbon atoms. Representative examples of $(C_1-C_3)$hydroxyalkyl groups include, but are not limited to, hydroxymethyl, 2-hydroxy-ethyl, 1-hydroxy-ethyl and 3-hydroxy-propyl. Preferred $(C_1-C_3)$hydroxyalkyl groups are 2-hydroxy-ethyl and 3-hydroxy-propyl. Representative examples of $(C_2-C_3)$hydroxyalkyl groups include, but are not limited to, 2-hydroxy-ethyl, 1-hydroxy-ethyl, 2-hydroxy-propyl and 3-hydroxy-propyl. Preferred $(C_2-C_3)$hydroxyalkyl groups are 2-hydroxy-ethyl and 3-hydroxy-propyl.

The term "cycloalkyl" refers to a saturated monocyclic group with three to six carbon ring-atoms, for example cyclopropyl, cyclobutyl, cyclopentyl, cyclohexyl. The term "$(C_3-C_x)$cycloalkyl" (x being an integer between 4 and 6) refers to a saturated monocyclic group containing 3 to x carbon atoms. For example, a $(C_3-C_5)$cycloalkyl group contains from three to five carbon atoms. Any cycloalkyl group as defined herein may be substituted with one, two halogen substituents in particular fluorine. The term "cycloalkyl" preferably refers to cyclopropyl.

The term "alkoxy" refers to a straight or branched chain alkoxy group containing from one to four carbon atoms. The term "$(C_x-C_y)$alkoxy" (x and y each being an integer) refers to an alkoxy group as defined before containing x to y carbon atoms. For example, a $(C_1-C_3)$alkoxy group contains from one to three carbon atoms. Representative examples of alkoxy groups include methoxy, ethoxy, n-propoxy and iso-propoxy. Preferred are methoxy and ethoxy. Most preferred is methoxy. For the substituent $R^4$ preferred is methoxy.

The term "halogen" refers to fluorine, chlorine, bromine or iodine, and preferably to fluorine or chlorine.

The term "carboxy" refers to the group —COOH.

7) A further embodiment of the present invention relates to compounds of formula I according to any one of embodiments 1) to 6) wherein $R^{1a}$ represents carboxy and $R^{1b}$ represents H, or $R^{1a}$ and $R^{1b}$ represent together either the group *—C(O)—NH—S—# or the group *—C(OH)=N—S—# wherein "*" represents the point of attachment of $R^{1a}$ and "#" represents the point of attachment of $R^{1a}$.

8) According to one variant of embodiment 7), the compounds of formula I according to embodiment 7) will be such that $R^{1a}$ represents carboxy and $R^{1b}$ represents H.

9) According to the other variant of embodiment 7), the compounds of formula I according to embodiment 7) will be such that $R^{1a}$ and $R^{1b}$ represent together either the group *—C(O)—NH—S—# or the group *—C(OH)=N—S—# wherein "*" represents the point of attachment of $R^{1a}$ and "#" represents the point of attachment of $R^{1b}$.

10) A further embodiment of the present invention relates to compounds of formula I according to any one of embodiments 1) to 9) wherein $R^2$ represents H, $(C_1-C_3)$alkyl, hydroxy-$(C_2-C_3)$alkyl, benzyl or $(C_3-C_5)$cycloalkyl.

11) According to one variant of embodiment 10), the compounds of formula I according to embodiment 10) will be such that $R^2$ represents $(C_1-C_3)$alkyl or $(C_3-C_5)$cycloalkyl (especially cyclopropyl).

12) According to another variant of embodiment 10), the compounds of formula I according to embodiment 10) will be such that $R^2$ represents benzyl.

13) According to yet another variant of embodiment 10), the compounds of formula I according to embodiment 10) will be such that $R^2$ represents cyclopropyl.

14) A further embodiment of the present invention relates to compounds of formula I according to any one of embodiments 1) to 13) wherein $R^3$ represents halogen (especially fluorine).

15) A further embodiment of the present invention relates to compounds of formula I according to any one of embodiments 1) to 14) wherein U represents N.

16) A further embodiment of the present invention relates to compounds of formula I according to any one of embodiments 1) to 14) wherein U represents $CR^4$ wherein $R^4$ is H or $(C_1-C_3)$alkoxy (especially H).

17) A further embodiment of the present invention relates to the compounds of formula I according to any one of embodiments 1) to 3), or to the compounds of formula I as defined in any of embodiments 1) to 3) taken together with any of embodiments 7) to 16), wherein the group

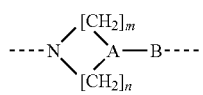

is selected from the groups

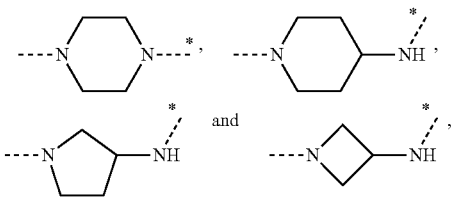

wherein the asterisks denote the bond linking said groups to the $CH_2$ group which is attached to the oxazolidinone moiety.

18) According to a particular variant of embodiment 17), the compounds of formula I according to embodiment 17) will be such that the group

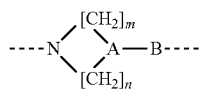

is the group

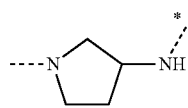

wherein the asterisk denotes the bond linking said group to the $CH_2$ group which is attached to the oxazolidinone moiety.

19) A further embodiment of the present invention relates to the compounds of formula I according to any one of embodiment 4) to 6), or to the compounds of formula I as defined in any of embodiments 4) to 6) taken together with any of embodiments 7) to 16), wherein the group

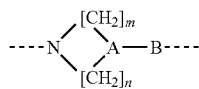

is selected from the groups

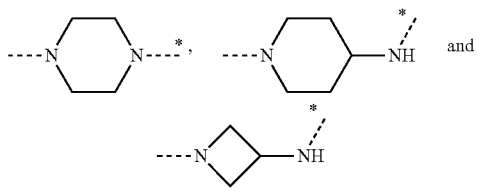

(and especially from the groups

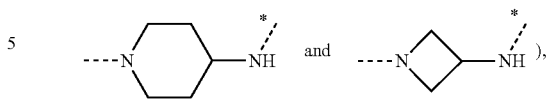

wherein the asterisks denote the bond linking said groups to the $CH_2$ group which is attached to the oxazolidinone moiety.

20) Yet a further embodiment of the present invention relates to the compounds of formula I as defined in any of embodiments 1) to 3), or to the compounds of formula I as defined in any of embodiments 1) to 3) taken together with any of embodiments 7) to 16), wherein A represents CH, B represents NH, m represents 1 or 2 and n represents 1 or 2.

21) According to one variant of embodiment 20), the compounds of formula I according to embodiment 20) will be such that A represents CH, B represents NH, m represents 1 and n represents 1.

22) According to another variant of embodiment 20), the compounds of formula I according to embodiment 20) will be such that A represents CH, B represents NH, m represents 1 and n represents 2.

23) According to yet another variant of embodiment 20), the compounds of formula I according to embodiment 20) will be such that A represents CH, B represents NH, m represents 2 and n represents 2.

24) A further embodiment of the present invention relates to the compounds of formula I according to any one of embodiments 4) to 6), or according to any one of embodiments 4) to 6) taken together with any one of embodiments 8) and 11) to 16), wherein A represents CH, B represents NH and each of m and n represents 1.

25) A further embodiment of the present invention relates to the compounds of formula I according to any one of embodiments 4) to 6), or according to any one of embodiments 4) to 6) taken together with any one of embodiments 8) and 11) to 16), wherein A represents N, B is absent and each of m and n represents 2.

26) A further embodiment of the present invention relates to the compounds of formula I according to any one of embodiments 4) to 6), or according to any one of embodiments 4) to 6) taken together with any one of embodiments 8) and 11) to 16), wherein A represents CH, B is NH and each of m and n represents 2.

27) A further embodiment of the present invention relates to the compounds of formula I according to any one of embodiments 1) to 26) wherein Y represents CH or N and Q represents O, or Y represents CH and Q represents S.

28) A further embodiment of the present invention relates to the compounds of formula I according to any one of embodiments 1) to 26) wherein Y represents N and Q represents O, or Y represents CH and Q represents S.

29) A particular embodiment of the present invention relates to the compounds of formula I according to any of embodiments 1) to 3), wherein:
  $R^{1a}$ represents carboxy and $R^{1b}$ represents H, or $R^{1a}$ and $R^{1b}$ represent together either the group *—C(O)—NH—S—# or the group *—C(OH)=N—S—# wherein "*" represents the point of attachment of $R^{1a}$ and "#" represents the point of attachment of $R^{1b}$;
  $R^2$ represents cyclopropyl;
  $R^3$ represents fluorine;
  U represents N;
  A represents CH, B represents NH, m represents 1 or 2 and n represents 1 or 2;
  Y represents N; and
  Q represents O.

30) According to a main variant of this invention, the compounds of formula I as defined in embodiment 1) will also be compounds of formula I$_2$

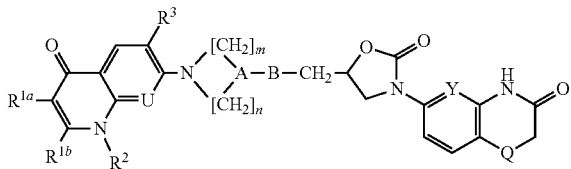

I$_2$ wherein
R$^{1a}$ represents H or carboxy and R$^{1b}$ represents H;
R$^2$ represents H, (C$_1$-C$_3$)alkyl, hydroxy-(C$_1$-C$_3$)alkyl, benzyl or (C$_3$-C$_5$)cycloalkyl;
R$^3$ represents H or halogen (especially fluorine);
U represents N or CR$^4$, wherein R$^4$ is H or (C$_1$-C$_3$)alkoxy;
A represents CH, B represents NH, m represents 1 or 2 and n represents 1 or 2; or A represents N, B is absent (i.e. A is directly bound to the CH$_2$ group), m represents 2 and n represents 2;
Y represents CH or N; and
Q represents O or S.

31) A particular embodiment of the present invention relates to the compounds of formula I according to embodiment 30), wherein:
R$^{1a}$ represents carboxy and R$^{1b}$ represents H;
R$^2$ represents cyclopropyl;
R$^3$ represents fluorine;
U represents N;
A represents CH, B represents NH, m represents 1 or 2 and n represents 1 or 2;
Y represents N; and
Q represents O.

32) According to another main variant of this invention, the compounds of formula I as defined in embodiment 1) will also be compounds of formula I$_3$ or I$_3$'

U represents N or CR$^4$, wherein R$^4$ is H or (C$_1$-C$_3$)alkoxy;
A represents CH, B represents NH, m represents 1 or 2 and n represents 1 or 2; or A represents N, B is absent (i.e. A is directly bound to the CH$_2$ group), m represents 2 and n represents 2;
Y represents CH or N; and
Q represents O or S.

33) A particular embodiment of the present invention relates to the compounds of formula I according to embodiment 32), wherein:
R$^2$ represents cyclopropyl;
R$^3$ represents fluorine;
U represents N;
A represents CH, B represents NH, m represents 1 or 2 and n represents 1 or 2;
Y represents N; and
Q represents O.

34) A further embodiment of the present invention relates to compounds of formula I according to embodiment 1) or 4), which are selected from the group consisting of:
1-cyclopropyl-6-fluoro-4-oxo-7-{4-[(R)-2-oxo-3-(3-oxo-3,4-dihydro-2H-benzo[1,4]thiazin-6-yl)-oxazolidin-5-ylmethyl]-piperazin-1-yl}-1,4-dihydro-quinoline-3-carboxylic acid;
1-cyclopropyl-6-fluoro-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-[1,8]naphthyridine-3-carboxylic acid;
1-cyclopropyl-6-fluoro-4-oxo-7-{4-[(R)-2-oxo-3-(3-oxo-3,4-dihydro-2H-pyrido[3,2-b][1,4]thiazin-6-yl)-oxazolidin-5-ylmethyl]-piperazin-1-yl}-1,4-dihydro-quinoline-3-carboxylic acid;
1-cyclopropyl-6-fluoro-4-oxo-7-{4-[(R)-2-oxo-3-(3-oxo-3,4-dihydro-2H-benzo[1,4]thiazin-6-yl)-oxazolidin-5-ylmethyl]-piperazin-1-yl}-1,4-dihydro-[1,8]naphthyridine-3-carboxylic acid;
6-((R)-5-{[1-(8-cyclopropyl-3-fluoro-5-oxo-5,8-dihydro-[1,8]naphthyridin-2-yl)-azetidin-3-ylamino]-methyl}-2-oxo-oxazolidin-3-yl)-4H-benzo[1,4]thiazin-3-one;

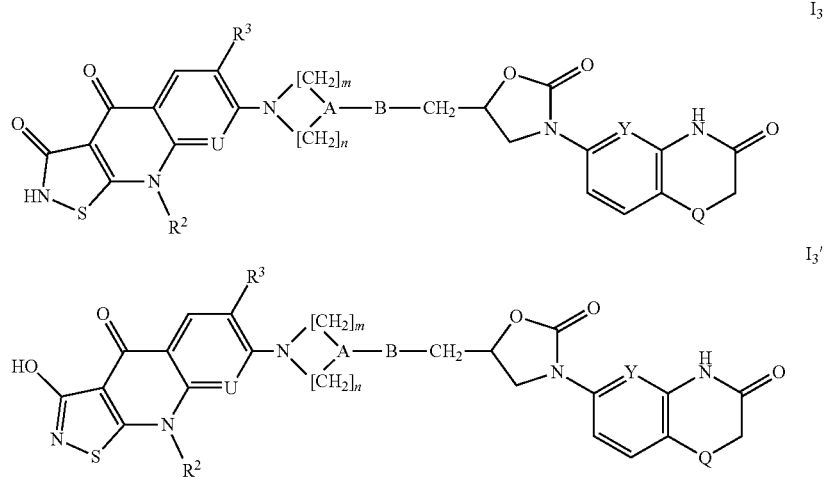

I$_3$

I$_3$' wherein
R$^2$ represents H, (C$_1$-C$_3$)alkyl, hydroxy-(C$_1$-C$_3$)alkyl, benzyl or (C$_3$-C$_5$)cycloalkyl;
R$^3$ represents H or halogen (especially fluorine);

1-cyclopropyl-6-fluoro-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;

1-cyclopropyl-8-methoxy-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-quinoline-3-carboxylic acid;

1-cyclopropyl-8-methoxy-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-quinoline-3-carboxylic acid;

1-ethyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;

1-cyclopropyl-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-[1,8]naphthyridine-3-carboxylic acid;

1-methyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;

6-fluoro-1-methyl-4-oxo-7-(3-{[(R)-2-oxo-3-(3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;

1-benzyl-6-fluoro-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;

1-cyclopropyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;

6-fluoro-1-(2-hydroxy-ethyl)-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;

1-cyclopropyl-6-fluoro-4-oxo-7-{4-[(S)-2-oxo-3-(3-oxo-3,4-dihydro-2H-benzo[1,4]thiazin-6-yl)-oxazolidin-5-ylmethyl]-piperazin-1-yl}-1,4-dihydro-[1,8]naphthyridine-3-carboxylic acid;

1-cyclopropyl-6-fluoro-4-oxo-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-1,4-dihydro-[1,8]naphthyridine-3-carboxylic acid; and 1-cyclopropyl-6-fluoro-4-oxo-7-{4-[(R)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1,8]naphthyridine-3-carboxylic acid.

35) Yet a further embodiment of the present invention relates to compounds of formula I according to embodiment 1), which are selected from the group consisting of:

1-cyclopropyl-6-fluoro-4-oxo-7-{4-[(S)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1,8]naphthyridine-3-carboxylic acid;

1-cyclopropyl-6-fluoro-4-oxo-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-1,4-dihydro-[1,8]naphthyridine-3-carboxylic acid;

1-cyclopropyl-6-fluoro-4-oxo-7-(3-{[(S)-2-oxo-3-(3-oxo-3,4-dihydro-2H-pyrido[3,2-b][1,4]oxazin-6-yl)-oxazolidin-5-ylmethyl]-amino}-pyrrolidin-1-yl)-1,4-dihydro-[1,8]naphthyridine-3-carboxylic acid;

1-cyclopropyl-6-fluoro-4-oxo-7-[(S)-3-{[(S)-2-oxo-3-(3-oxo-3,4-dihydro-2H-pyrido[3,2-b][1,4]oxazin-6-yl)-oxazolidin-5-ylmethyl]-amino}-methyl)-pyrrolidin-1-yl]-1,4-dihydro-[1,8]naphthyridine-3-carboxylic acid;

9-cyclopropyl-6-fluoro-3-hydroxy-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-9H-1-thia-2,8,9-triaza-cyclopenta[b]naphthalen-4-one;

9-cyclopropyl-6-fluoro-3-hydroxy-7-(3-{[(S)-2-oxo-3-(3-oxo-3,4-dihydro-2H-pyrido[3,2-b][1,4]oxazin-6-yl)-oxazolidin-5-ylmethyl]-amino}-azetidin-1-yl)-9H-1-thia-2,8,9-triaza-cyclopenta[b]naphthalen-4-one; and 9-cyclopropyl-6-fluoro-3-hydroxy-7-{4-[(S)-2-oxo-3-(3-oxo-3,4-dihydro-2H-pyrido[3,2-b][1,4]oxazin-6-yl)-oxazolidin-5-ylmethyl]-piperazin-1-yl}-9H-1-thia-2,8,9-triaza-cyclopenta[b]naphthalen-4-one.

36) The invention furthermore relates to the groups of compounds of formula I selected from the group consisting of the compounds listed in embodiments 34) and 35), which groups of compounds furthermore correspond to one of embodiments 2) to 33), as well as to the salts (in particular the pharmaceutically acceptable salts) of such compounds.

37) The invention moreover relates to any individual compound of formula I selected from the group consisting of the compounds listed in embodiments 34) and 35), and to the salts (in particular the pharmaceutically acceptable salts) of such individual compound.

Where the plural form is used for compounds, salts, pharmaceutical compositions, diseases or the like, this is intended to mean also a single compound, salt, disease or the like.

Any reference to compounds of formula I, $I_{E1}$, $I_{E2}$, $I_P$, $I_{PE1}$, $I_{PE2}$, $I_2$, $I_3$ and $I_3'$ is to be understood as referring also to the salts, especially the pharmaceutically acceptable salts of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

Besides, the term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The present invention also includes isotope labeled, especially $^2$H (deuterium) labeled compounds of formula I as defined in any one of embodiments 1) to 36), which compounds are identical to the compounds of formula I except that one or more atoms have each been replaced by an atom having the same atomic number but an atomic mass different from the atomic mass usually found in nature. Isotope labeled, especially $^2$H (deuterium) labeled compounds of formula I and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula I are not isotope labeled, or they are labeled only with one or more deuterium atoms. In a sub-embodiment, the compounds of formula I are not isotope labeled at all. Isotope labeled compounds of formula I may be prepared in analogy to the methods described hereinafter, but using the appropriate isotope variation of suitable reagents or starting materials.

The compounds of formula I and their pharmaceutically acceptable salts can be used as medicaments, e.g. in the form of pharmaceutical compositions for enteral (such especially oral) or parenteral administration (including topical application or inhalation).

In a preferred embodiment of the invention, the administered amount of compound of formula I will be comprised between 1 mg and 1000 mg per day, particularly between 5 mg and 500 mg per day, more particularly between 25 mg and 400 mg per day, especially between 50 mg and 200 mg per day.

A further aspect of the invention are pharmaceutical compositions comprising a compound of formula I, or a pharmaceutically acceptable salt thereof, and a pharmaceutically acceptable excipient/carrier material.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula I according to the invention, i.e. according to any one of embodiments 1) to 37) above, are suitable for the use as chemotherapeutic active compounds in human and veterinary medicine and as substances for preserving inorganic and organic materials in particular all types of organic materials for example polymers, lubricants, paints, fibres, leather, paper and wood.

The compounds of formula I according to any one of embodiments 1) to 37) are particularly active against bacteria and bacteria-like organisms. They may therefore be particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

The compounds of formula I according to any one of embodiments 1) to 37), or the pharmaceutically acceptable salt thereof, may be used for the preparation of a medicament, and are suitable, for the prevention or treatment of a bacterial infection.

Accordingly, the compounds of formula I according to any one of embodiments 1) to 37), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

The compounds of formula I according to any one of embodiments 1) to 37) may further be useful for the preparation of a medicament, and are suitable, for the treatment of infections that are mediated by Gram negative bacteria, such as *E. coli, Klebsiella pneumoniae* and other Enterobacteriaceae, *Acinetobacter* spp. including *Acinetobacter baumanii, Pseudomonas aeruginiosa, Stenotrophomonas maltophilia, Neisseria meningitidis*, and *Bacteroides* spp.

The compounds of formula I according to any one of embodiments 1) to 37) may further be useful for the preparation of a medicament, and are suitable, for the treatment of infections that are mediated by Gram positive bacteria such as *Bacillus cereus, Bacillus anthracis, Clostridium difficile, Corynebacterium* spp. and *Propionibacterium acnes*.

The compounds of formula I according to any one of embodiments 1) to 37) may further be useful for the preparation of a medicament, and are suitable, for the treatment of protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula I according to any one of embodiments 1) to 37), or of a pharmaceutically acceptable salt thereof, for the manufacture of a medicament for the prevention or treatment of a bacterial infection. Another aspect of this invention relates to a compound of formula I according to any one of embodiments 1) to 37), or of a pharmaceutically acceptable salt thereof, for the prevention or treatment of a bacterial infection (in particular for the prevention or treatment of a bacterial infection caused by *Staphylococcus aureus* or *Acinetobacter baumanii* bacteria, and notably caused by quinolone-resistant *Staphylococcus aureus* or *Acinetobacter baumanii* bacteria).

Another aspect of the invention concerns a method for the prevention or the treatment of an infection as detailed above (and in particular for the prevention or treatment of a bacterial infection caused by *Staphylococcus aureus* or *Acinetobacter baumanii* bacteria, and notably caused by quinolone-resistant *Staphylococcus aureus* or *Acinetobacter baumanii* bacteria) in a patient comprising the administration to said patient of a pharmaceutically active amount of a compound of formula I according to one of embodiments 1) to 37) or a pharmaceutically acceptable salt thereof.

As well as in humans, bacterial infections can also be treated using compounds of formula I (or pharmaceutically acceptable salts thereof) in other species like pigs, ruminants, horses, dogs, cats and poultry.

This invention, thus, relates to the compounds of formula I as defined in embodiment 1), or further limited under consideration of their respective dependencies by the characteristics of any one of embodiments 2) to 37), and to pharmaceutically acceptable salts thereof. It relates furthermore to the use of such compounds as medicaments, especially for the prevention or treatment of a bacterial infection, in particular for the prevention or treatment of a bacterial infection caused by *Staphylococcus aureus* or *Acinetobacter baumanii* bacteria, and notably caused by quinolone-resistant *Staphylococcus aureus* or *Acinetobacter baumanii* bacteria. The following embodiments relating to the compounds of formula I according to embodiment 1) are thus possible and intended and herewith specifically disclosed in individualized form:

7+1, 7+2, 7+3, 7+4, 7+5, 7+6, 8+7+1, 8+7+2, 8+7+3, 8+7+4, 8+7+5, 8+7+6, 9+7+1, 9+7+2, 9+7+3, 9+7+4, 9+7+5, 9+7+6, 10+1, 10+2, 10+3, 10+4, 10+5, 10+6, 10+7+1, 10+7+2, 10+7+3, 10+7+4, 10+7+5, 10+7+6, 10+8+7+1, 10+8+7+2, 10+8+7+3, 10+8+7+4, 10+8+7+5, 10+8+7+6, 10+9+7+1, 10+9+7+2, 10+9+7+3, 10+9+7+4, 10+9+7+5, 10+9+7+6, 11+10+1, 11+10+2, 11+10+3, 11+10+4, 11+10+5, 11+10+6, 11+10+7+1, 11+10+7+2, 11+10+7+3, 11+10+7+4, 11+10+7+5, 11+10+7+6, 11+10+8+7+1, 11+10+8+7+2, 11+10+8+7+3, 11+10+8+7+4, 11+10+8+7+5, 11+10+8+7+6, 11+10+9+7+1, 11+10+9+7+2, 11+10+9+7+3, 11+10+9+7+4, 11+10+9+7+5, 11+10+9+7+6, 12+10+1, 12+10+2, 12+10+3, 12+10+4, 12+10+5, 12+10+6, 12+10+7+1, 12+10+7+2, 12+10+7+3, 12+10+7+4, 12+10+7+5, 12+10+7+6, 12+10+8+7+1, 12+10+8+7+2, 12+10+8+7+3, 12+10+8+7+4, 12+10+8+7+5, 12+10+8+7+6, 12+10+9+7+1, 12+10+9+7+2, 12+10+9+7+3, 12+10+9+7+4, 12+10+9+7+5, 12+10+9+7+6, 13+10+1, 13+10+2, 13+10+3, 13+10+4, 13+10+5, 13+10+6, 13+10+7+1, 13+10+7+2, 13+10+7+3, 13+10+7+4, 13+10+7+5, 13+10+7+6, 13+10+8+7+1, 13+10+8+7+2, 13+10+8+7+3, 13+10+8+7+4, 13+10+8+7+5, 13+10+8+7+6, 13+10+9+7+1, 13+10+9+7+2, 13+10+9+7+3, 13+10+9+7+4, 13+10+9+7+5, 13+10+9+7+6, 14+1, 14+2, 14+3, 14+4, 14+5, 14+6, 14+7+1, 14+7+2, 14+7+3, 14+7+4, 14+7+5, 14+7+6, 14+8+7+1, 14+8+7+2, 14+8+7+3, 14+8+7+4, 14+8+7+5, 14+8+7+6, 14+9+7+1, 14+9+7+2, 14+9+7+3, 14+9+7+4, 14+9+7+5, 14+9+7+6, 14+10+1, 14+10+2, 14+10+3, 14+10+4, 14+10+5, 14+10+6, 14+10+7+1, 14+10+7+2, 14+10+7+3, 14+10+7+4, 14+10+7+5, 14+10+7+6, 14+10+8+7+1, 14+10+8+7+2, 14+10+8+7+3, 14+10+8+7+4, 14+10+8+7+5, 14+10+8+7+6, 14+10+9+7+1, 14+10+9+7+2, 14+10+9+7+3, 14+10+9+7+4, 14+10+9+7+5, 14+10+9+7+6, 14+11+10+1, 14+11+10+2, 14+11+10+3, 14+11+10+4, 14+11+10+5, 14+11+10+6, 14+11+10+7+1, 14+11+10+7+2, 14+11+10+7+3, 14+11+10+7+4, 14+11+10+7+5, 14+11+10+7+6, 14+11+10+8+7+1, 14+11+10+8+7+2, 14+11+10+8+7+3, 14+11+10+8+7+4, 14+11+10+8+7+5, 14+11+10+8+7+6, 14+11+10+9+7+1, 14+11+10+9+7+2, 14+11+10+9+7+3, 14+11+10+9+7+4, 14+11+10+9+7+5, 14+11+10+9+7+6, 14+12+10+1, 14+12+10+2, 14+12+10+3, 14+12+10+4, 14+12+10+5, 14+12+10+6, 14+12+10+7+1, 14+12+10+7+2, 14+12+10+7+3, 14+12+10+7+4, 14+12+10+7+5, 14+12+10+7+6, 14+12+10+8+7+1, 14+12+10+8+7+2, 14+12+10+8+7+3, 14+12+10+8+7+4, 14+12+10+8+7+5, 14+12+10+8+7+6, 14+12+10+9+7+1, 14+12+10+9+7+2, 14+12+10+9+7+3, 14+12+10+9+7+4, 14+12+10+9+7+5, 14+12+10+9+7+6, 14+13+10+1, 14+13+10+2, 14+13+10+3, 14+13+10+4, 14+13+10+5, 14+13+10+6, 14+13+10+7+1, 14+13+10+7+2, 14+13+10+7+3, 14+13+10+7+4, 14+13+10+7+5, 14+13+10+7+6, 14+13+10+8+7+1, 14+13+10+8+7+2, 14+13+10+8+7+3, 14+13+10+8+7+4, 14+13+10+8+7+5, 14+13+10+8+7+6, 14+13+10+9+7+1, 14+13+10+9+7+2, 14+13+10+9+7+3, 14+13+10+9+7+4, 14+13+10+9+7+5, 14+13+10+9+7+6, 15+1, 15+2, 15+3, 15+4, 15+5, 15+6, 15+7+1, 15+7+2, 15+7+3, 15+7+4, 15+7+5, 15+7+6, 15+8+7+1, 15+8+7+2, 15+8+7+3, 15+8+7+4, 15+8+7+5, 15+8+7+6, 15+9+7+1, 15+9+7+2, 15+9+7+3, 15+9+7+4, 15+9+7+5, 15+9+7+6, 15+10+1, 15+10+2, 15+10+3, 15+10+4, 15+10+5, 15+10+6, 15+10+7+1, 15+10+7+2, 15+10+7+3, 15+10+7+4, 15+10+7+5, 15+10+7+6, 15+10+8+7+1, 15+10+8+7+2, 15+10+8+7+3, 15+10+8+7+4, 15+10+8+7+5, 15+10+8+7+6, 15+10+9+7+1, 15+10+9+7+2, 15+10+9+7+3, 15+10+9+7+4, 15+10+9+7+5, 15+10+9+7+6, 15+11+10+1, 15+11+10+2, 15+11+10+3, 15+11+10+4, 15+11+10+5, 15+11+10+6, 15+11+10+7+1, 15+11+10+7+2, 15+11+10+7+3, 15+11+10+7+4, 15+11+10+7+5, 15+11+10+7+6, 15+11+10+8+7+1, 15+11+10+8+7+2, 15+11+10+8+7+3, 15+11+10+8+7+4, 15+11+10+8+7+5, 15+11+10+8+7+6, 15+11+10+9+7+1, 15+11+10+9+7+2, 15+11+10+9+7+3, 15+11+10+9+7+4, 15+11+10+9+7+5, 15+11+10+9+7+6, 15+12+10+1, 15+12+10+2, 15+12+10+3, 15+12+10+4, 15+12+10+5, 15+12+10+6, 15+12+10+7+1, 15+12+10+7+2, 15+12+10+7+3, 15+12+10+7+4, 15+12+10+7+5, 15+12+10+7+6, 15+12+10+8+7+1, 15+12+10+8+7+2, 15+12+10+8+7+3, 15+12+10+8+7+4, 15+12+10+8+7+5, 15+12+10+8+7+6, 15+12+10+9+7+1, 15+12+10+9+7+2, 15+12+10+9+7+3, 15+12+10+9+7+4, 15+12+10+9+7+5, 15+12+10+9+7+6, 15+13+10+1, 15+13+10+2, 15+13+10+3, 15+13+10+4, 15+13+10+5, 15+13+10+6, 15+13+10+7+1, 15+13+10+7+2, 15+13+10+7+3, 15+13+10+7+4, 15+13+10+7+5, 15+13+10+7+6, 15+13+10+8+7+

1, 15+13+10+8+7+2, 15+13+10+8+7+3, 15+13+10+8+7+4, 15+13+10+8+7+5, 15+13+10+8+7+6, 15+13+10+9+7+1, 15+13+10+9+7+2, 15+13+10+9+7+3, 15+13+10+9+7+4, 15+13+10+9+7+5, 15+13+10+9+7+6, 15+14+1, 15+14+2, 15+14+3, 15+14+4, 15+14+5, 15+14+6, 15+14+7+1, 15+14+7+2, 15+14+7+3, 15+14+7+4, 15+14+7+5, 15+14+7+6, 15+14+8+7+1, 15+14+8+7+2, 15+14+8+7+3, 15+14+8+7+4, 15+14+8+7+5, 15+14+8+7+6, 15+14+9+7+1, 15+14+9+7+2, 15+14+9+7+3, 15+14+9+7+4, 15+14+9+7+5, 15+14+9+7+6, 15+14+10+1, 15+14+10+2, 15+14+10+3, 15+14+10+4, 15+14+10+5, 15+14+10+6, 15+14+10+7+1, 15+14+10+7+2, 15+14+10+7+3, 15+14+10+7+4, 15+14+10+7+5, 15+14+10+7+6, 15+14+10+8+7+1, 15+14+10+8+7+2, 15+14+10+8+7+3, 15+14+10+8+7+4, 15+14+10+8+7+5, 15+14+10+8+7+6, 15+14+10+9+7+1, 15+14+10+9+7+2, 15+14+10+9+7+3, 15+14+10+9+7+4, 15+14+10+9+7+5, 15+14+10+9+7+6, 15+14+11+10+1, 15+14+11+10+2, 15+14+11+10+3, 15+14+11+10+4, 15+14+11+10+5, 15+14+11+10+6, 15+14+11+10+7+1, 15+14+11+10+7+2, 15+14+11+10+7+3, 15+14+11+10+7+4, 15+14+11+10+7+5, 15+14+11+10+7+6, 15+14+11+10+8+7+1, 15+14+11+10+8+7+2, 15+14+11+10+8+7+3, 15+14+11+10+8+7+4, 15+14+11+10+8+7+5, 15+14+11+10+8+7+6, 15+14+11+10+9+7+1, 15+14+11+10+9+7+2, 15+14+11+10+9+7+3, 15+14+11+10+9+7+4, 15+14+11+10+9+7+5, 15+14+11+10+9+7+6, 15+14+12+10+1, 15+14+12+10+2, 15+14+12+10+3, 15+14+12+10+4, 15+14+12+10+5, 15+14+12+10+6, 15+14+12+10+7+1, 15+14+12+10+7+2, 15+14+12+10+7+3, 15+14+12+10+7+4, 15+14+12+10+7+5, 15+14+12+10+7+6, 15+14+12+10+8+7+1, 15+14+12+10+8+7+2, 15+14+12+10+8+7+3, 15+14+12+10+8+7+4, 15+14+12+10+8+7+5, 15+14+12+10+8+7+6, 15+14+12+10+9+7+1, 15+14+12+10+9+7+2, 15+14+12+10+9+7+3, 15+14+12+10+9+7+4, 15+14+12+10+9+7+5, 15+14+12+10+9+7+6, 15+14+13+10+1, 15+14+13+10+2, 15+14+13+10+3, 15+14+13+10+4, 15+14+13+10+5, 15+14+13+10+6, 15+14+13+10+7+1, 15+14+13+10+7+2, 15+14+13+10+7+3, 15+14+13+10+7+4, 15+14+13+10+7+5, 15+14+13+10+7+6, 15+14+13+10+8+7+1, 15+14+13+10+8+7+2, 15+14+13+10+8+7+3, 15+14+13+10+8+7+4, 15+14+13+10+8+7+5, 15+14+13+10+8+7+6, 15+14+13+10+9+7+1, 15+14+13+10+9+7+2, 15+14+13+10+9+7+3, 15+14+13+10+9+7+4, 15+14+13+10+9+7+5, 15+14+13+10+9+7+6, 16+1, 16+2, 16+3, 16+4, 16+5, 16+6, 16+7+1, 16+7+2, 16+7+3, 16+7+4, 16+7+5, 16+7+6, 16+8+7+1, 16+8+7+2, 16+8+7+3, 16+8+7+4, 16+8+7+5, 16+8+7+6, 16+9+7+1, 16+9+7+2, 16+9+7+3, 16+9+7+4, 16+9+7+5, 16+9+7+6, 16+10+1, 16+10+2, 16+10+3, 16+10+4, 16+10+5, 16+10+6, 16+10+7+1, 16+10+7+2, 16+10+7+3, 16+10+7+4, 16+10+7+5, 16+10+7+6, 16+10+8+7+1, 16+10+8+7+2, 16+10+8+7+3, 16+10+8+7+4, 16+10+8+7+5, 16+10+8+7+6, 16+10+9+7+1, 16+10+9+7+2, 16+10+9+7+3, 16+10+9+7+4, 16+10+9+7+5, 16+10+9+7+6, 16+11+10+1, 16+11+10+2, 16+11+10+3, 16+11+10+4, 16+11+10+5, 16+11+10+6, 16+11+10+7+1, 16+11+10+7+2, 16+11+10+7+3, 16+11+10+7+4, 16+11+10+7+5, 16+11+10+7+6, 16+11+10+8+7+1, 16+11+10+8+7+2, 16+11+10+8+7+3, 16+11+10+8+7+4, 16+11+10+8+7+5, 16+11+10+8+7+6, 16+11+10+9+7+1, 16+11+10+9+7+2, 16+11+10+9+7+3, 16+11+10+9+7+4, 16+11+10+9+7+5, 16+11+10+9+7+6, 16+12+10+1, 16+12+10+2, 16+12+10+3, 16+12+10+4, 16+12+10+5, 16+12+10+6, 16+12+10+7+1, 16+12+10+7+2, 16+12+10+7+3, 16+12+10+7+4, 16+12+10+7+5, 16+12+10+7+6, 16+12+10+8+7+1, 16+12+10+8+7+2, 16+12+10+8+7+3, 16+12+10+8+7+4, 16+12+10+8+7+5, 16+12+10+8+7+6, 16+12+10+9+7+1, 16+12+10+9+7+2, 16+12+10+9+7+3, 16+12+10+9+7+4, 16+12+10+9+7+5, 16+12+10+9+7+6, 16+13+10+1, 16+13+10+2, 16+13+10+3, 16+13+10+4, 16+13+10+5, 16+13+10+6, 16+13+10+7+1, 16+13+10+7+2, 16+13+10+7+3, 16+13+10+7+4, 16+13+10+7+5, 16+13+10+7+6, 16+13+10+8+7+1, 16+13+10+8+7+2, 16+13+10+8+7+3, 16+13+10+8+7+4, 16+13+10+8+7+5, 16+13+10+8+7+6, 16+13+10+9+7+1, 16+13+10+9+7+2, 16+13+10+9+7+3, 16+13+10+9+7+4, 16+13+10+9+7+5, 16+13+10+9+7+6, 16+14+1, 16+14+2, 16+14+3, 16+14+4, 16+14+5, 16+14+6, 16+14+7+1, 16+14+7+2, 16+14+7+3, 16+14+7+4, 16+14+7+5, 16+14+7+6, 16+14+8+7+1, 16+14+8+7+2, 16+14+8+7+3, 16+14+8+7+4, 16+14+8+7+5, 16+14+8+7+6, 16+14+9+7+1, 16+14+9+7+2, 16+14+9+7+3, 16+14+9+7+4, 16+14+9+7+5, 16+14+9+7+6, 16+14+10+1, 16+14+10+2, 16+14+10+3, 16+14+10+4, 16+14+10+5, 16+14+10+6, 16+14+10+7+1, 16+14+10+7+2, 16+14+10+7+3, 16+14+10+7+4, 16+14+10+7+5, 16+14+10+7+6, 16+14+10+8+7+1, 16+14+10+8+7+2, 16+14+10+8+7+3, 16+14+10+8+7+4, 16+14+10+8+7+5, 16+14+10+8+7+6, 16+14+10+9+7+1, 16+14+10+9+7+2, 16+14+10+9+7+3, 16+14+10+9+7+4, 16+14+10+9+7+5, 16+14+10+9+7+6, 16+14+11+10+1, 16+14+11+10+2, 16+14+11+10+3, 16+14+11+10+4, 16+14+11+10+5, 16+14+11+10+6, 16+14+11+10+7+1, 16+14+11+10+7+2, 16+14+11+10+7+3, 16+14+11+10+7+4, 16+14+11+10+7+5, 16+14+11+10+7+6, 16+14+11+10+8+7+1, 16+14+11+10+8+7+2, 16+14+11+10+8+7+3, 16+14+11+10+8+7+4, 16+14+11+10+8+7+5, 16+14+11+10+8+7+6, 16+14+11+10+9+7+1, 16+14+11+10+9+7+2, 16+14+11+10+9+7+3, 16+14+11+10+9+7+4, 16+14+11+10+9+7+5, 16+14+11+10+9+7+6, 16+14+12+10+1, 16+14+12+10+2, 16+14+12+10+3, 16+14+12+10+4, 16+14+12+10+5, 16+14+12+10+6, 16+14+12+10+7+1, 16+14+12+10+7+2, 16+14+12+10+7+3, 16+14+12+10+7+4, 16+14+12+10+7+5, 16+14+12+10+7+6, 16+14+12+10+8+7+1, 16+14+12+10+8+7+2, 16+14+12+10+8+7+3, 16+14+12+10+8+7+4, 16+14+12+10+8+7+5, 16+14+12+10+8+7+6, 16+14+12+10+9+7+1, 16+14+12+10+9+7+2, 16+14+12+10+9+7+3, 16+14+12+10+9+7+4, 16+14+12+10+9+7+5, 16+14+12+10+9+7+6, 16+14+13+10+1, 16+14+13+10+2, 16+14+13+10+3, 16+14+13+10+4, 16+14+13+10+5, 16+14+13+10+6, 16+14+13+10+7+1, 16+14+13+10+7+2, 16+14+13+10+7+3, 16+14+13+10+7+4, 16+14+13+10+7+5, 16+14+13+10+7+6, 16+14+13+10+8+7+1, 16+14+13+10+8+7+2, 16+14+13+10+8+7+3, 16+14+13+10+8+7+4, 16+14+13+10+8+7+5, 16+14+13+10+8+7+6, 16+14+13+10+9+7+1, 16+14+13+10+9+7+2, 16+14+13+10+9+7+3, 16+14+13+10+9+7+4, 16+14+13+10+9+7+5, 16+14+13+10+9+7+6, 17+1, 17+2, 17+3, 18+17+1, 18+17+2, 18+17+3, 19+4, 19+5, 19+6, 20+1, 20+2, 20+3, 21+20+1, 21+20+2, 21+20+3, 22+20+1, 22+20+2, 22+20+3, 23+20+1, 23+20+2, 23+20+3, 24+4, 24+5, 24+6, 25+4, 25+5, 25+6, 26+4, 26+5, 26+6, 27+1, 27+2, 27+3, 27+4, 27+5, 27+6, 27+7+1, 27+7+2, 27+7+3, 27+7+4, 27+7+5, 27+7+6, 27+8+7+1, 27+8+7+2, 27+8+7+3, 27+8+7+4, 27+8+7+5, 27+8+7+6, 27+9+7+1, 27+9+7+2, 27+9+7+3, 27+9+7+4, 27+9+7+5, 27+9+7+6, 27+10+1, 27+10+2, 27+10+3, 27+10+4, 27+10+5, 27+10+6, 27+10+7+1, 27+10+7+2, 27+10+7+3, 27+10+7+4, 27+10+7+5, 27+10+7+6, 27+10+8+7+1, 27+10+8+7+2, 27+10+8+7+3, 27+10+8+7+4, 27+10+8+7+5, 27+10+8+7+6, 27+10+9+7+1, 27+10+9+7+2, 27+10+9+7+3, 27+10+9+7+4, 27+10+9+7+5, 27+10+9+7+6, 27+11+10+1, 27+11+10+2, 27+11+10+3, 27+11+10+4, 27+11+10+5, 27+11+10+

6, 27+11+10+7+1, 27+11+10+7+2, 27+11+10+7+3, 27+11+10+7+4, 27+11+10+7+5, 27+11+10+7+6, 27+11+10+8+7+1, 27+11+10+8+7+2, 27+11+10+8+7+3, 27+11+10+8+7+4, 27+11+10+8+7+5, 27+11+10+8+7+6, 27+11+10+9+7+1, 27+11+10+9+7+2, 27+11+10+9+7+3, 27+11+10+9+7+4, 27+11+10+9+7+5, 27+11+10+9+7+6, 27+12+10+1, 27+12+10+2, 27+12+10+3, 27+12+10+4, 27+12+10+5, 27+12+10+6, 27+12+10+7+1, 27+12+10+7+2, 27+12+10+7+3, 27+12+10+7+4, 27+12+10+7+5, 27+12+10+7+6, 27+12+10+8+7+1, 27+12+10+8+7+2, 27+12+10+8+7+3, 27+12+10+8+7+4, 27+12+10+8+7+5, 27+12+10+8+7+6, 27+12+10+9+7+1, 27+12+10+9+7+2, 27+12+10+9+7+3, 27+12+10+9+7+4, 27+12+10+9+7+5, 27+12+10+9+7+6, 27+13+10+1, 27+13+10+2, 27+13+10+3, 27+13+10+4, 27+13+10+5, 27+13+10+6, 27+13+10+7+1, 27+13+10+7+2, 27+13+10+7+3, 27+13+10+7+4, 27+13+10+7+5, 27+13+10+7+6, 27+13+10+8+7+1, 27+13+10+8+7+2, 27+13+10+8+7+3, 27+13+10+8+7+4, 27+13+10+8+7+5, 27+13+10+8+7+6, 27+13+10+9+7+1, 27+13+10+9+7+2, 27+13+10+9+7+3, 27+13+10+9+7+4, 27+13+10+9+7+5, 27+13+10+9+7+6, 27+14+1, 27+14+2, 27+14+3, 27+14+4, 27+14+5, 27+14+6, 27+14+7+1, 27+14+7+2, 27+14+7+3, 27+14+7+4, 27+14+7+5, 27+14+7+6, 27+14+8+7+1, 27+14+8+7+2, 27+14+8+7+3, 27+14+8+7+4, 27+14+8+7+5, 27+14+8+7+6, 27+14+9+7+1, 27+14+9+7+2, 27+14+9+7+3, 27+14+9+7+4, 27+14+9+7+5, 27+14+9+7+6, 27+14+10+1, 27+14+10+2, 27+14+10+3, 27+14+10+4, 27+14+10+5, 27+14+10+6, 27+14+10+7+1, 27+14+10+7+2, 27+14+10+7+3, 27+14+10+7+4, 27+14+10+7+5, 27+14+10+7+6, 27+14+10+8+7+1, 27+14+10+8+7+2, 27+14+10+8+7+3, 27+14+10+8+7+4, 27+14+10+8+7+5, 27+14+10+8+7+6, 27+14+10+9+7+1, 27+14+10+9+7+2, 27+14+10+9+7+3, 27+14+10+9+7+4, 27+14+10+9+7+5, 27+14+10+9+7+6, 27+14+11+10+1, 27+14+11+10+2, 27+14+11+10+3, 27+14+11+10+4, 27+14+11+10+5, 27+14+11+10+6, 27+14+11+10+7+1, 27+14+11+10+7+2, 27+14+11+10+7+3, 27+14+11+10+7+4, 27+14+11+10+7+5, 27+14+11+10+7+6, 27+14+11+10+8+7+1, 27+14+11+10+8+7+2, 27+14+11+10+8+7+3, 27+14+11+10+8+7+4, 27+14+11+10+8+7+5, 27+14+11+10+8+7+6, 27+14+11+10+9+7+1, 27+14+11+10+9+7+2, 27+14+11+10+9+7+3, 27+14+11+10+9+7+4, 27+14+11+10+9+7+5, 27+14+11+10+9+7+6, 27+14+12+10+1, 27+14+12+10+2, 27+14+12+10+3, 27+14+12+10+4, 27+14+12+10+5, 27+14+12+10+6, 27+14+12+10+7+1, 27+14+12+10+7+2, 27+14+12+10+7+3, 27+14+12+10+7+4, 27+14+12+10+7+5, 27+14+12+10+7+6, 27+14+12+10+8+7+1, 27+14+12+10+8+7+2, 27+14+12+10+8+7+3, 27+14+12+10+8+7+4, 27+14+12+10+8+7+5, 27+14+12+10+8+7+6, 27+14+12+10+9+7+1, 27+14+12+10+9+7+2, 27+14+12+10+9+7+3, 27+14+12+10+9+7+4, 27+14+12+10+9+7+5, 27+14+12+10+9+7+6, 27+14+13+10+1, 27+14+13+10+2, 27+14+13+10+3, 27+14+13+10+4, 27+14+13+10+5, 27+14+13+10+6, 27+14+13+10+7+1, 27+14+13+10+7+2, 27+14+13+10+7+3, 27+14+13+10+7+4, 27+14+13+10+7+5, 27+14+13+10+7+6, 27+14+13+10+8+7+1, 27+14+13+10+8+7+2, 27+14+13+10+8+7+3, 27+14+13+10+8+7+4, 27+14+13+10+8+7+5, 27+14+13+10+8+7+6, 27+14+13+10+9+7+1, 27+14+13+10+9+7+2, 27+14+13+10+9+7+3, 27+14+13+10+9+7+4, 27+14+13+10+9+7+5, 27+14+13+10+9+7+6, 27+15+1, 27+15+2, 27+15+3, 27+15+4, 27+15+5, 27+15+6, 27+15+7+1, 27+15+7+2, 27+15+7+3, 27+15+7+4, 27+15+7+5, 27+15+7+6, 27+15+8+7+1, 27+15+8+7+2, 27+15+8+7+3, 27+15+8+7+4, 27+15+8+7+5, 27+15+8+7+6, 27+15+9+7+1, 27+15+9+7+2, 27+15+9+7+3, 27+15+9+7+4, 27+15+9+7+5, 27+15+9+7+6, 27+15+10+1, 27+15+10+2, 27+15+10+3, 27+15+10+4, 27+15+10+5, 27+15+10+6, 27+15+10+7+1, 27+15+10+7+2, 27+15+10+7+3, 27+15+10+7+4, 27+15+10+7+5, 27+15+10+7+6, 27+15+10+8+7+1, 27+15+10+8+7+2, 27+15+10+8+7+3, 27+15+10+8+7+4, 27+15+10+8+7+5, 27+15+10+8+7+6, 27+15+10+9+7+1, 27+15+10+9+7+2, 27+15+10+9+7+3, 27+15+10+9+7+4, 27+15+10+9+7+5, 27+15+10+9+7+6, 27+15+11+10+1, 27+15+11+10+2, 27+15+11+10+3, 27+15+11+10+4, 27+15+11+10+5, 27+15+11+10+6, 27+15+11+10+7+1, 27+15+11+10+7+2, 27+15+11+10+7+3, 27+15+11+10+7+4, 27+15+11+10+7+5, 27+15+11+10+7+6, 27+15+11+10+8+7+1, 27+15+11+10+8+7+2, 27+15+11+10+8+7+3, 27+15+11+10+8+7+4, 27+15+11+10+8+7+5, 27+15+11+10+8+7+6, 27+15+11+10+9+7+1, 27+15+11+10+9+7+2, 27+15+11+10+9+7+3, 27+15+11+10+9+7+4, 27+15+11+10+9+7+5, 27+15+11+10+9+7+6, 27+15+12+10+1, 27+15+12+10+2, 27+15+12+10+3, 27+15+12+10+4, 27+15+12+10+5, 27+15+12+10+6, 27+15+12+10+7+1, 27+15+12+10+7+2, 27+15+12+10+7+3, 27+15+12+10+7+4, 27+15+12+10+7+5, 27+15+12+10+7+6, 27+15+12+10+8+7+1, 27+15+12+10+8+7+2, 27+15+12+10+8+7+3, 27+15+12+10+8+7+4, 27+15+12+10+8+7+5, 27+15+12+10+8+7+6, 27+15+12+10+9+7+1, 27+15+12+10+9+7+2, 27+15+12+10+9+7+3, 27+15+12+10+9+7+4, 27+15+12+10+9+7+5, 27+15+12+10+9+7+6, 27+15+13+10+1, 27+15+13+10+2, 27+15+13+10+3, 27+15+13+10+4, 27+15+13+10+5, 27+15+13+10+6, 27+15+13+10+7+1, 27+15+13+10+7+2, 27+15+13+10+7+3, 27+15+13+10+7+4, 27+15+13+10+7+5, 27+15+13+10+7+6, 27+15+13+10+8+7+1, 27+15+13+10+8+7+2, 27+15+13+10+8+7+3, 27+15+13+10+8+7+4, 27+15+13+10+8+7+5, 27+15+13+10+8+7+6, 27+15+13+10+9+7+1, 27+15+13+10+9+7+2, 27+15+13+10+9+7+3, 27+15+13+10+9+7+4, 27+15+13+10+9+7+5, 27+15+13+10+9+7+6, 27+15+14+1, 27+15+14+2, 27+15+14+3, 27+15+14+4, 27+15+14+5, 27+15+14+6, 27+15+14+7+1, 27+15+14+7+2, 27+15+14+7+3, 27+15+14+7+4, 27+15+14+7+5, 27+15+14+7+6, 27+15+14+8+7+1, 27+15+14+8+7+2, 27+15+14+8+7+3, 27+15+14+8+7+4, 27+15+14+8+7+5, 27+15+14+8+7+6, 27+15+14+9+7+1, 27+15+14+9+7+2, 27+15+14+9+7+3, 27+15+14+9+7+4, 27+15+14+9+7+5, 27+15+14+9+7+6, 27+15+14+10+1, 27+15+14+10+2, 27+15+14+10+3, 27+15+14+10+4, 27+15+14+10+5, 27+15+14+10+6, 27+15+14+10+7+1, 27+15+14+10+7+2, 27+15+14+10+7+3, 27+15+14+10+7+4, 27+15+14+10+7+5, 27+15+14+10+7+6, 27+15+14+10+8+7+1, 27+15+14+10+8+7+2, 27+15+14+10+8+7+3, 27+15+14+10+8+7+4, 27+15+14+10+8+7+5, 27+15+14+10+8+7+6, 27+15+14+10+9+7+1, 27+15+14+10+9+7+2, 27+15+14+10+9+7+3, 27+15+14+10+9+7+4, 27+15+14+10+9+7+5, 27+15+14+10+9+7+6, 27+15+14+11+10+1, 27+15+14+11+10+2, 27+15+14+11+10+3, 27+15+14+11+10+4, 27+15+14+11+10+5, 27+15+14+11+10+6, 27+15+14+11+10+7+1, 27+15+14+11+10+7+2, 27+15+14+11+10+7+3, 27+15+14+11+10+7+4, 27+15+14+11+10+7+5, 27+15+14+11+10+7+6, 27+15+14+11+10+8+7+1, 27+15+14+11+10+8+7+2, 27+15+14+11+10+8+7+3, 27+15+14+11+10+8+7+4, 27+15+14+11+10+8+7+5, 27+15+14+11+10+8+7+6, 27+15+14+11+10+9+7+1, 27+15+14+11+10+9+7+2, 27+15+14+11+10+9+7+3, 27+15+14+11+10+9+7+4, 27+15+14+11+10+9+7+5, 27+15+14+11+10+9+7+6, 27+15+14+12+10+1, 27+15+14+12+10+2, 27+15+14+12+10+3, 27+15+14+12+10+4, 27+15+14+12+10+5, 27+15+14+12+10+6, 27+15+14+12+10+7+1, 27+15+14+12+10+7+2, 27+15+14+12+10+7+3, 27+15+14+12+10+7+4,

27+15+14+12+10+7+5, 27+15+14+12+10+7+6, 27+15+14+12+10+8+7+1, 27+15+14+12+10+8+7+2, 27+15+14+12+10+8+7+3, 27+15+14+12+10+8+7+4, 27+15+14+12+10+8+7+5, 27+15+14+12+10+8+7+6, 27+15+14+12+10+9+7+1, 27+15+14+12+10+9+7+2, 27+15+14+12+10+9+7+3, 27+15+14+12+10+9+7+4, 27+15+14+12+10+9+7+5, 27+15+14+12+10+9+7+6, 27+15+14+13+10+1, 27+15+14+13+10+2, 27+15+14+13+10+3, 27+15+14+13+10+4, 27+15+14+13+10+5, 27+15+14+13+10+6, 27+15+14+13+10+7+1, 27+15+14+13+10+7+2, 27+15+14+13+10+7+3, 27+15+14+13+10+7+4, 27+15+14+13+10+7+5, 27+15+14+13+10+7+6, 27+15+14+13+10+8+7+1, 27+15+14+13+10+8+7+2, 27+15+14+13+10+8+7+3, 27+15+14+13+10+8+7+4, 27+15+14+13+10+8+7+5, 27+15+14+13+10+8+7+6, 27+15+14+13+10+9+7+1, 27+15+14+13+10+9+7+2, 27+15+14+13+10+9+7+3, 27+15+14+13+10+9+7+4, 27+15+14+13+10+9+7+5, 27+15+14+13+10+9+7+6, 27+16+1, 27+16+2, 27+16+3, 27+16+4, 27+16+5, 27+16+6, 27+16+7+1, 27+16+7+2, 27+16+7+3, 27+16+7+4, 27+16+7+5, 27+16+7+6, 27+16+8+7+1, 27+16+8+7+2, 27+16+8+7+3, 27+16+8+7+4, 27+16+8+7+5, 27+16+8+7+6, 27+16+9+7+1, 27+16+9+7+2, 27+16+9+7+3, 27+16+9+7+4, 27+16+9+7+5, 27+16+9+7+6, 27+16+10+1, 27+16+10+2, 27+16+10+3, 27+16+10+4, 27+16+10+5, 27+16+10+6, 27+16+10+7+1, 27+16+10+7+2, 27+16+10+7+3, 27+16+10+7+4, 27+16+10+7+5, 27+16+10+7+6, 27+16+10+8+7+1, 27+16+10+8+7+2, 27+16+10+8+7+3, 27+16+10+8+7+4, 27+16+10+8+7+5, 27+16+10+8+7+6, 27+16+10+9+7+1, 27+16+10+9+7+2, 27+16+10+9+7+3, 27+16+10+9+7+4, 27+16+10+9+7+5, 27+16+10+9+7+6, 27+16+11+10+1, 27+16+11+10+2, 27+16+11+10+3, 27+16+11+10+4, 27+16+11+10+5, 27+16+11+10+6, 27+16+11+10+7+1, 27+16+11+10+7+2, 27+16+11+10+7+3, 27+16+11+10+7+4, 27+16+11+10+7+5, 27+16+11+10+7+6, 27+16+11+10+8+7+1, 27+16+11+10+8+7+2, 27+16+11+10+8+7+3, 27+16+11+10+8+7+4, 27+16+11+10+8+7+5, 27+16+11+10+8+7+6, 27+16+11+10+9+7+1, 27+16+11+10+9+7+2, 27+16+11+10+9+7+3, 27+16+11+10+9+7+4, 27+16+11+10+9+7+5, 27+16+11+10+9+7+6, 27+16+12+10+1, 27+16+12+10+2, 27+16+12+10+3, 27+16+12+10+4, 27+16+12+10+5, 27+16+12+10+6, 27+16+12+10+7+1, 27+16+12+10+7+2, 27+16+12+10+7+3, 27+16+12+10+7+4, 27+16+12+10+7+5, 27+16+12+10+7+6, 27+16+12+10+8+7+1, 27+16+12+10+8+7+2, 27+16+12+10+8+7+3, 27+16+12+10+8+7+4, 27+16+12+10+8+7+5, 27+16+12+10+8+7+6, 27+16+12+10+9+7+1, 27+16+12+10+9+7+2, 27+16+12+10+9+7+3, 27+16+12+10+9+7+4, 27+16+12+10+9+7+5, 27+16+12+10+9+7+6, 27+16+13+10+1, 27+16+13+10+2, 27+16+13+10+3, 27+16+13+10+4, 27+16+13+10+5, 27+16+13+10+6, 27+16+13+10+7+1, 27+16+13+10+7+2, 27+16+13+10+7+3, 27+16+13+10+7+4, 27+16+13+10+7+5, 27+16+13+10+7+6, 27+16+13+10+8+7+1, 27+16+13+10+8+7+2, 27+16+13+10+8+7+3, 27+16+13+10+8+7+4, 27+16+13+10+8+7+5, 27+16+13+10+8+7+6, 27+16+13+10+9+7+1, 27+16+13+10+9+7+2, 27+16+13+10+9+7+3, 27+16+13+10+9+7+4, 27+16+13+10+9+7+5, 27+16+13+10+9+7+6, 27+16+14+1, 27+16+14+2, 27+16+14+3, 27+16+14+4, 27+16+14+5, 27+16+14+6, 27+16+14+7+1, 27+16+14+7+2, 27+16+14+7+3, 27+16+14+7+4, 27+16+14+7+5, 27+16+14+7+6, 27+16+14+8+7+1, 27+16+14+8+7+2, 27+16+14+8+7+3, 27+16+14+8+7+4, 27+16+14+8+7+5, 27+16+14+8+7+6, 27+16+14+9+7+1, 27+16+14+9+7+2, 27+16+14+9+7+3, 27+16+14+9+7+4, 27+16+14+9+7+5, 27+16+14+9+7+6, 27+16+14+10+1, 27+16+14+10+2, 27+16+14+10+3, 27+16+14+10+4, 27+16+14+10+5, 27+16+14+10+6, 27+16+14+10+7+1, 27+16+14+10+7+2, 27+16+14+10+7+3, 27+16+14+10+7+4, 27+16+14+10+7+5, 27+16+14+10+7+6, 27+16+14+10+8+7+1, 27+16+14+10+8+7+2, 27+16+14+10+8+7+3, 27+16+14+10+8+7+4, 27+16+14+10+8+7+5, 27+16+14+10+8+7+6, 27+16+14+10+9+7+1, 27+16+14+10+9+7+2, 27+16+14+10+9+7+3, 27+16+14+10+9+7+4, 27+16+14+10+9+7+5, 27+16+14+10+9+7+6, 27+16+14+11+10+1, 27+16+14+11+10+2, 27+16+14+11+10+3, 27+16+14+11+10+4, 27+16+14+11+10+5, 27+16+14+11+10+6, 27+16+14+11+10+7+1, 27+16+14+11+10+7+2, 27+16+14+11+10+7+3, 27+16+14+11+10+7+4, 27+16+14+11+10+7+5, 27+16+14+11+10+7+6, 27+16+14+11+10+8+7+1, 27+16+14+11+10+8+7+2, 27+16+14+11+10+8+7+3, 27+16+14+11+10+8+7+4, 27+16+14+11+10+8+7+5, 27+16+14+11+10+8+7+6, 27+16+14+11+10+9+7+1, 27+16+14+11+10+9+7+2, 27+16+14+11+10+9+7+3, 27+16+14+11+10+9+7+4, 27+16+14+11+10+9+7+5, 27+16+14+11+10+9+7+6, 27+16+14+12+10+1, 27+16+14+12+10+2, 27+16+14+12+10+3, 27+16+14+12+10+4, 27+16+14+12+10+5, 27+16+14+12+10+6, 27+16+14+12+10+7+1, 27+16+14+12+10+7+2, 27+16+14+12+10+7+3, 27+16+14+12+10+7+4, 27+16+14+12+10+7+5, 27+16+14+12+10+7+6, 27+16+14+12+10+8+7+1, 27+16+14+12+10+8+7+2, 27+16+14+12+10+8+7+3, 27+16+14+12+10+8+7+4, 27+16+14+12+10+8+7+5, 27+16+14+12+10+8+7+6, 27+16+14+12+10+9+7+1, 27+16+14+12+10+9+7+2, 27+16+14+12+10+9+7+3, 27+16+14+12+10+9+7+4, 27+16+14+12+10+9+7+5, 27+16+14+12+10+9+7+6, 27+16+14+13+10+1, 27+16+14+13+10+2, 27+16+14+13+10+3, 27+16+14+13+10+4, 27+16+14+13+10+5, 27+16+14+13+10+6, 27+16+14+13+10+7+1, 27+16+14+13+10+7+2, 27+16+14+13+10+7+3, 27+16+14+13+10+7+4, 27+16+14+13+10+7+5, 27+16+14+13+10+7+6, 27+16+14+13+10+8+7+1, 27+16+14+13+10+8+7+2, 27+16+14+13+10+8+7+3, 27+16+14+13+10+8+7+4, 27+16+14+13+10+8+7+5, 27+16+14+13+10+8+7+6, 27+16+14+13+10+9+7+1, 27+16+14+13+10+9+7+2, 27+16+14+13+10+9+7+3, 27+16+14+13+10+9+7+4, 27+16+14+13+10+9+7+5, 27+16+14+13+10+9+7+6, 27+17+1, 27+17+2, 27+17+3, 27+18+17+1, 27+18+17+2, 27+18+17+3, 27+19+4, 27+19+5, 27+19+6, 27+20+1, 27+20+2, 27+20+3, 27+21+20+1, 27+21+20+2, 27+21+20+3, 27+22+20+1, 27+22+20+2, 27+22+20+3, 27+23+20+1, 27+23+20+2, 27+23+20+3, 27+24+4, 27+24+5, 27+24+6, 27+25+4, 27+25+5, 27+25+6, 27+26+4, 27+26+5, 27+26+6, 28+1, 28+2, 28+3, 28+4, 28+5, 28+6, 28+7+1, 28+7+2, 28+7+3, 28+7+4, 28+7+5, 28+7+6, 28+8+7+1, 28+8+7+2, 28+8+7+3, 28+8+7+4, 28+8+7+5, 28+8+7+6, 28+9+7+1, 28+9+7+2, 28+9+7+3, 28+9+7+4, 28+9+7+5, 28+9+7+6, 28+10+1, 28+10+2, 28+10+3, 28+10+4, 28+10+5, 28+10+6, 28+10+7+1, 28+10+7+2, 28+10+7+3, 28+10+7+4, 28+10+7+5, 28+10+7+6, 28+10+8+7+1, 28+10+8+7+2, 28+10+8+7+3, 28+10+8+7+4, 28+10+8+7+5, 28+10+8+7+6, 28+10+9+7+1, 28+10+9+7+2, 28+10+9+7+3, 28+10+9+7+4, 28+10+9+7+5, 28+10+9+7+6, 28+11+10+1, 28+11+10+2, 28+11+10+3, 28+11+10+4, 28+11+10+5, 28+11+10+6, 28+11+10+7+1, 28+11+10+7+2, 28+11+10+7+3, 28+11+10+7+4, 28+11+10+7+5, 28+11+10+7+6, 28+11+10+8+7+1, 28+11+10+8+7+2, 28+11+10+8+7+3, 28+11+10+8+7+4, 28+11+10+8+7+5, 28+11+10+8+7+6, 28+11+10+9+7+1, 28+11+10+9+7+2, 28+11+10+9+7+3, 28+11+10+9+7+4, 28+11+10+9+7+5, 28+11+10+9+7+6, 28+12+10+1, 28+12+10+2, 28+12+10+3, 28+12+10+4, 28+12+10+5, 28+12+10+6, 28+12+10+7+1, 28+12+10+7+2, 28+12+10+7+3, 28+12+

10+7+4, 28+12+10+7+5, 28+12+10+7+6, 28+12+10+8+7+1, 28+12+10+8+7+2, 28+12+10+8+7+3, 28+12+10+8+7+4, 28+12+10+8+7+5, 28+12+10+8+7+6, 28+12+10+9+7+1, 28+12+10+9+7+2, 28+12+10+9+7+3, 28+12+10+9+7+4, 28+12+10+9+7+5, 28+12+10+9+7+6, 28+13+10+1, 28+13+10+2, 28+13+10+3, 28+13+10+4, 28+13+10+5, 28+13+10+6, 28+13+10+7+1, 28+13+10+7+2, 28+13+10+7+3, 28+13+10+7+4, 28+13+10+7+5, 28+13+10+7+6, 28+13+10+8+7+1, 28+13+10+8+7+2, 28+13+10+8+7+3, 28+13+10+8+7+4, 28+13+10+8+7+5, 28+13+10+8+7+6, 28+13+10+9+7+1, 28+13+10+9+7+2, 28+13+10+9+7+3, 28+13+10+9+7+4, 28+13+10+9+7+5, 28+13+10+9+7+6, 28+14+1, 28+14+2, 28+14+3, 28+14+4, 28+14+5, 28+14+6, 28+14+7+1, 28+14+7+2, 28+14+7+3, 28+14+7+4, 28+14+7+5, 28+14+7+6, 28+14+8+7+1, 28+14+8+7+2, 28+14+8+7+3, 28+14+8+7+4, 28+14+8+7+5, 28+14+8+7+6, 28+14+9+7+1, 28+14+9+7+2, 28+14+9+7+3, 28+14+9+7+4, 28+14+9+7+5, 28+14+9+7+6, 28+14+10+1, 28+14+10+2, 28+14+10+3, 28+14+10+4, 28+14+10+5, 28+14+10+6, 28+14+10+7+1, 28+14+10+7+2, 28+14+10+7+3, 28+14+10+7+4, 28+14+10+7+5, 28+14+10+7+6, 28+14+10+8+7+1, 28+14+10+8+7+2, 28+14+10+8+7+3, 28+14+10+8+7+4, 28+14+10+8+7+5, 28+14+10+8+7+6, 28+14+10+9+7+1, 28+14+10+9+7+2, 28+14+10+9+7+3, 28+14+10+9+7+4, 28+14+10+9+7+5, 28+14+10+9+7+6, 28+14+11+10+1, 28+14+11+10+2, 28+14+11+10+3, 28+14+11+10+4, 28+14+11+10+5, 28+14+11+10+6, 28+14+11+10+7+1, 28+14+11+10+7+2, 28+14+11+10+7+3, 28+14+11+10+7+4, 28+14+11+10+7+5, 28+14+11+10+7+6, 28+14+11+10+8+7+1, 28+14+11+10+8+7+2, 28+14+11+10+8+7+3, 28+14+11+10+8+7+4, 28+14+11+10+8+7+5, 28+14+11+10+8+7+6, 28+14+11+10+9+7+1, 28+14+11+10+9+7+2, 28+14+11+10+9+7+3, 28+14+11+10+9+7+4, 28+14+11+10+9+7+5, 28+14+11+10+9+7+6, 28+14+12+10+1, 28+14+12+10+2, 28+14+12+10+3, 28+14+12+10+4, 28+14+12+10+5, 28+14+12+10+6, 28+14+12+10+7+1, 28+14+12+10+7+2, 28+14+12+10+7+3, 28+14+12+10+7+4, 28+14+12+10+7+5, 28+14+12+10+7+6, 28+14+12+10+8+7+1, 28+14+12+10+8+7+2, 28+14+12+10+8+7+3, 28+14+12+10+8+7+4, 28+14+12+10+8+7+5, 28+14+12+10+8+7+6, 28+14+12+10+9+7+1, 28+14+12+10+9+7+2, 28+14+12+10+9+7+3, 28+14+12+10+9+7+4, 28+14+12+10+9+7+5, 28+14+12+10+9+7+6, 28+14+13+10+1, 28+14+13+10+2, 28+14+13+10+3, 28+14+13+10+4, 28+14+13+10+5, 28+14+13+10+6, 28+14+13+10+7+1, 28+14+13+10+7+2, 28+14+13+10+7+3, 28+14+13+10+7+4, 28+14+13+10+7+5, 28+14+13+10+7+6, 28+14+13+10+8+7+1, 28+14+13+10+8+7+2, 28+14+13+10+8+7+3, 28+14+13+10+8+7+4, 28+14+13+10+8+7+5, 28+14+13+10+8+7+6, 28+14+13+10+9+7+1, 28+14+13+10+9+7+2, 28+14+13+10+9+7+3, 28+14+13+10+9+7+4, 28+14+13+10+9+7+5, 28+14+13+10+9+7+6, 28+15+1, 28+15+2, 28+15+3, 28+15+4, 28+15+5, 28+15+6, 28+15+7+1, 28+15+7+2, 28+15+7+3, 28+15+7+4, 28+15+7+5, 28+15+7+6, 28+15+8+7+1, 28+15+8+7+2, 28+15+8+7+3, 28+15+8+7+4, 28+15+8+7+5, 28+15+8+7+6, 28+15+9+7+1, 28+15+9+7+2, 28+15+9+7+3, 28+15+9+7+4, 28+15+9+7+5, 28+15+9+7+6, 28+15+10+1, 28+15+10+2, 28+15+10+3, 28+15+10+4, 28+15+10+5, 28+15+10+6, 28+15+10+7+1, 28+15+10+7+2, 28+15+10+7+3, 28+15+10+7+4, 28+15+10+7+5, 28+15+10+7+6, 28+15+10+8+7+1, 28+15+10+8+7+2, 28+15+10+8+7+3, 28+15+10+8+7+4, 28+15+10+8+7+5, 28+15+10+8+7+6, 28+15+10+9+7+1, 28+15+10+9+7+2, 28+15+10+9+7+3, 28+15+10+9+7+4, 28+15+10+9+7+5, 28+15+10+9+7+6, 28+15+11+10+1, 28+15+11+10+2, 28+15+11+10+3, 28+15+11+10+4, 28+15+11+10+5, 28+15+11+10+6, 28+15+11+10+7+1, 28+15+11+10+7+2, 28+15+11+10+7+3, 28+15+11+10+7+4, 28+15+11+10+7+5, 28+15+11+10+7+6, 28+15+11+10+8+7+1, 28+15+11+10+8+7+2, 28+15+11+10+8+7+3, 28+15+11+10+8+7+4, 28+15+11+10+8+7+5, 28+15+11+10+8+7+6, 28+15+11+10+9+7+1, 28+15+11+10+9+7+2, 28+15+11+10+9+7+3, 28+15+11+10+9+7+4, 28+15+11+10+9+7+5, 28+15+11+10+9+7+6, 28+15+12+10+1, 28+15+12+10+2, 28+15+12+10+3, 28+15+12+10+4, 28+15+12+10+5, 28+15+12+10+6, 28+15+12+10+7+1, 28+15+12+10+7+2, 28+15+12+10+7+3, 28+15+12+10+7+4, 28+15+12+10+7+5, 28+15+12+10+7+6, 28+15+12+10+8+7+1, 28+15+12+10+8+7+2, 28+15+12+10+8+7+3, 28+15+12+10+8+7+4, 28+15+12+10+8+7+5, 28+15+12+10+8+7+6, 28+15+12+10+9+7+1, 28+15+12+10+9+7+2, 28+15+12+10+9+7+3, 28+15+12+10+9+7+4, 28+15+12+10+9+7+5, 28+15+12+10+9+7+6, 28+15+13+10+1, 28+15+13+10+2, 28+15+13+10+3, 28+15+13+10+4, 28+15+13+10+5, 28+15+13+10+6, 28+15+13+10+7+1, 28+15+13+10+7+2, 28+15+13+10+7+3, 28+15+13+10+7+4, 28+15+13+10+7+5, 28+15+13+10+7+6, 28+15+13+10+8+7+1, 28+15+13+10+8+7+2, 28+15+13+10+8+7+3, 28+15+13+10+8+7+4, 28+15+13+10+8+7+5, 28+15+13+10+8+7+6, 28+15+13+10+9+7+1, 28+15+13+10+9+7+2, 28+15+13+10+9+7+3, 28+15+13+10+9+7+4, 28+15+13+10+9+7+5, 28+15+13+10+9+7+6, 28+15+14+1, 28+15+14+2, 28+15+14+3, 28+15+14+4, 28+15+14+5, 28+15+14+6, 28+15+14+7+1, 28+15+14+7+2, 28+15+14+7+3, 28+15+14+7+4, 28+15+14+7+5, 28+15+14+7+6, 28+15+14+8+7+1, 28+15+14+8+7+2, 28+15+14+8+7+3, 28+15+14+8+7+4, 28+15+14+8+7+5, 28+15+14+8+7+6, 28+15+14+9+7+1, 28+15+14+9+7+2, 28+15+14+9+7+3, 28+15+14+9+7+4, 28+15+14+9+7+5, 28+15+14+9+7+6, 28+15+14+10+1, 28+15+14+10+2, 28+15+14+10+3, 28+15+14+10+4, 28+15+14+10+5, 28+15+14+10+6, 28+15+14+10+7+1, 28+15+14+10+7+2, 28+15+14+10+7+3, 28+15+14+10+7+4, 28+15+14+10+7+5, 28+15+14+10+7+6, 28+15+14+10+8+7+1, 28+15+14+10+8+7+2, 28+15+14+10+8+7+3, 28+15+14+10+8+7+4, 28+15+14+10+8+7+5, 28+15+14+10+8+7+6, 28+15+14+10+9+7+1, 28+15+14+10+9+7+2, 28+15+14+10+9+7+3, 28+15+14+10+9+7+4, 28+15+14+10+9+7+5, 28+15+14+10+9+7+6, 28+15+14+11+10+1, 28+15+14+11+10+2, 28+15+14+11+10+3, 28+15+14+11+10+4, 28+15+14+11+10+5, 28+15+14+11+10+6, 28+15+14+11+10+7+1, 28+15+14+11+10+7+2, 28+15+14+11+10+7+3, 28+15+14+11+10+7+4, 28+15+14+11+10+7+5, 28+15+14+11+10+7+6, 28+15+14+11+10+8+7+1, 28+15+14+11+10+8+7+2, 28+15+14+11+10+8+7+3, 28+15+14+11+10+8+7+4, 28+15+14+11+10+8+7+5, 28+15+14+11+10+8+7+6, 28+15+14+11+10+9+7+1, 28+15+14+11+10+9+7+2, 28+15+14+11+10+9+7+3, 28+15+14+11+10+9+7+4, 28+15+14+11+10+9+7+5, 28+15+14+11+10+9+7+6, 28+15+14+12+10+1, 28+15+14+12+10+2, 28+15+14+12+10+3, 28+15+14+12+10+4, 28+15+14+12+10+5, 28+15+14+12+10+6, 28+15+14+12+10+7+1, 28+15+14+12+10+7+2, 28+15+14+12+10+7+3, 28+15+14+12+10+7+4, 28+15+14+12+10+7+5, 28+15+14+12+10+7+6, 28+15+14+12+10+8+7+1, 28+15+14+12+10+8+7+2, 28+15+14+12+10+8+7+3, 28+15+14+12+10+8+7+4, 28+15+14+12+10+8+7+5, 28+15+14+12+10+8+7+6, 28+15+14+12+10+9+7+1, 28+15+14+12+10+9+7+2, 28+15+14+12+10+9+7+3, 28+15+14+12+10+9+7+4, 28+15+14+12+10+9+7+5, 28+15+14+12+10+9+7+6, 28+15+14+13+10+1, 28+15+14+13+10+2, 28+15+14+13+

10+3, 28+15+14+13+10+4, 28+15+14+13+10+5, 28+15+14+13+10+6, 28+15+14+13+10+7+1, 28+15+14+13+10+7+2, 28+15+14+13+10+7+3, 28+15+14+13+10+7+4, 28+15+14+13+10+7+5, 28+15+14+13+10+7+6, 28+15+14+13+10+8+7+1, 28+15+14+13+10+8+7+2, 28+15+14+13+10+8+7+3, 28+15+14+13+10+8+7+4, 28+15+14+13+10+8+7+5, 28+15+14+13+10+8+7+6, 28+15+14+13+10+9+7+1, 28+15+14+13+10+9+7+2, 28+15+14+13+10+9+7+3, 28+15+14+13+10+9+7+4, 28+15+14+13+10+9+7+5, 28+15+14+13+10+9+7+6, 28+16+1, 28+16+2, 28+16+3, 28+16+4, 28+16+5, 28+16+6, 28+16+7+1, 28+16+7+2, 28+16+7+3, 28+16+7+4, 28+16+7+5, 28+16+7+6, 28+16+8+7+1, 28+16+8+7+2, 28+16+8+7+3, 28+16+8+7+4, 28+16+8+7+5, 28+16+8+7+6, 28+16+9+7+1, 28+16+9+7+2, 28+16+9+7+3, 28+16+9+7+4, 28+16+9+7+5, 28+16+9+7+6, 28+16+10+1, 28+16+10+2, 28+16+10+3, 28+16+10+4, 28+16+10+5, 28+16+10+6, 28+16+10+7+1, 28+16+10+7+2, 28+16+10+7+3, 28+16+10+7+4, 28+16+10+7+5, 28+16+10+7+6, 28+16+10+8+7+1, 28+16+10+8+7+2, 28+16+10+8+7+3, 28+16+10+8+7+4, 28+16+10+8+7+5, 28+16+10+8+7+6, 28+16+10+9+7+1, 28+16+10+9+7+2, 28+16+10+9+7+3, 28+16+10+9+7+4, 28+16+10+9+7+5, 28+16+10+9+7+6, 28+16+11+10+1, 28+16+11+10+2, 28+16+11+10+3, 28+16+11+10+4, 28+16+11+10+5, 28+16+11+10+6, 28+16+11+10+7+1, 28+16+11+10+7+2, 28+16+11+10+7+3, 28+16+11+10+7+4, 28+16+11+10+7+5, 28+16+11+10+7+6, 28+16+11+10+8+7+1, 28+16+11+10+8+7+2, 28+16+11+10+8+7+3, 28+16+11+10+8+7+4, 28+16+11+10+8+7+5, 28+16+11+10+8+7+6, 28+16+11+10+9+7+1, 28+16+11+10+9+7+2, 28+16+11+10+9+7+3, 28+16+11+10+9+7+4, 28+16+11+10+9+7+5, 28+16+11+10+9+7+6, 28+16+12+10+1, 28+16+12+10+2, 28+16+12+10+3, 28+16+12+10+4, 28+16+12+10+5, 28+16+12+10+6, 28+16+12+10+7+1, 28+16+12+10+7+2, 28+16+12+10+7+3, 28+16+12+10+7+4, 28+16+12+10+7+5, 28+16+12+10+7+6, 28+16+12+10+8+7+1, 28+16+12+10+8+7+2, 28+16+12+10+8+7+3, 28+16+12+10+8+7+4, 28+16+12+10+8+7+5, 28+16+12+10+8+7+6, 28+16+12+10+9+7+1, 28+16+12+10+9+7+2, 28+16+12+10+9+7+3, 28+16+12+10+9+7+4, 28+16+12+10+9+7+5, 28+16+12+10+9+7+6, 28+16+13+10+1, 28+16+13+10+2, 28+16+13+10+3, 28+16+13+10+4, 28+16+13+10+5, 28+16+13+10+6, 28+16+13+10+7+1, 28+16+13+10+7+2, 28+16+13+10+7+3, 28+16+13+10+7+4, 28+16+13+10+7+5, 28+16+13+10+7+6, 28+16+13+10+8+7+1, 28+16+13+10+8+7+2, 28+16+13+10+8+7+3, 28+16+13+10+8+7+4, 28+16+13+10+8+7+5, 28+16+13+10+8+7+6, 28+16+13+10+9+7+1, 28+16+13+10+9+7+2, 28+16+13+10+9+7+3, 28+16+13+10+9+7+4, 28+16+13+10+9+7+5, 28+16+13+10+9+7+6, 28+16+14+1, 28+16+14+2, 28+16+14+3, 28+16+14+4, 28+16+14+5, 28+16+14+6, 28+16+14+7+1, 28+16+14+7+2, 28+16+14+7+3, 28+16+14+7+4, 28+16+14+7+5, 28+16+14+7+6, 28+16+14+8+7+1, 28+16+14+8+7+2, 28+16+14+8+7+3, 28+16+14+8+7+4, 28+16+14+8+7+5, 28+16+14+8+7+6, 28+16+14+9+7+1, 28+16+14+9+7+2, 28+16+14+9+7+3, 28+16+14+9+7+4, 28+16+14+9+7+5, 28+16+14+9+7+6, 28+16+14+10+1, 28+16+14+10+2, 28+16+14+10+3, 28+16+14+10+4, 28+16+14+10+5, 28+16+14+10+6, 28+16+14+10+7+1, 28+16+14+10+7+2, 28+16+14+10+7+3, 28+16+14+10+7+4, 28+16+14+10+7+5, 28+16+14+10+7+6, 28+16+14+10+8+7+1, 28+16+14+10+8+7+2, 28+16+14+10+8+7+3, 28+16+14+10+8+7+4, 28+16+14+10+8+7+5, 28+16+14+10+8+7+6, 28+16+14+10+9+7+1, 28+16+14+10+9+7+2, 28+16+14+10+9+7+3, 28+16+14+10+9+7+4, 28+16+14+10+9+7+5, 28+16+14+10+9+7+6, 28+16+14+11+10+1, 28+16+14+11+10+2, 28+16+14+11+10+3, 28+16+14+11+10+4, 28+16+14+11+10+5, 28+16+14+11+10+6, 28+16+14+11+10+7+1, 28+16+14+11+10+7+2, 28+16+14+11+10+7+3, 28+16+14+11+10+7+4, 28+16+14+11+10+7+5, 28+16+14+11+10+7+6, 28+16+14+11+10+8+7+1, 28+16+14+11+10+8+7+2, 28+16+14+11+10+8+7+3, 28+16+14+11+10+8+7+4, 28+16+14+11+10+8+7+5, 28+16+14+11+10+8+7+6, 28+16+14+11+10+9+7+1, 28+16+14+11+10+9+7+2, 28+16+14+11+10+9+7+3, 28+16+14+11+10+9+7+4, 28+16+14+11+10+9+7+5, 28+16+14+11+10+9+7+6, 28+16+14+12+10+1, 28+16+14+12+10+2, 28+16+14+12+10+3, 28+16+14+12+10+4, 28+16+14+12+10+5, 28+16+14+12+10+6, 28+16+14+12+10+7+1, 28+16+14+12+10+7+2, 28+16+14+12+10+7+3, 28+16+14+12+10+7+4, 28+16+14+12+10+7+5, 28+16+14+12+10+7+6, 28+16+14+12+10+8+7+1, 28+16+14+12+10+8+7+2, 28+16+14+12+10+8+7+3, 28+16+14+12+10+8+7+4, 28+16+14+12+10+8+7+5, 28+16+14+12+10+8+7+6, 28+16+14+12+10+9+7+1, 28+16+14+12+10+9+7+2, 28+16+14+12+10+9+7+3, 28+16+14+12+10+9+7+4, 28+16+14+12+10+9+7+5, 28+16+14+12+10+9+7+6, 28+16+14+13+10+1, 28+16+14+13+10+2, 28+16+14+13+10+3, 28+16+14+13+10+4, 28+16+14+13+10+5, 28+16+14+13+10+6, 28+16+14+13+10+7+1, 28+16+14+13+10+7+2, 28+16+14+13+10+7+3, 28+16+14+13+10+7+4, 28+16+14+13+10+7+5, 28+16+14+13+10+7+6, 28+16+14+13+10+8+7+1, 28+16+14+13+10+8+7+2, 28+16+14+13+10+8+7+3, 28+16+14+13+10+8+7+4, 28+16+14+13+10+8+7+5, 28+16+14+13+10+8+7+6, 28+16+14+13+10+9+7+1, 28+16+14+13+10+9+7+2, 28+16+14+13+10+9+7+3, 28+16+14+13+10+9+7+4, 28+16+14+13+10+9+7+5, 28+16+14+13+10+9+7+6, 28+17+1, 28+17+2, 28+17+3, 28+18+17+1, 28+18+17+2, 28+18+17+3, 28+19+4, 28+19+5, 28+19+6, 28+20+1, 28+20+2, 28+20+3, 28+21+20+1, 28+21+20+2, 28+21+20+3, 28+22+20+1, 28+22+20+2, 28+22+20+3, 28+23+20+1, 28+23+20+2, 28+23+20+3, 28+24+4, 28+24+5, 28+24+6, 28+25+4, 28+25+5, 28+25+6, 28+26+4, 28+26+5, 28+26+6, 29+1, 29+2, 29+3, 36+2, 36+3, 36+4, 36+5, 36+6, 36+7+1, 36+7+2, 36+7+3, 36+7+4, 36+7+5, 36+7+6, 36+8+7+1, 36+8+7+2, 36+8+7+3, 36+8+7+4, 36+8+7+5, 36+8+7+6, 36+9+7+1, 36+9+7+2, 36+9+7+3, 36+9+7+4, 36+9+7+5, 36+9+7+6, 36+10+1, 36+10+2, 36+10+3, 36+10+4, 36+10+5, 36+10+6, 36+10+7+1, 36+10+7+2, 36+10+7+3, 36+10+7+4, 36+10+7+5, 36+10+7+6, 36+10+8+7+1, 36+10+8+7+2, 36+10+8+7+3, 36+10+8+7+4, 36+10+8+7+5, 36+10+8+7+6, 36+10+9+7+1, 36+10+9+7+2, 36+10+9+7+3, 36+10+9+7+4, 36+10+9+7+5, 36+10+9+7+6, 36+11+10+1, 36+11+10+2, 36+11+10+3, 36+11+10+4, 36+11+10+5, 36+11+10+6, 36+11+10+7+1, 36+11+10+7+2, 36+11+10+7+3, 36+11+10+7+4, 36+11+10+7+5, 36+11+10+7+6, 36+11+10+8+7+1, 36+11+10+8+7+2, 36+11+10+8+7+3, 36+11+10+8+7+4, 36+11+10+8+7+5, 36+11+10+8+7+6, 36+11+10+9+7+1, 36+11+10+9+7+2, 36+11+10+9+7+3, 36+11+10+9+7+4, 36+11+10+9+7+5, 36+11+10+9+7+6, 36+12+10+1, 36+12+10+2, 36+12+10+3, 36+12+10+4, 36+12+10+5, 36+12+10+6, 36+12+10+7+1, 36+12+10+7+2, 36+12+10+7+3, 36+12+10+7+4, 36+12+10+7+5, 36+12+10+7+6, 36+12+10+8+7+1, 36+12+10+8+7+2, 36+12+10+8+7+3, 36+12+10+8+7+4, 36+12+10+8+7+5, 36+12+10+8+7+6, 36+12+10+9+7+1, 36+12+10+9+7+2, 36+12+10+9+7+3, 36+12+10+9+7+4, 36+12+10+9+7+5, 36+12+10+9+7+6, 36+13+10+1, 36+13+10+2, 36+13+10+3, 36+13+10+4, 36+13+10+5, 36+13+10+6, 36+13+10+7+1, 36+13+10+7+2, 36+13+10+7+3, 36+13+10+7+4, 36+13+10+7+5, 36+13+10+7+6, 36+13+10+8+7+

1, 36+13+10+8+7+2, 36+13+10+8+7+3, 36+13+10+8+7+4, 36+13+10+8+7+5, 36+13+10+8+7+6, 36+13+10+9+7+1, 36+13+10+9+7+2, 36+13+10+9+7+3, 36+13+10+9+7+4, 36+13+10+9+7+5, 36+13+10+9+7+6, 36+14+1, 36+14+2, 36+14+3, 36+14+4, 36+14+5, 36+14+6, 36+14+7+1, 36+14+7+2, 36+14+7+3, 36+14+7+4, 36+14+7+5, 36+14+7+6, 36+14+8+7+1, 36+14+8+7+2, 36+14+8+7+3, 36+14+8+7+4, 36+14+8+7+5, 36+14+8+7+6, 36+14+9+7+1, 36+14+9+7+2, 36+14+9+7+3, 36+14+9+7+4, 36+14+9+7+5, 36+14+9+7+6, 36+14+10+1, 36+14+10+2, 36+14+10+3, 36+14+10+4, 36+14+10+5, 36+14+10+6, 36+14+10+7+1, 36+14+10+7+2, 36+14+10+7+3, 36+14+10+7+4, 36+14+10+7+5, 36+14+10+7+6, 36+14+10+8+7+1, 36+14+10+8+7+2, 36+14+10+8+7+3, 36+14+10+8+7+4, 36+14+10+8+7+5, 36+14+10+8+7+6, 36+14+10+9+7+1, 36+14+10+9+7+2, 36+14+10+9+7+3, 36+14+10+9+7+4, 36+14+10+9+7+5, 36+14+10+9+7+6, 36+14+11+10+1, 36+14+11+10+2, 36+14+11+10+3, 36+14+11+10+4, 36+14+11+10+5, 36+14+11+10+6, 36+14+11+10+7+1, 36+14+11+10+7+2, 36+14+11+10+7+3, 36+14+11+10+7+4, 36+14+11+10+7+5, 36+14+11+10+7+6, 36+14+11+10+8+7+1, 36+14+11+10+8+7+2, 36+14+11+10+8+7+3, 36+14+11+10+8+7+4, 36+14+11+10+8+7+5, 36+14+11+10+8+7+6, 36+14+11+10+9+7+1, 36+14+11+10+9+7+2, 36+14+11+10+9+7+3, 36+14+11+10+9+7+4, 36+14+11+10+9+7+5, 36+14+11+10+9+7+6, 36+14+12+10+1, 36+14+12+10+2, 36+14+12+10+3, 36+14+12+10+4, 36+14+12+10+5, 36+14+12+10+6, 36+14+12+10+7+1, 36+14+12+10+7+2, 36+14+12+10+7+3, 36+14+12+10+7+4, 36+14+12+10+7+5, 36+14+12+10+7+6, 36+14+12+10+8+7+1, 36+14+12+10+8+7+2, 36+14+12+10+8+7+3, 36+14+12+10+8+7+4, 36+14+12+10+8+7+5, 36+14+12+10+8+7+6, 36+14+12+10+9+7+1, 36+14+12+10+9+7+2, 36+14+12+10+9+7+3, 36+14+12+10+9+7+4, 36+14+12+10+9+7+5, 36+14+12+10+9+7+6, 36+14+13+10+1, 36+14+13+10+2, 36+14+13+10+3, 36+14+13+10+4, 36+14+13+10+5, 36+14+13+10+6, 36+14+13+10+7+1, 36+14+13+10+7+2, 36+14+13+10+7+3, 36+14+13+10+7+4, 36+14+13+10+7+5, 36+14+13+10+7+6, 36+14+13+10+8+7+1, 36+14+13+10+8+7+2, 36+14+13+10+8+7+3, 36+14+13+10+8+7+4, 36+14+13+10+8+7+5, 36+14+13+10+8+7+6, 36+14+13+10+9+7+1, 36+14+13+10+9+7+2, 36+14+13+10+9+7+3, 36+14+13+10+9+7+4, 36+14+13+10+9+7+5, 36+14+13+10+9+7+6, 36+15+1, 36+15+2, 36+15+3, 36+15+4, 36+15+5, 36+15+6, 36+15+7+1, 36+15+7+2, 36+15+7+3, 36+15+7+4, 36+15+7+5, 36+15+7+6, 36+15+8+7+1, 36+15+8+7+2, 36+15+8+7+3, 36+15+8+7+4, 36+15+8+7+5, 36+15+8+7+6, 36+15+9+7+1, 36+15+9+7+2, 36+15+9+7+3, 36+15+9+7+4, 36+15+9+7+5, 36+15+9+7+6, 36+15+10+1, 36+15+10+2, 36+15+10+3, 36+15+10+4, 36+15+10+5, 36+15+10+6, 36+15+10+7+1, 36+15+10+7+2, 36+15+10+7+3, 36+15+10+7+4, 36+15+10+7+5, 36+15+10+7+6, 36+15+10+8+7+1, 36+15+10+8+7+2, 36+15+10+8+7+3, 36+15+10+8+7+4, 36+15+10+8+7+5, 36+15+10+8+7+6, 36+15+10+9+7+1, 36+15+10+9+7+2, 36+15+10+9+7+3, 36+15+10+9+7+4, 36+15+10+9+7+5, 36+15+10+9+7+6, 36+15+11+10+1, 36+15+11+10+2, 36+15+11+10+3, 36+15+11+10+4, 36+15+11+10+5, 36+15+11+10+6, 36+15+11+10+7+1, 36+15+11+10+7+2, 36+15+11+10+7+3, 36+15+11+10+7+4, 36+15+11+10+7+5, 36+15+11+10+7+6, 36+15+11+10+8+7+1, 36+15+11+10+8+7+2, 36+15+11+10+8+7+3, 36+15+11+10+8+7+4, 36+15+11+10+8+7+5, 36+15+11+10+8+7+6, 36+15+11+10+9+7+1, 36+15+11+10+9+7+2, 36+15+11+10+9+7+3, 36+15+11+10+9+7+4, 36+15+11+10+9+7+5, 36+15+11+10+9+7+6, 36+15+12+10+1, 36+15+12+10+2, 36+15+12+10+3, 36+15+12+10+4, 36+15+12+10+5, 36+15+12+10+6, 36+15+12+10+7+1, 36+15+12+10+7+2, 36+15+12+10+7+3, 36+15+12+10+7+4, 36+15+12+10+7+5, 36+15+12+10+7+6, 36+15+12+10+8+7+1, 36+15+12+10+8+7+2, 36+15+12+10+8+7+3, 36+15+12+10+8+7+4, 36+15+12+10+8+7+5, 36+15+12+10+8+7+6, 36+15+12+10+9+7+1, 36+15+12+10+9+7+2, 36+15+12+10+9+7+3, 36+15+12+10+9+7+4, 36+15+12+10+9+7+5, 36+15+12+10+9+7+6, 36+15+13+10+1, 36+15+13+10+2, 36+15+13+10+3, 36+15+13+10+4, 36+15+13+10+5, 36+15+13+10+6, 36+15+13+10+7+1, 36+15+13+10+7+2, 36+15+13+10+7+3, 36+15+13+10+7+4, 36+15+13+10+7+5, 36+15+13+10+7+6, 36+15+13+10+8+7+1, 36+15+13+10+8+7+2, 36+15+13+10+8+7+3, 36+15+13+10+8+7+4, 36+15+13+10+8+7+5, 36+15+13+10+8+7+6, 36+15+13+10+9+7+1, 36+15+13+10+9+7+2, 36+15+13+10+9+7+3, 36+15+13+10+9+7+4, 36+15+13+10+9+7+5, 36+15+13+10+9+7+6, 36+15+14+1, 36+15+14+2, 36+15+14+3, 36+15+14+4, 36+15+14+5, 36+15+14+6, 36+15+14+7+1, 36+15+14+7+2, 36+15+14+7+3, 36+15+14+7+4, 36+15+14+7+5, 36+15+14+7+6, 36+15+14+8+7+1, 36+15+14+8+7+2, 36+15+14+8+7+3, 36+15+14+8+7+4, 36+15+14+8+7+5, 36+15+14+8+7+6, 36+15+14+9+7+1, 36+15+14+9+7+2, 36+15+14+9+7+3, 36+15+14+9+7+4, 36+15+14+9+7+5, 36+15+14+9+7+6, 36+15+14+10+1, 36+15+14+10+2, 36+15+14+10+3, 36+15+14+10+4, 36+15+14+10+5, 36+15+14+10+6, 36+15+14+10+7+1, 36+15+14+10+7+2, 36+15+14+10+7+3, 36+15+14+10+7+4, 36+15+14+10+7+5, 36+15+14+10+7+6, 36+15+14+10+8+7+1, 36+15+14+10+8+7+2, 36+15+14+10+8+7+3, 36+15+14+10+8+7+4, 36+15+14+10+8+7+5, 36+15+14+10+8+7+6, 36+15+14+10+9+7+1, 36+15+14+10+9+7+2, 36+15+14+10+9+7+3, 36+15+14+10+9+7+4, 36+15+14+10+9+7+5, 36+15+14+10+9+7+6, 36+15+14+11+10+1, 36+15+14+11+10+2, 36+15+14+11+10+3, 36+15+14+11+10+4, 36+15+14+11+10+5, 36+15+14+11+10+6, 36+15+14+11+10+7+1, 36+15+14+11+10+7+2, 36+15+14+11+10+7+3, 36+15+14+11+10+7+4, 36+15+14+11+10+7+5, 36+15+14+11+10+7+6, 36+15+14+11+10+8+7+1, 36+15+14+11+10+8+7+2, 36+15+14+11+10+8+7+3, 36+15+14+11+10+8+7+4, 36+15+14+11+10+8+7+5, 36+15+14+11+10+8+7+6, 36+15+14+11+10+9+7+1, 36+15+14+11+10+9+7+2, 36+15+14+11+10+9+7+3, 36+15+14+11+10+9+7+4, 36+15+14+11+10+9+7+5, 36+15+14+11+10+9+7+6, 36+15+14+12+10+1, 36+15+14+12+10+2, 36+15+14+12+10+3, 36+15+14+12+10+4, 36+15+14+12+10+5, 36+15+14+12+10+6, 36+15+14+12+10+7+1, 36+15+14+12+10+7+2, 36+15+14+12+10+7+3, 36+15+14+12+10+7+4, 36+15+14+12+10+7+5, 36+15+14+12+10+7+6, 36+15+14+12+10+8+7+1, 36+15+14+12+10+8+7+2, 36+15+14+12+10+8+7+3, 36+15+14+12+10+8+7+4, 36+15+14+12+10+8+7+5, 36+15+14+12+10+8+7+6, 36+15+14+12+10+9+7+1, 36+15+14+12+10+9+7+2, 36+15+14+12+10+9+7+3, 36+15+14+12+10+9+7+4, 36+15+14+12+10+9+7+5, 36+15+14+12+10+9+7+6, 36+15+14+13+10+1, 36+15+14+13+10+2, 36+15+14+13+10+3, 36+15+14+13+10+4, 36+15+14+13+10+5, 36+15+14+13+10+6, 36+15+14+13+10+7+1, 36+15+14+13+10+7+2, 36+15+14+13+10+7+3, 36+15+14+13+10+7+4, 36+15+14+13+10+7+5, 36+15+14+13+10+7+6, 36+15+14+13+10+8+7+1, 36+15+14+13+10+8+7+2, 36+15+14+13+10+8+7+3, 36+15+14+13+10+8+7+4, 36+15+14+13+10+8+7+5, 36+15+14+13+10+8+7+6, 36+15+14+13+10+9+7+1,

36+15+14+13+10+9+7+2, 36+15+14+13+10+9+7+3, 36+15+14+13+10+9+7+4, 36+15+14+13+10+9+7+5, 36+15+14+13+10+9+7+6, 36+16+1, 36+16+2, 36+16+3, 36+16+4, 36+16+5, 36+16+6, 36+16+7+1, 36+16+7+2, 36+16+7+3, 36+16+7+4, 36+16+7+5, 36+16+7+6, 36+16+8+7+1, 36+16+8+7+2, 36+16+8+7+3, 36+16+8+7+4, 36+16+8+7+5, 36+16+8+7+6, 36+16+9+7+1, 36+16+9+7+2, 36+16+9+7+3, 36+16+9+7+4, 36+16+9+7+5, 36+16+9+7+6, 36+16+10+1, 36+16+10+2, 36+16+10+3, 36+16+10+4, 36+16+10+5, 36+16+10+6, 36+16+10+7+1, 36+16+10+7+2, 36+16+10+7+3, 36+16+10+7+4, 36+16+10+7+5, 36+16+10+7+6, 36+16+10+8+7+1, 36+16+10+8+7+2, 36+16+10+8+7+3, 36+16+10+8+7+4, 36+16+10+8+7+5, 36+16+10+8+7+6, 36+16+10+9+7+1, 36+16+10+9+7+2, 36+16+10+9+7+3, 36+16+10+9+7+4, 36+16+10+9+7+5, 36+16+10+9+7+6, 36+16+11+10+1, 36+16+11+10+2, 36+16+11+10+3, 36+16+11+10+4, 36+16+11+10+5, 36+16+11+10+6, 36+16+11+10+7+1, 36+16+11+10+7+2, 36+16+11+10+7+3, 36+16+11+10+7+4, 36+16+11+10+7+5, 36+16+11+10+7+6, 36+16+11+10+8+7+1, 36+16+11+10+8+7+2, 36+16+11+10+8+7+3, 36+16+11+10+8+7+4, 36+16+11+10+8+7+5, 36+16+11+10+8+7+6, 36+16+11+10+9+7+1, 36+16+11+10+9+7+2, 36+16+11+10+9+7+3, 36+16+11+10+9+7+4, 36+16+11+10+9+7+5, 36+16+11+10+9+7+6, 36+16+12+10+1, 36+16+12+10+2, 36+16+12+10+3, 36+16+12+10+4, 36+16+12+10+5, 36+16+12+10+6, 36+16+12+10+7+1, 36+16+12+10+7+2, 36+16+12+10+7+3, 36+16+12+10+7+4, 36+16+12+10+7+5, 36+16+12+10+7+6, 36+16+12+10+8+7+1, 36+16+12+10+8+7+2, 36+16+12+10+8+7+3, 36+16+12+10+8+7+4, 36+16+12+10+8+7+5, 36+16+12+10+8+7+6, 36+16+12+10+9+7+1, 36+16+12+10+9+7+2, 36+16+12+10+9+7+3, 36+16+12+10+9+7+4, 36+16+12+10+9+7+5, 36+16+12+10+9+7+6, 36+16+13+10+1, 36+16+13+10+2, 36+16+13+10+3, 36+16+13+10+4, 36+16+13+10+5, 36+16+13+10+6, 36+16+13+10+7+1, 36+16+13+10+7+2, 36+16+13+10+7+3, 36+16+13+10+7+4, 36+16+13+10+7+5, 36+16+13+10+7+6, 36+16+13+10+8+7+1, 36+16+13+10+8+7+2, 36+16+13+10+8+7+3, 36+16+13+10+8+7+4, 36+16+13+10+8+7+5, 36+16+13+10+8+7+6, 36+16+13+10+9+7+1, 36+16+13+10+9+7+2, 36+16+13+10+9+7+3, 36+16+13+10+9+7+4, 36+16+13+10+9+7+5, 36+16+13+10+9+7+6, 36+16+14+1, 36+16+14+2, 36+16+14+3, 36+16+14+4, 36+16+14+5, 36+16+14+6, 36+16+14+7+1, 36+16+14+7+2, 36+16+14+7+3, 36+16+14+7+4, 36+16+14+7+5, 36+16+14+7+6, 36+16+14+8+7+1, 36+16+14+8+7+2, 36+16+14+8+7+3, 36+16+14+8+7+4, 36+16+14+8+7+5, 36+16+14+8+7+6, 36+16+14+9+7+1, 36+16+14+9+7+2, 36+16+14+9+7+3, 36+16+14+9+7+4, 36+16+14+9+7+5, 36+16+14+9+7+6, 36+16+14+10+1, 36+16+14+10+2, 36+16+14+10+3, 36+16+14+10+4, 36+16+14+10+5, 36+16+14+10+6, 36+16+14+10+7+1, 36+16+14+10+7+2, 36+16+14+10+7+3, 36+16+14+10+7+4, 36+16+14+10+7+5, 36+16+14+10+7+6, 36+16+14+10+8+7+1, 36+16+14+10+8+7+2, 36+16+14+10+8+7+3, 36+16+14+10+8+7+4, 36+16+14+10+8+7+5, 36+16+14+10+8+7+6, 36+16+14+10+9+7+1, 36+16+14+10+9+7+2, 36+16+14+10+9+7+3, 36+16+14+10+9+7+4, 36+16+14+10+9+7+5, 36+16+14+10+9+7+6, 36+16+14+11+10+1, 36+16+14+11+10+2, 36+16+14+11+10+3, 36+16+14+11+10+4, 36+16+14+11+10+5, 36+16+14+11+10+6, 36+16+14+11+10+7+1, 36+16+14+11+10+7+2, 36+16+14+11+10+7+3, 36+16+14+11+10+7+4, 36+16+14+11+10+7+5, 36+16+14+11+10+7+6, 36+16+14+11+10+8+7+1, 36+16+14+11+10+8+7+2, 36+16+14+11+10+8+7+3, 36+16+14+11+10+8+7+4, 36+16+14+11+10+8+7+5, 36+16+14+11+10+8+7+6, 36+16+14+11+10+9+7+1, 36+16+14+11+10+9+7+2, 36+16+14+11+10+9+7+3, 36+16+14+11+10+9+7+4, 36+16+14+11+10+9+7+5, 36+16+14+11+10+9+7+6, 36+16+14+12+10+1, 36+16+14+12+10+2, 36+16+14+12+10+3, 36+16+14+12+10+4, 36+16+14+12+10+5, 36+16+14+12+10+6, 36+16+14+12+10+7+1, 36+16+14+12+10+7+2, 36+16+14+12+10+7+3, 36+16+14+12+10+7+4, 36+16+14+12+10+7+5, 36+16+14+12+10+7+6, 36+16+14+12+10+8+7+1, 36+16+14+12+10+8+7+2, 36+16+14+12+10+8+7+3, 36+16+14+12+10+8+7+4, 36+16+14+12+10+8+7+5, 36+16+14+12+10+8+7+6, 36+16+14+12+10+9+7+1, 36+16+14+12+10+9+7+2, 36+16+14+12+10+9+7+3, 36+16+14+12+10+9+7+4, 36+16+14+12+10+9+7+5, 36+16+14+12+10+9+7+6, 36+16+14+13+10+1, 36+16+14+13+10+2, 36+16+14+13+10+3, 36+16+14+13+10+4, 36+16+14+13+10+5, 36+16+14+13+10+6, 36+16+14+13+10+7+1, 36+16+14+13+10+7+2, 36+16+14+13+10+7+3, 36+16+14+13+10+7+4, 36+16+14+13+10+7+5, 36+16+14+13+10+7+6, 36+16+14+13+10+8+7+1, 36+16+14+13+10+8+7+2, 36+16+14+13+10+8+7+3, 36+16+14+13+10+8+7+4, 36+16+14+13+10+8+7+5, 36+16+14+13+10+8+7+6, 36+16+14+13+10+9+7+1, 36+16+14+13+10+9+7+2, 36+16+14+13+10+9+7+3, 36+16+14+13+10+9+7+4, 36+16+14+13+10+9+7+5, 36+16+14+13+10+9+7+6, 36+17+1, 36+17+2, 36+17+3, 36+18+17+1, 36+18+17+2, 36+18+17+3, 36+19+4, 36+19+5, 36+19+6, 36+20+1, 36+20+2, 36+20+3, 36+21+20+1, 36+21+20+2, 36+21+20+3, 36+22+20+1, 36+22+20+2, 36+22+20+3, 36+23+20+1, 36+23+20+2, 36+23+20+3, 36+24+4, 36+24+5, 36+24+6, 36+25+4, 36+25+5, 36+25+6, 36+26+4, 36+26+5, 36+26+6, 36+27+1, 36+27+2, 36+27+3, 36+27+4, 36+27+5, 36+27+6, 36+27+7+1, 36+27+7+2, 36+27+7+3, 36+27+7+4, 36+27+7+5, 36+27+7+6, 36+27+8+7+1, 36+27+8+7+2, 36+27+8+7+3, 36+27+8+7+4, 36+27+8+7+5, 36+27+8+7+6, 36+27+9+7+1, 36+27+9+7+2, 36+27+9+7+3, 36+27+9+7+4, 36+27+9+7+5, 36+27+9+7+6, 36+27+10+1, 36+27+10+2, 36+27+10+3, 36+27+10+4, 36+27+10+5, 36+27+10+6, 36+27+10+7+1, 36+27+10+7+2, 36+27+10+7+3, 36+27+10+7+4, 36+27+10+7+5, 36+27+10+7+6, 36+27+10+8+7+1, 36+27+10+8+7+2, 36+27+10+8+7+3, 36+27+10+8+7+4, 36+27+10+8+7+5, 36+27+10+8+7+6, 36+27+10+9+7+1, 36+27+10+9+7+2, 36+27+10+9+7+3, 36+27+10+9+7+4, 36+27+10+9+7+5, 36+27+10+9+7+6, 36+27+11+10+1, 36+27+11+10+2, 36+27+11+10+3, 36+27+11+10+4, 36+27+11+10+5, 36+27+11+10+6, 36+27+11+10+7+1, 36+27+11+10+7+2, 36+27+11+10+7+3, 36+27+11+10+7+4, 36+27+11+10+7+5, 36+27+11+10+7+6, 36+27+11+10+8+7+1, 36+27+11+10+8+7+2, 36+27+11+10+8+7+3, 36+27+11+10+8+7+4, 36+27+11+10+8+7+5, 36+27+11+10+8+7+6, 36+27+11+10+9+7+1, 36+27+11+10+9+7+2, 36+27+11+10+9+7+3, 36+27+11+10+9+7+4, 36+27+11+10+9+7+5, 36+27+11+10+9+7+6, 36+27+12+10+1, 36+27+12+10+2, 36+27+12+10+3, 36+27+12+10+4, 36+27+12+10+5, 36+27+12+10+6, 36+27+12+10+7+1, 36+27+12+10+7+2, 36+27+12+10+7+3, 36+27+12+10+7+4, 36+27+12+10+7+5, 36+27+12+10+7+6, 36+27+12+10+8+7+1, 36+27+12+10+8+7+2, 36+27+12+10+8+7+3, 36+27+12+10+8+7+4, 36+27+12+10+8+7+5, 36+27+12+10+8+7+6, 36+27+12+10+9+7+1, 36+27+12+10+9+7+2, 36+27+12+10+9+7+3, 36+27+12+10+9+7+4, 36+27+12+10+9+7+5, 36+27+12+10+9+7+6, 36+27+13+10+1, 36+27+13+10+2, 36+27+13+10+3, 36+27+13+10+4, 36+27+13+10+5, 36+27+13+10+6, 36+27+13+10+7+1, 36+27+13+10+7+2, 36+27+13+10+7+3, 36+27+13+10+7+4, 36+27+13+10+7+5, 36+27+13+10+7+6, 36+27+13+10+8+7+1, 36+27+13+10+8+7+2, 36+27+

13+10+8+7+3, 36+27+13+10+8+7+4, 36+27+13+10+8+7+5, 36+27+13+10+8+7+6, 36+27+13+10+9+7+1, 36+27+13+10+9+7+2, 36+27+13+10+9+7+3, 36+27+13+10+9+7+4, 36+27+13+10+9+7+5, 36+27+13+10+9+7+6, 36+27+14+1, 36+27+14+2, 36+27+14+3, 36+27+14+4, 36+27+14+5, 36+27+14+6, 36+27+14+7+1, 36+27+14+7+2, 36+27+14+7+3, 36+27+14+7+4, 36+27+14+7+5, 36+27+14+7+6, 36+27+14+8+7+1, 36+27+14+8+7+2, 36+27+14+8+7+3, 36+27+14+8+7+4, 36+27+14+8+7+5, 36+27+14+8+7+6, 36+27+14+9+7+1, 36+27+14+9+7+2, 36+27+14+9+7+3, 36+27+14+9+7+4, 36+27+14+9+7+5, 36+27+14+9+7+6, 36+27+14+10+1, 36+27+14+10+2, 36+27+14+10+3, 36+27+14+10+4, 36+27+14+10+5, 36+27+14+10+6, 36+27+14+10+7+1, 36+27+14+10+7+2, 36+27+14+10+7+3, 36+27+14+10+7+4, 36+27+14+10+7+5, 36+27+14+10+7+6, 36+27+14+10+8+7+1, 36+27+14+10+8+7+2, 36+27+14+10+8+7+3, 36+27+14+10+8+7+4, 36+27+14+10+8+7+5, 36+27+14+10+8+7+6, 36+27+14+10+9+7+1, 36+27+14+10+9+7+2, 36+27+14+10+9+7+3, 36+27+14+10+9+7+4, 36+27+14+10+9+7+5, 36+27+14+10+9+7+6, 36+27+14+11+10+1, 36+27+14+11+10+2, 36+27+14+11+10+3, 36+27+14+11+10+4, 36+27+14+11+10+5, 36+27+14+11+10+6, 36+27+14+11+10+7+1, 36+27+14+11+10+7+2, 36+27+14+11+10+7+3, 36+27+14+11+10+7+4, 36+27+14+11+10+7+5, 36+27+14+11+10+7+6, 36+27+14+11+10+8+7+1, 36+27+14+11+10+8+7+2, 36+27+14+11+10+8+7+3, 36+27+14+11+10+8+7+4, 36+27+14+11+10+8+7+5, 36+27+14+11+10+8+7+6, 36+27+14+11+10+9+7+1, 36+27+14+11+10+9+7+2, 36+27+14+11+10+9+7+3, 36+27+14+11+10+9+7+4, 36+27+14+11+10+9+7+5, 36+27+14+11+10+9+7+6, 36+27+14+12+10+1, 36+27+14+12+10+2, 36+27+14+12+10+3, 36+27+14+12+10+4, 36+27+14+12+10+5, 36+27+14+12+10+6, 36+27+14+12+10+7+1, 36+27+14+12+10+7+2, 36+27+14+12+10+7+3, 36+27+14+12+10+7+4, 36+27+14+12+10+7+5, 36+27+14+12+10+7+6, 36+27+14+12+10+8+7+1, 36+27+14+12+10+8+7+2, 36+27+14+12+10+8+7+3, 36+27+14+12+10+8+7+4, 36+27+14+12+10+8+7+5, 36+27+14+12+10+8+7+6, 36+27+14+12+10+9+7+1, 36+27+14+12+10+9+7+2, 36+27+14+12+10+9+7+3, 36+27+14+12+10+9+7+4, 36+27+14+12+10+9+7+5, 36+27+14+12+10+9+7+6, 36+27+14+13+10+1, 36+27+14+13+10+2, 36+27+14+13+10+3, 36+27+14+13+10+4, 36+27+14+13+10+5, 36+27+14+13+10+6, 36+27+14+13+10+7+1, 36+27+14+13+10+7+2, 36+27+14+13+10+7+3, 36+27+14+13+10+7+4, 36+27+14+13+10+7+5, 36+27+14+13+10+7+6, 36+27+14+13+10+8+7+1, 36+27+14+13+10+8+7+2, 36+27+14+13+10+8+7+3, 36+27+14+13+10+8+7+4, 36+27+14+13+10+8+7+5, 36+27+14+13+10+8+7+6, 36+27+14+13+10+9+7+1, 36+27+14+13+10+9+7+2, 36+27+14+13+10+9+7+3, 36+27+14+13+10+9+7+4, 36+27+14+13+10+9+7+5, 36+27+14+13+10+9+7+6, 36+27+15+1, 36+27+15+2, 36+27+15+3, 36+27+15+4, 36+27+15+5, 36+27+15+6, 36+27+15+7+1, 36+27+15+7+2, 36+27+15+7+3, 36+27+15+7+4, 36+27+15+7+5, 36+27+15+7+6, 36+27+15+8+7+1, 36+27+15+8+7+2, 36+27+15+8+7+3, 36+27+15+8+7+4, 36+27+15+8+7+5, 36+27+15+8+7+6, 36+27+15+9+7+1, 36+27+15+9+7+2, 36+27+15+9+7+3, 36+27+15+9+7+4, 36+27+15+9+7+5, 36+27+15+9+7+6, 36+27+15+10+1, 36+27+15+10+2, 36+27+15+10+3, 36+27+15+10+4, 36+27+15+10+5, 36+27+15+10+6, 36+27+15+10+7+1, 36+27+15+10+7+2, 36+27+15+10+7+3, 36+27+15+10+7+4, 36+27+15+10+7+5, 36+27+15+10+7+6, 36+27+15+10+8+7+1, 36+27+15+10+8+7+2, 36+27+15+10+8+7+3, 36+27+15+10+8+7+4, 36+27+15+10+8+7+5, 36+27+15+10+8+7+6, 36+27+15+10+9+7+1, 36+27+15+10+9+7+2, 36+27+15+10+9+7+3, 36+27+15+10+9+7+4, 36+27+15+10+9+7+5, 36+27+15+10+9+7+6, 36+27+15+11+10+1, 36+27+15+11+10+2, 36+27+15+11+10+3, 36+27+15+11+10+4, 36+27+15+11+10+5, 36+27+15+11+10+6, 36+27+15+11+10+7+1, 36+27+15+11+10+7+2, 36+27+15+11+10+7+3, 36+27+15+11+10+7+4, 36+27+15+11+10+7+5, 36+27+15+11+10+7+6, 36+27+15+11+10+8+7+1, 36+27+15+11+10+8+7+2, 36+27+15+11+10+8+7+3, 36+27+15+11+10+8+7+4, 36+27+15+11+10+8+7+5, 36+27+15+11+10+8+7+6, 36+27+15+11+10+9+7+1, 36+27+15+11+10+9+7+2, 36+27+15+11+10+9+7+3, 36+27+15+11+10+9+7+4, 36+27+15+11+10+9+7+5, 36+27+15+11+10+9+7+6, 36+27+15+12+10+1, 36+27+15+12+10+2, 36+27+15+12+10+3, 36+27+15+12+10+4, 36+27+15+12+10+5, 36+27+15+12+10+6, 36+27+15+12+10+7+1, 36+27+15+12+10+7+2, 36+27+15+12+10+7+3, 36+27+15+12+10+7+4, 36+27+15+12+10+7+5, 36+27+15+12+10+7+6, 36+27+15+12+10+8+7+1, 36+27+15+12+10+8+7+2, 36+27+15+12+10+8+7+3, 36+27+15+12+10+8+7+4, 36+27+15+12+10+8+7+5, 36+27+15+12+10+8+7+6, 36+27+15+12+10+9+7+1, 36+27+15+12+10+9+7+2, 36+27+15+12+10+9+7+3, 36+27+15+12+10+9+7+4, 36+27+15+12+10+9+7+5, 36+27+15+12+10+9+7+6, 36+27+15+13+10+1, 36+27+15+13+10+2, 36+27+15+13+10+3, 36+27+15+13+10+4, 36+27+15+13+10+5, 36+27+15+13+10+6, 36+27+15+13+10+7+1, 36+27+15+13+10+7+2, 36+27+15+13+10+7+3, 36+27+15+13+10+7+4, 36+27+15+13+10+7+5, 36+27+15+13+10+7+6, 36+27+15+13+10+8+7+1, 36+27+15+13+10+8+7+2, 36+27+15+13+10+8+7+3, 36+27+15+13+10+8+7+4, 36+27+15+13+10+8+7+5, 36+27+15+13+10+8+7+6, 36+27+15+13+10+9+7+1, 36+27+15+13+10+9+7+2, 36+27+15+13+10+9+7+3, 36+27+15+13+10+9+7+4, 36+27+15+13+10+9+7+5, 36+27+15+13+10+9+7+6, 36+27+15+14+1, 36+27+15+14+2, 36+27+15+14+3, 36+27+15+14+4, 36+27+15+14+5, 36+27+15+14+6, 36+27+15+14+7+1, 36+27+15+14+7+2, 36+27+15+14+7+3, 36+27+15+14+7+4, 36+27+15+14+7+5, 36+27+15+14+7+6, 36+27+15+14+8+7+1, 36+27+15+14+8+7+2, 36+27+15+14+8+7+3, 36+27+15+14+8+7+4, 36+27+15+14+8+7+5, 36+27+15+14+8+7+6, 36+27+15+14+9+7+1, 36+27+15+14+9+7+2, 36+27+15+14+9+7+3, 36+27+15+14+9+7+4, 36+27+15+14+9+7+5, 36+27+15+14+9+7+6, 36+27+15+14+10+1, 36+27+15+14+10+2, 36+27+15+14+10+3, 36+27+15+14+10+4, 36+27+15+14+10+5, 36+27+15+14+10+6, 36+27+15+14+10+7+1, 36+27+15+14+10+7+2, 36+27+15+14+10+7+3, 36+27+15+14+10+7+4, 36+27+15+14+10+7+5, 36+27+15+14+10+7+6, 36+27+15+14+10+8+7+1, 36+27+15+14+10+8+7+2, 36+27+15+14+10+8+7+3, 36+27+15+14+10+8+7+4, 36+27+15+14+10+8+7+5, 36+27+15+14+10+8+7+6, 36+27+15+14+10+9+7+1, 36+27+15+14+10+9+7+2, 36+27+15+14+10+9+7+3, 36+27+15+14+10+9+7+4, 36+27+15+14+10+9+7+5, 36+27+15+14+10+9+7+6, 36+27+15+14+11+10+1, 36+27+15+14+11+10+2, 36+27+15+14+11+10+3, 36+27+15+14+11+10+4, 36+27+15+14+11+10+5, 36+27+15+14+11+10+6, 36+27+15+14+11+10+7+1, 36+27+15+14+11+10+7+2, 36+27+15+14+11+10+7+3, 36+27+15+14+11+10+7+4, 36+27+15+14+11+10+7+5, 36+27+15+14+11+10+7+6, 36+27+15+14+11+10+8+7+1, 36+27+15+14+11+10+8+7+2,

36+27+15+14+11+10+8+7+3,
36+27+15+14+11+10+8+7+4,
36+27+15+14+11+10+8+7+5,
36+27+15+14+11+10+8+7+6,
36+27+15+14+11+10+9+7+1,
36+27+15+14+11+10+9+7+2,
36+27+15+14+11+10+9+7+3,
36+27+15+14+11+10+9+7+4,
36+27+15+14+11+10+9+7+5,
36+27+15+14+11+10+9+7+6, 36+27+15+14+12+10+1, 36+27+15+14+12+10+2, 36+27+15+14+12+10+3, 36+27+15+14+12+10+4, 36+27+15+14+12+10+5, 36+27+15+14+12+10+6, 36+27+15+14+12+10+7+1, 36+27+15+14+12+10+7+2, 36+27+15+14+12+10+7+3, 36+27+15+14+12+10+7+4, 36+27+15+14+12+10+7+5, 36+27+15+14+12+10+7+6, 36+27+15+14+12+10+8+7+1,
36+27+15+14+12+10+8+7+2,
36+27+15+14+12+10+8+7+3,
36+27+15+14+12+10+8+7+4,
36+27+15+14+12+10+8+7+5,
36+27+15+14+12+10+8+7+6,
36+27+15+14+12+10+9+7+1,
36+27+15+14+12+10+9+7+2,
36+27+15+14+12+10+9+7+3,
36+27+15+14+12+10+9+7+4,
36+27+15+14+12+10+9+7+5,
36+27+15+14+12+10+9+7+6, 36+27+15+14+13+10+1, 36+27+15+14+13+10+2, 36+27+15+14+13+10+3, 36+27+15+14+13+10+4, 36+27+15+14+13+10+5, 36+27+15+14+13+10+6, 36+27+15+14+13+10+7+1, 36+27+15+14+13+10+7+2, 36+27+15+14+13+10+7+3, 36+27+15+14+13+10+7+4, 36+27+15+14+13+10+7+5, 36+27+15+14+13+10+7+6, 36+27+15+14+13+10+8+7+1,
36+27+15+14+13+10+8+7+2,
36+27+15+14+13+10+8+7+3,
36+27+15+14+13+10+8+7+4,
36+27+15+14+13+10+8+7+5,
36+27+15+14+13+10+8+7+6,
36+27+15+14+13+10+9+7+1,
36+27+15+14+13+10+9+7+2,
36+27+15+14+13+10+9+7+3,
36+27+15+14+13+10+9+7+4,
36+27+15+14+13+10+9+7+5,
36+27+15+14+13+10+9+7+6, 36+27+16+1, 36+27+16+2, 36+27+16+3, 36+27+16+4, 36+27+16+5, 36+27+16+6, 36+27+16+7+1, 36+27+16+7+2, 36+27+16+7+3, 36+27+16+7+4, 36+27+16+7+5, 36+27+16+7+6, 36+27+16+8+7+1, 36+27+16+8+7+2, 36+27+16+8+7+3, 36+27+16+8+7+4, 36+27+16+8+7+5, 36+27+16+8+7+6, 36+27+16+9+7+1, 36+27+16+9+7+2, 36+27+16+9+7+3, 36+27+16+9+7+4, 36+27+16+9+7+5, 36+27+16+9+7+6, 36+27+16+10+1, 36+27+16+10+2, 36+27+16+10+3, 36+27+16+10+4, 36+27+16+10+5, 36+27+16+10+6, 36+27+16+10+7+1, 36+27+16+10+7+2, 36+27+16+10+7+3, 36+27+16+10+7+4, 36+27+16+10+7+5, 36+27+16+10+7+6, 36+27+16+10+8+7+1, 36+27+16+10+8+7+2, 36+27+16+10+8+7+3, 36+27+16+10+8+7+4, 36+27+16+10+8+7+5, 36+27+16+10+8+7+6, 36+27+16+10+9+7+1, 36+27+16+10+9+7+2, 36+27+16+10+9+7+3, 36+27+16+10+9+7+4, 36+27+16+10+9+7+5, 36+27+16+10+9+7+6, 36+27+16+11+10+1, 36+27+16+11+10+2, 36+27+16+11+10+3, 36+27+16+11+10+4, 36+27+16+11+10+5, 36+27+16+11+10+6, 36+27+16+11+10+7+1, 36+27+16+11+10+7+2, 36+27+16+11+10+7+3, 36+27+16+11+10+7+4, 36+27+16+11+10+7+5, 36+27+16+11+10+7+6, 36+27+16+11+10+8+7+1, 36+27+16+11+10+8+7+2, 36+27+16+11+10+8+7+3, 36+27+16+11+10+8+7+4, 36+27+16+11+10+8+7+5, 36+27+16+11+10+8+7+6, 36+27+16+11+10+9+7+1, 36+27+16+11+10+9+7+2, 36+27+16+11+10+9+7+3, 36+27+16+11+10+9+7+4, 36+27+16+11+10+9+7+5, 36+27+16+11+10+9+7+6, 36+27+16+12+10+1, 36+27+16+12+10+2, 36+27+16+12+10+3, 36+27+16+12+10+4, 36+27+16+12+10+5, 36+27+16+12+10+6, 36+27+16+12+10+7+1, 36+27+16+12+10+7+2, 36+27+16+12+10+7+3, 36+27+16+12+10+7+4, 36+27+16+12+10+7+5, 36+27+16+12+10+7+6, 36+27+16+12+10+8+7+1, 36+27+16+12+10+8+7+2, 36+27+16+12+10+8+7+3, 36+27+16+12+10+8+7+4, 36+27+16+12+10+8+7+5, 36+27+16+12+10+8+7+6, 36+27+16+12+10+9+7+1, 36+27+16+12+10+9+7+2, 36+27+16+12+10+9+7+3, 36+27+16+12+10+9+7+4, 36+27+16+12+10+9+7+5, 36+27+16+12+10+9+7+6, 36+27+16+13+10+1, 36+27+16+13+10+2, 36+27+16+13+10+3, 36+27+16+13+10+4, 36+27+16+13+10+5, 36+27+16+13+10+6, 36+27+16+13+10+7+1, 36+27+16+13+10+7+2, 36+27+16+13+10+7+3, 36+27+16+13+10+7+4, 36+27+16+13+10+7+5, 36+27+16+13+10+7+6, 36+27+16+13+10+8+7+1, 36+27+16+13+10+8+7+2, 36+27+16+13+10+8+7+3, 36+27+16+13+10+8+7+4, 36+27+16+13+10+8+7+5, 36+27+16+13+10+8+7+6, 36+27+16+13+10+9+7+1, 36+27+16+13+10+9+7+2, 36+27+16+13+10+9+7+3, 36+27+16+13+10+9+7+4, 36+27+16+13+10+9+7+5, 36+27+16+13+10+9+7+6, 36+27+16+14+1, 36+27+16+14+2, 36+27+16+14+3, 36+27+16+14+4, 36+27+16+14+5, 36+27+16+14+6, 36+27+16+14+7+1, 36+27+16+14+7+2, 36+27+16+14+7+3, 36+27+16+14+7+4, 36+27+16+14+7+5, 36+27+16+14+7+6, 36+27+16+14+8+7+1, 36+27+16+14+8+7+2, 36+27+16+14+8+7+3, 36+27+16+14+8+7+4, 36+27+16+14+8+7+5, 36+27+16+14+8+7+6, 36+27+16+14+9+7+1, 36+27+16+14+9+7+2, 36+27+16+14+9+7+3, 36+27+16+14+9+7+4, 36+27+16+14+9+7+5, 36+27+16+14+9+7+6, 36+27+16+14+10+1, 36+27+16+14+10+2, 36+27+16+14+10+3, 36+27+16+14+10+4, 36+27+16+14+10+5, 36+27+16+14+10+6, 36+27+16+14+10+7+1, 36+27+16+14+10+7+2, 36+27+16+14+10+7+3, 36+27+16+14+10+7+4, 36+27+16+14+10+7+5, 36+27+16+14+10+7+6, 36+27+16+14+10+8+7+1, 36+27+16+14+10+8+7+2, 36+27+16+14+10+8+7+3, 36+27+16+14+10+8+7+4, 36+27+16+14+10+8+7+5, 36+27+16+14+10+8+7+6, 36+27+16+14+10+9+7+1, 36+27+16+14+10+9+7+2, 36+27+16+14+10+9+7+3, 36+27+16+14+10+9+7+4, 36+27+16+14+10+9+7+5, 36+27+16+14+10+9+7+6, 36+27+16+14+11+10+1, 36+27+16+14+11+10+2, 36+27+16+14+11+10+3, 36+27+16+14+11+10+4, 36+27+16+14+11+10+5, 36+27+16+14+11+10+6, 36+27+16+14+11+10+7+1, 36+27+16+14+11+10+7+2, 36+27+16+14+11+10+7+3, 36+27+16+14+11+10+7+4, 36+27+16+14+11+10+7+5, 36+27+16+14+11+10+7+6, 36+27+16+14+11+10+8+7+1,
36+27+16+14+11+10+8+7+2,
36+27+16+14+11+10+8+7+3,
36+27+16+14+11+10+8+7+4,
36+27+16+14+11+10+8+7+5,
36+27+16+14+11+10+8+7+6,
36+27+16+14+11+10+9+7+1,
36+27+16+14+11+10+9+7+2,
36+27+16+14+11+10+9+7+3,
36+27+16+14+11+10+9+7+4,
36+27+16+14+11+10+9+7+5,
36+27+16+14+11+10+9+7+6, 36+27+16+14+12+10+1, 36+27+16+14+12+10+2, 36+27+16+14+12+10+3, 36+27+

16+14+12+10+4, 36+27+16+14+12+10+5, 36+27+16+14+12+10+6, 36+27+16+14+12+10+7+1, 36+27+16+14+12+10+7+2, 36+27+16+14+12+10+7+3, 36+27+16+14+12+10+7+4, 36+27+16+14+12+10+7+5, 36+27+16+14+12+10+7+6, 36+27+16+14+12+10+8+7+1, 36+27+16+14+12+10+8+7+2, 36+27+16+14+12+10+8+7+3, 36+27+16+14+12+10+8+7+4, 36+27+16+14+12+10+8+7+5, 36+27+16+14+12+10+8+7+6, 36+27+16+14+12+10+9+7+1, 36+27+16+14+12+10+9+7+2, 36+27+16+14+12+10+9+7+3, 36+27+16+14+12+10+9+7+4, 36+27+16+14+12+10+9+7+5, 36+27+16+14+12+10+9+7+6, 36+27+16+14+13+10+1, 36+27+16+14+13+10+2, 36+27+16+14+13+10+3, 36+27+16+14+13+10+4, 36+27+16+14+13+10+5, 36+27+16+14+13+10+6, 36+27+16+14+13+10+7+1, 36+27+16+14+13+10+7+2, 36+27+16+14+13+10+7+3, 36+27+16+14+13+10+7+4, 36+27+16+14+13+10+7+5, 36+27+16+14+13+10+7+6, 36+27+16+14+13+10+8+7+1, 36+27+16+14+13+10+8+7+2, 36+27+16+14+13+10+8+7+3, 36+27+16+14+13+10+8+7+4, 36+27+16+14+13+10+8+7+5, 36+27+16+14+13+10+8+7+6, 36+27+16+14+13+10+9+7+1, 36+27+16+14+13+10+9+7+2, 36+27+16+14+13+10+9+7+3, 36+27+16+14+13+10+9+7+4, 36+27+16+14+13+10+9+7+5, 36+27+16+14+13+10+9+7+6, 36+27+17+1, 36+27+17+2, 36+27+17+3, 36+27+18+17+1, 36+27+18+17+2, 36+27+18+17+3, 36+27+19+4, 36+27+19+5, 36+27+19+6, 36+27+20+1, 36+27+20+2, 36+27+20+3, 36+27+21+20+1, 36+27+21+20+2, 36+27+21+20+3, 36+27+22+20+1, 36+27+22+20+2, 36+27+22+20+3, 36+27+23+20+1, 36+27+23+20+2, 36+27+23+20+3, 36+27+24+4, 36+27+24+5, 36+27+24+6, 36+27+25+4, 36+27+25+5, 36+27+25+6, 36+27+26+4, 36+27+26+5, 36+27+26+6, 36+28+1, 36+28+2, 36+28+3, 36+28+4, 36+28+5, 36+28+6, 36+28+7+1, 36+28+7+2, 36+28+7+3, 36+28+7+4, 36+28+7+5, 36+28+7+6, 36+28+8+7+1, 36+28+8+7+2, 36+28+8+7+3, 36+28+8+7+4, 36+28+8+7+5, 36+28+8+7+6, 36+28+9+7+1, 36+28+9+7+2, 36+28+9+7+3, 36+28+9+7+4, 36+28+9+7+5, 36+28+9+7+6, 36+28+10+1, 36+28+10+2, 36+28+10+3, 36+28+10+4, 36+28+10+5, 36+28+10+6, 36+28+10+7+1, 36+28+10+7+2, 36+28+10+7+3, 36+28+10+7+4, 36+28+10+7+5, 36+28+10+7+6, 36+28+10+8+7+1, 36+28+10+8+7+2, 36+28+10+8+7+3, 36+28+10+8+7+4, 36+28+10+8+7+5, 36+28+10+8+7+6, 36+28+10+9+7+1, 36+28+10+9+7+2, 36+28+10+9+7+3, 36+28+10+9+7+4, 36+28+10+9+7+5, 36+28+10+9+7+6, 36+28+11+10+1, 36+28+11+10+2, 36+28+11+10+3, 36+28+11+10+4, 36+28+11+10+5, 36+28+11+10+6, 36+28+11+10+7+1, 36+28+11+10+7+2, 36+28+11+10+7+3, 36+28+11+10+7+4, 36+28+11+10+7+5, 36+28+11+10+7+6, 36+28+11+10+8+7+1, 36+28+11+10+8+7+2, 36+28+11+10+8+7+3, 36+28+11+10+8+7+4, 36+28+11+10+8+7+5, 36+28+11+10+8+7+6, 36+28+11+10+9+7+1, 36+28+11+10+9+7+2, 36+28+11+10+9+7+3, 36+28+11+10+9+7+4, 36+28+11+10+9+7+5, 36+28+11+10+9+7+6, 36+28+12+10+1, 36+28+12+10+2, 36+28+12+10+3, 36+28+12+10+4, 36+28+12+10+5, 36+28+12+10+6, 36+28+12+10+7+1, 36+28+12+10+7+2, 36+28+12+10+7+3, 36+28+12+10+7+4, 36+28+12+10+7+5, 36+28+12+10+7+6, 36+28+12+10+8+7+1, 36+28+12+10+8+7+2, 36+28+12+10+8+7+3, 36+28+12+10+8+7+4, 36+28+12+10+8+7+5, 36+28+12+10+8+7+6, 36+28+12+10+9+7+1, 36+28+12+10+9+7+2, 36+28+12+10+9+7+3, 36+28+12+10+9+7+4, 36+28+12+10+9+7+5, 36+28+12+10+9+7+6, 36+28+13+10+1, 36+28+13+10+2, 36+28+13+10+3, 36+28+13+10+4, 36+28+13+10+5, 36+28+13+10+6, 36+28+13+10+7+1, 36+28+13+10+7+2, 36+28+13+10+7+3, 36+28+13+10+7+4, 36+28+13+10+7+5, 36+28+13+10+7+6, 36+28+13+10+8+7+1, 36+28+13+10+8+7+2, 36+28+13+10+8+7+3, 36+28+13+10+8+7+4, 36+28+13+10+8+7+5, 36+28+13+10+8+7+6, 36+28+13+10+9+7+1, 36+28+13+10+9+7+2, 36+28+13+10+9+7+3, 36+28+13+10+9+7+4, 36+28+13+10+9+7+5, 36+28+13+10+9+7+6, 36+28+14+1, 36+28+14+2, 36+28+14+3, 36+28+14+4, 36+28+14+5, 36+28+14+6, 36+28+14+7+1, 36+28+14+7+2, 36+28+14+7+3, 36+28+14+7+4, 36+28+14+7+5, 36+28+14+7+6, 36+28+14+8+7+1, 36+28+14+8+7+2, 36+28+14+8+7+3, 36+28+14+8+7+4, 36+28+14+8+7+5, 36+28+14+8+7+6, 36+28+14+9+7+1, 36+28+14+9+7+2, 36+28+14+9+7+3, 36+28+14+9+7+4, 36+28+14+9+7+5, 36+28+14+9+7+6, 36+28+14+10+1, 36+28+14+10+2, 36+28+14+10+3, 36+28+14+10+4, 36+28+14+10+5, 36+28+14+10+6, 36+28+14+10+7+1, 36+28+14+10+7+2, 36+28+14+10+7+3, 36+28+14+10+7+4, 36+28+14+10+7+5, 36+28+14+10+7+6, 36+28+14+10+8+7+1, 36+28+14+10+8+7+2, 36+28+14+10+8+7+3, 36+28+14+10+8+7+4, 36+28+14+10+8+7+5, 36+28+14+10+8+7+6, 36+28+14+10+9+7+1, 36+28+14+10+9+7+2, 36+28+14+10+9+7+3, 36+28+14+10+9+7+4, 36+28+14+10+9+7+5, 36+28+14+10+9+7+6, 36+28+14+11+10+1, 36+28+14+11+10+2, 36+28+14+11+10+3, 36+28+14+11+10+4, 36+28+14+11+10+5, 36+28+14+11+10+6, 36+28+14+11+10+7+1, 36+28+14+11+10+7+2, 36+28+14+11+10+7+3, 36+28+14+11+10+7+4, 36+28+14+11+10+7+5, 36+28+14+11+10+7+6, 36+28+14+11+10+8+7+1, 36+28+14+11+10+8+7+2, 36+28+14+11+10+8+7+3, 36+28+14+11+10+8+7+4, 36+28+14+11+10+8+7+5, 36+28+14+11+10+8+7+6, 36+28+14+11+10+9+7+1, 36+28+14+11+10+9+7+2, 36+28+14+11+10+9+7+3, 36+28+14+11+10+9+7+4, 36+28+14+11+10+9+7+5, 36+28+14+11+10+9+7+6, 36+28+14+12+10+1, 36+28+14+12+10+2, 36+28+14+12+10+3, 36+28+14+12+10+4, 36+28+14+12+10+5, 36+28+14+12+10+6, 36+28+14+12+10+7+1, 36+28+14+12+10+7+2, 36+28+14+12+10+7+3, 36+28+14+12+10+7+4, 36+28+14+12+10+7+5, 36+28+14+12+10+7+6, 36+28+14+12+10+8+7+1, 36+28+14+12+10+8+7+2, 36+28+14+12+10+8+7+3, 36+28+14+12+10+8+7+4, 36+28+14+12+10+8+7+5, 36+28+14+12+10+8+7+6, 36+28+14+12+10+9+7+1, 36+28+14+12+10+9+7+2, 36+28+14+12+10+9+7+3, 36+28+14+12+10+9+7+4, 36+28+14+12+10+9+7+5, 36+28+14+12+10+9+7+6, 36+28+14+13+10+1, 36+28+14+13+10+2, 36+28+14+13+10+3, 36+28+14+13+10+4, 36+28+14+13+10+5, 36+28+14+13+10+6, 36+28+14+13+10+7+1, 36+28+14+13+10+7+2, 36+28+14+13+10+7+3, 36+28+14+13+10+7+4, 36+28+14+13+10+7+5, 36+28+14+13+10+7+6, 36+28+14+13+10+8+7+1, 36+28+14+13+10+8+7+2, 36+28+14+13+10+8+7+3, 36+28+14+13+10+8+7+4, 36+28+14+13+10+8+7+5, 36+28+14+13+10+8+7+6, 36+28+14+13+10+9+7+1, 36+28+14+13+10+9+7+2, 36+28+14+13+10+9+7+3, 36+28+14+13+10+9+7+4, 36+28+14+13+10+9+7+5, 36+28+14+13+10+9+7+6, 36+28+15+1, 36+28+15+2, 36+28+15+3, 36+28+15+4, 36+28+15+5, 36+28+15+6, 36+28+15+7+1, 36+28+15+7+2, 36+28+15+7+3,

36+28+15+7+4, 36+28+15+7+5, 36+28+15+7+6, 36+28+15+8+7+1, 36+28+15+8+7+2, 36+28+15+8+7+3, 36+28+15+8+7+4, 36+28+15+8+7+5, 36+28+15+8+7+6, 36+28+15+9+7+1, 36+28+15+9+7+2, 36+28+15+9+7+3, 36+28+15+9+7+4, 36+28+15+9+7+5, 36+28+15+9+7+6, 36+28+15+10+1, 36+28+15+10+2, 36+28+15+10+3, 36+28+15+10+4, 36+28+15+10+5, 36+28+15+10+6, 36+28+15+10+7+1, 36+28+15+10+7+2, 36+28+15+10+7+3, 36+28+15+10+7+4, 36+28+15+10+7+5, 36+28+15+10+7+6, 36+28+15+10+8+7+1, 36+28+15+10+8+7+2, 36+28+15+10+8+7+3, 36+28+15+10+8+7+4, 36+28+15+10+8+7+5, 36+28+15+10+8+7+6, 36+28+15+10+9+7+1, 36+28+15+10+9+7+2, 36+28+15+10+9+7+3, 36+28+15+10+9+7+4, 36+28+15+10+9+7+5, 36+28+15+10+9+7+6, 36+28+15+11+10+1, 36+28+15+11+10+2, 36+28+15+11+10+3, 36+28+15+11+10+4, 36+28+15+11+10+5, 36+28+15+11+10+6, 36+28+15+11+10+7+1, 36+28+15+11+10+7+2, 36+28+15+11+10+7+3, 36+28+15+11+10+7+4, 36+28+15+11+10+7+5, 36+28+15+11+10+7+6, 36+28+15+11+10+8+7+1, 36+28+15+11+10+8+7+2, 36+28+15+11+10+8+7+3, 36+28+15+11+10+8+7+4, 36+28+15+11+10+8+7+5, 36+28+15+11+10+8+7+6, 36+28+15+11+10+9+7+1, 36+28+15+11+10+9+7+2, 36+28+15+11+10+9+7+3, 36+28+15+11+10+9+7+4, 36+28+15+11+10+9+7+5, 36+28+15+11+10+9+7+6, 36+28+15+12+10+1, 36+28+15+12+10+2, 36+28+15+12+10+3, 36+28+15+12+10+4, 36+28+15+12+10+5, 36+28+15+12+10+6, 36+28+15+12+10+7+1, 36+28+15+12+10+7+2, 36+28+15+12+10+7+3, 36+28+15+12+10+7+4, 36+28+15+12+10+7+5, 36+28+15+12+10+7+6, 36+28+15+12+10+8+7+1, 36+28+15+12+10+8+7+2, 36+28+15+12+10+8+7+3, 36+28+15+12+10+8+7+4, 36+28+15+12+10+8+7+5, 36+28+15+12+10+8+7+6, 36+28+15+12+10+9+7+1, 36+28+15+12+10+9+7+2, 36+28+15+12+10+9+7+3, 36+28+15+12+10+9+7+4, 36+28+15+12+10+9+7+5, 36+28+15+12+10+9+7+6, 36+28+15+13+10+1, 36+28+15+13+10+2, 36+28+15+13+10+3, 36+28+15+13+10+4, 36+28+15+13+10+5, 36+28+15+13+10+6, 36+28+15+13+10+7+1, 36+28+15+13+10+7+2, 36+28+15+13+10+7+3, 36+28+15+13+10+7+4, 36+28+15+13+10+7+5, 36+28+15+13+10+7+6, 36+28+15+13+10+8+7+1, 36+28+15+13+10+8+7+2, 36+28+15+13+10+8+7+3, 36+28+15+13+10+8+7+4, 36+28+15+13+10+8+7+5, 36+28+15+13+10+8+7+6, 36+28+15+13+10+9+7+1, 36+28+15+13+10+9+7+2, 36+28+15+13+10+9+7+3, 36+28+15+13+10+9+7+4, 36+28+15+13+10+9+7+5, 36+28+15+13+10+9+7+6, 36+28+15+14+1, 36+28+15+14+2, 36+28+15+14+3, 36+28+15+14+4, 36+28+15+14+5, 36+28+15+14+6, 36+28+15+14+7+1, 36+28+15+14+7+2, 36+28+15+14+7+3, 36+28+15+14+7+4, 36+28+15+14+7+5, 36+28+15+14+7+6, 36+28+15+14+8+7+1, 36+28+15+14+8+7+2, 36+28+15+14+8+7+3, 36+28+15+14+8+7+4, 36+28+15+14+8+7+5, 36+28+15+14+8+7+6, 36+28+15+14+9+7+1, 36+28+15+14+9+7+2, 36+28+15+14+9+7+3, 36+28+15+14+9+7+4, 36+28+15+14+9+7+5, 36+28+15+14+9+7+6, 36+28+15+14+10+1, 36+28+15+14+10+2, 36+28+15+14+10+3, 36+28+15+14+10+4, 36+28+15+14+10+5, 36+28+15+14+10+6, 36+28+15+14+10+7+1, 36+28+15+14+10+7+2, 36+28+15+14+10+7+3, 36+28+15+14+10+7+4, 36+28+15+14+10+7+5, 36+28+15+14+10+7+6, 36+28+15+14+10+8+7+1, 36+28+15+14+10+8+7+2, 36+28+15+14+10+8+7+3, 36+28+15+14+10+8+7+4, 36+28+15+14+10+8+7+5, 36+28+15+14+10+8+7+6, 36+28+15+14+10+9+7+1, 36+28+15+14+10+9+7+2, 36+28+15+14+10+9+7+3, 36+28+15+14+10+9+7+4, 36+28+15+14+10+9+7+5, 36+28+15+14+10+9+7+6, 36+28+15+14+11+10+1, 36+28+15+14+11+10+2, 36+28+15+14+11+10+3, 36+28+15+14+11+10+4, 36+28+15+14+11+10+5, 36+28+15+14+11+10+6, 36+28+15+14+11+10+7+1, 36+28+15+14+11+10+7+2, 36+28+15+14+11+10+7+3, 36+28+15+14+11+10+7+4, 36+28+15+14+11+10+7+5, 36+28+15+14+11+10+7+6, 36+28+15+14+11+10+8+7+1, 36+28+15+14+11+10+8+7+2, 36+28+15+14+11+10+8+7+3, 36+28+15+14+11+10+8+7+4, 36+28+15+14+11+10+8+7+5, 36+28+15+14+11+10+8+7+6, 36+28+15+14+11+10+9+7+1, 36+28+15+14+11+10+9+7+2, 36+28+15+14+11+10+9+7+3, 36+28+15+14+11+10+9+7+4, 36+28+15+14+11+10+9+7+5, 36+28+15+14+11+10+9+7+6, 36+28+15+14+12+10+1, 36+28+15+14+12+10+2, 36+28+15+14+12+10+3, 36+28+15+14+12+10+4, 36+28+15+14+12+10+5, 36+28+15+14+12+10+6, 36+28+15+14+12+10+7+1, 36+28+15+14+12+10+7+2, 36+28+15+14+12+10+7+3, 36+28+15+14+12+10+7+4, 36+28+15+14+12+10+7+5, 36+28+15+14+12+10+7+6, 36+28+15+14+12+10+8+7+1, 36+28+15+14+12+10+8+7+2, 36+28+15+14+12+10+8+7+3, 36+28+15+14+12+10+8+7+4, 36+28+15+14+12+10+8+7+5, 36+28+15+14+12+10+8+7+6, 36+28+15+14+12+10+9+7+1, 36+28+15+14+12+10+9+7+2, 36+28+15+14+12+10+9+7+3, 36+28+15+14+12+10+9+7+4, 36+28+15+14+12+10+9+7+5, 36+28+15+14+12+10+9+7+6, 36+28+15+14+13+10+1, 36+28+15+14+13+10+2, 36+28+15+14+13+10+3, 36+28+15+14+13+10+4, 36+28+15+14+13+10+5, 36+28+15+14+13+10+6, 36+28+15+14+13+10+7+1, 36+28+15+14+13+10+7+2, 36+28+15+14+13+10+7+3, 36+28+15+14+13+10+7+4, 36+28+15+14+13+10+7+5, 36+28+15+14+13+10+7+6, 36+28+15+14+13+10+8+7+1, 36+28+15+14+13+10+8+7+2, 36+28+15+14+13+10+8+7+3, 36+28+15+14+13+10+8+7+4, 36+28+15+14+13+10+8+7+5, 36+28+15+14+13+10+8+7+6, 36+28+15+14+13+10+9+7+1, 36+28+15+14+13+10+9+7+2, 36+28+15+14+13+10+9+7+3, 36+28+15+14+13+10+9+7+4, 36+28+15+14+13+10+9+7+5, 36+28+15+14+13+10+9+7+6, 36+28+16+1, 36+28+16+2, 36+28+16+3, 36+28+16+4, 36+28+16+5, 36+28+16+6, 36+28+16+7+1, 36+28+16+7+2, 36+28+16+7+3, 36+28+16+7+4, 36+28+16+7+5, 36+28+16+7+6, 36+28+16+8+7+1, 36+28+16+8+7+2, 36+28+16+8+7+3, 36+28+16+8+7+4, 36+28+16+8+7+5, 36+28+16+8+7+6, 36+28+16+9+7+1, 36+28+16+9+7+2, 36+28+16+9+7+3, 36+28+16+9+7+4, 36+28+16+9+7+5, 36+28+16+9+7+6, 36+28+16+10+1, 36+28+16+10+2, 36+28+16+10+3, 36+28+16+10+4, 36+28+16+10+5, 36+28+16+10+6, 36+28+16+10+7+1, 36+28+16+10+7+2, 36+28+16+10+7+3, 36+28+16+10+7+4, 36+28+16+10+7+5, 36+28+16+10+7+6, 36+28+16+10+8+7+1, 36+28+16+10+8+7+2, 36+28+16+10+8+7+3, 36+28+16+10+8+7+4, 36+28+16+10+8+7+

5, 36+28+16+10+8+7+6, 36+28+16+10+9+7+1, 36+28+16+10+9+7+2, 36+28+16+10+9+7+3, 36+28+16+10+9+7+4, 36+28+16+10+9+7+5, 36+28+16+10+9+7+6, 36+28+16+11+10+1, 36+28+16+11+10+2, 36+28+16+11+10+3, 36+28+16+11+10+4, 36+28+16+11+10+5, 36+28+16+11+10+6, 36+28+16+11+10+7+1, 36+28+16+11+10+7+2, 36+28+16+11+10+7+3, 36+28+16+11+10+7+4, 36+28+16+11+10+7+5, 36+28+16+11+10+7+6, 36+28+16+11+10+8+7+1, 36+28+16+11+10+8+7+2, 36+28+16+11+10+8+7+3, 36+28+16+11+10+8+7+4, 36+28+16+11+10+8+7+5, 36+28+16+11+10+8+7+6, 36+28+16+11+10+9+7+1, 36+28+16+11+10+9+7+2, 36+28+16+11+10+9+7+3, 36+28+16+11+10+9+7+4, 36+28+16+11+10+9+7+5, 36+28+16+11+10+9+7+6, 36+28+16+12+10+1, 36+28+16+12+10+2, 36+28+16+12+10+3, 36+28+16+12+10+4, 36+28+16+12+10+5, 36+28+16+12+10+6, 36+28+16+12+10+7+1, 36+28+16+12+10+7+2, 36+28+16+12+10+7+3, 36+28+16+12+10+7+4, 36+28+16+12+10+7+5, 36+28+16+12+10+7+6, 36+28+16+12+10+8+7+1, 36+28+16+12+10+8+7+2, 36+28+16+12+10+8+7+3, 36+28+16+12+10+8+7+4, 36+28+16+12+10+8+7+5, 36+28+16+12+10+8+7+6, 36+28+16+12+10+9+7+1, 36+28+16+12+10+9+7+2, 36+28+16+12+10+9+7+3, 36+28+16+12+10+9+7+4, 36+28+16+12+10+9+7+5, 36+28+16+12+10+9+7+6, 36+28+16+13+10+1, 36+28+16+13+10+2, 36+28+16+13+10+3, 36+28+16+13+10+4, 36+28+16+13+10+5, 36+28+16+13+10+6, 36+28+16+13+10+7+1, 36+28+16+13+10+7+2, 36+28+16+13+10+7+3, 36+28+16+13+10+7+4, 36+28+16+13+10+7+5, 36+28+16+13+10+7+6, 36+28+16+13+10+8+7+1, 36+28+16+13+10+8+7+2, 36+28+16+13+10+8+7+3, 36+28+16+13+10+8+7+4, 36+28+16+13+10+8+7+5, 36+28+16+13+10+8+7+6, 36+28+16+13+10+9+7+1, 36+28+16+13+10+9+7+2, 36+28+16+13+10+9+7+3, 36+28+16+13+10+9+7+4, 36+28+16+13+10+9+7+5, 36+28+16+13+10+9+7+6, 36+28+16+14+1, 36+28+16+14+2, 36+28+16+14+3, 36+28+16+14+4, 36+28+16+14+5, 36+28+16+14+6, 36+28+16+14+7+1, 36+28+16+14+7+2, 36+28+16+14+7+3, 36+28+16+14+7+4, 36+28+16+14+7+5, 36+28+16+14+7+6, 36+28+16+14+8+7+1, 36+28+16+14+8+7+2, 36+28+16+14+8+7+3, 36+28+16+14+8+7+4, 36+28+16+14+8+7+5, 36+28+16+14+8+7+6, 36+28+16+14+9+7+1, 36+28+16+14+9+7+2, 36+28+16+14+9+7+3, 36+28+16+14+9+7+4, 36+28+16+14+9+7+5, 36+28+16+14+9+7+6, 36+28+16+14+10+1, 36+28+16+14+10+2, 36+28+16+14+10+3, 36+28+16+14+10+4, 36+28+16+14+10+5, 36+28+16+14+10+6, 36+28+16+14+10+7+1, 36+28+16+14+10+7+2, 36+28+16+14+10+7+3, 36+28+16+14+10+7+4, 36+28+16+14+10+7+5, 36+28+16+14+10+7+6, 36+28+16+14+10+8+7+1, 36+28+16+14+10+8+7+2, 36+28+16+14+10+8+7+3, 36+28+16+14+10+8+7+4, 36+28+16+14+10+8+7+5, 36+28+16+14+10+8+7+6, 36+28+16+14+10+9+7+1, 36+28+16+14+10+9+7+2, 36+28+16+14+10+9+7+3, 36+28+16+14+10+9+7+4, 36+28+16+14+10+9+7+5, 36+28+16+14+10+9+7+6, 36+28+16+14+11+10+1, 36+28+16+14+11+10+2, 36+28+16+14+11+10+3, 36+28+16+14+11+10+4, 36+28+16+14+11+10+5, 36+28+16+14+11+10+6, 36+28+16+14+11+10+7+1, 36+28+16+14+11+10+7+2, 36+28+16+14+11+10+7+3, 36+28+16+14+11+10+7+4, 36+28+16+14+11+10+7+5, 36+28+16+14+11+10+7+6, 36+28+16+14+11+10+8+7+1, 36+28+16+14+11+10+8+7+2, 36+28+16+14+11+10+8+7+3, 36+28+16+14+11+10+8+7+4, 36+28+16+14+11+10+8+7+5, 36+28+16+14+11+10+8+7+6, 36+28+16+14+11+10+9+7+1, 36+28+16+14+11+10+9+7+2, 36+28+16+14+11+10+9+7+3, 36+28+16+14+11+10+9+7+4, 36+28+16+14+11+10+9+7+5, 36+28+16+14+11+10+9+7+6, 36+28+16+14+12+10+1, 36+28+16+14+12+10+2, 36+28+16+14+12+10+3, 36+28+16+14+12+10+4, 36+28+16+14+12+10+5, 36+28+16+14+12+10+6, 36+28+16+14+12+10+7+1, 36+28+16+14+12+10+7+2, 36+28+16+14+12+10+7+3, 36+28+16+14+12+10+7+4, 36+28+16+14+12+10+7+5, 36+28+16+14+12+10+7+6, 36+28+16+14+12+10+8+7+1, 36+28+16+14+12+10+8+7+2, 36+28+16+14+12+10+8+7+3, 36+28+16+14+12+10+8+7+4, 36+28+16+14+12+10+8+7+5, 36+28+16+14+12+10+8+7+6, 36+28+16+14+12+10+9+7+1, 36+28+16+14+12+10+9+7+2, 36+28+16+14+12+10+9+7+3, 36+28+16+14+12+10+9+7+4, 36+28+16+14+12+10+9+7+5, 36+28+16+14+12+10+9+7+6, 36+28+16+14+13+10+1, 36+28+16+14+13+10+2, 36+28+16+14+13+10+3, 36+28+16+14+13+10+4, 36+28+16+14+13+10+5, 36+28+16+14+13+10+6, 36+28+16+14+13+10+7+1, 36+28+16+14+13+10+7+2, 36+28+16+14+13+10+7+3, 36+28+16+14+13+10+7+4, 36+28+16+14+13+10+7+5, 36+28+16+14+13+10+7+6, 36+28+16+14+13+10+8+7+1, 36+28+16+14+13+10+8+7+2, 36+28+16+14+13+10+8+7+3, 36+28+16+14+13+10+8+7+4, 36+28+16+14+13+10+8+7+5, 36+28+16+14+13+10+8+7+6, 36+28+16+14+13+10+9+7+1, 36+28+16+14+13+10+9+7+2, 36+28+16+14+13+10+9+7+3, 36+28+16+14+13+10+9+7+4, 36+28+16+14+13+10+9+7+5, 36+28+16+14+13+10+9+7+6, 36+28+17+1, 36+28+17+2, 36+28+17+3, 36+28+18+17+1, 36+28+18+17+2, 36+28+18+17+3, 36+28+19+4, 36+28+19+5, 36+28+19+6, 36+28+20+1, 36+28+20+2, 36+28+20+3, 36+28+21+20+1, 36+28+21+20+2, 36+28+21+20+3, 36+28+22+20+1, 36+28+22+20+2, 36+28+22+20+3, 36+28+23+20+1, 36+28+23+20+2, 36+28+23+20+3, 36+28+24+4, 36+28+24+5, 36+28+24+6, 36+28+25+4, 36+28+25+5, 36+28+25+6, 36+28+26+4, 36+28+26+5, 36+28+26+6, 36+29+1, 36+29+2, 36+29+3, 36+30, 36+31, 36+32 and 36+33.

In the list above, the numbers refer to the embodiments according to their numbering provided hereinabove whereas "+" indicates the dependency from another embodiment. The different individualized embodiments are separated by commas. In other words, "4+3+1" for example refers to embodiment 4) depending on embodiment 3), depending on embodiment 1), i.e. embodiment "4+3+1" corresponds to embodiment 1) further limited by the features of embodiments 3) and 4). Likewise, "28+18+17+1" refers to embodiment 28) depending mutatis mutandis on embodiments 17) and 18), depending on embodiment 1), i.e. embodiment "28+18+17+1" corresponds to embodiment 1) further limited by the features of embodiment 28), further limited by the features of embodiments 17) and 18).

Besides, any characteristics described in this invention for the compounds of formula I (whether for the compounds themselves, salts thereof, compositions containing the compounds or salts thereof, uses of the compounds or salts thereof, etc.) apply mutatis mutandis to compounds of formula $I_{E1}$, formula $I_{E2}$, formula $I_P$, formula $I_{PE1}$, formula $I_{PE2}$, formula $I_2$, formula $I_3$ and formula $I_3'$.

The compounds of formula I can be manufactured in accordance with the present invention using the procedures described hereafter.

PREPARATION OF THE COMPOUNDS OF FORMULA I

General Preparation Methods:

Preparation of the Compounds of Formula I:

The compounds of formula I can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) and b) hereafter describe general methods for preparing compounds of formula I. If not indicated otherwise, the generic groups $R^{1a}$, $R^{1b}$, $R^2$, $R^3$, $R^4$, A, B, Q, U and Y and the integers m and n are as defined for formula I. General synthetic methods used repeatedly throughout the text below are referenced to and described in the above section entitled "General reaction techniques". Other abbreviations used are defined in the experimental section. In some instances the generic group B might be incompatible with the assembly illustrated in the procedures and schemes below and so will require the use of protecting groups. The use of protecting groups is well known in the art (see for example "*Protective Groups in Organic Synthesis*", T. W. Greene, P. G. M. Wuts, Wiley-Interscience, 1999).

The compounds of formula I can be obtained by methods a) or b) below:

a) By reacting the compounds of formula II

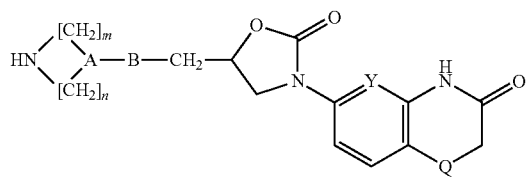

wherein A, B, Y, Q, m and n have the same meanings as in formula I, with a compound of formula III

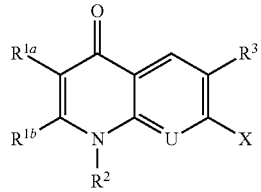

wherein $R^{1a}$ and $R^{1b}$ have the same meanings as in formula I or $R^{1a}$ represents the group $COOR^a$ wherein $R^a$ represent alkyl, benzyl, allyl or the group $B(OAc)_2$, $R^{1b}$ represents H and X represents halogen such as Br, Cl or I in presence of an organic base such TEA or DIPEA. In the case wherein $R^a$ represents alkyl, benzyl or allyl, the group $R^a$ can be removed by treatment respectively with an inorganic base such NaOH, hydrogenation over a noble metal catalyst such as Pd/C or by treatment with $Pd(OAc)_2$ in the presence of triethyl phosphite and sodium 2-methylhexanoate. In the particular case wherein $R^a$ represents $B(OAc)_2$ the reaction is followed by a treatment with an aq. inorganic acid such as HCl prior to purification.

b) By reacting the compounds of formula IV

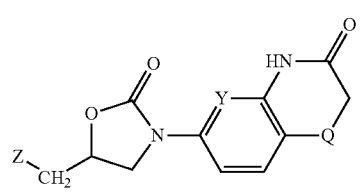

wherein each of m and n represents 2, with a compound of formula V

V

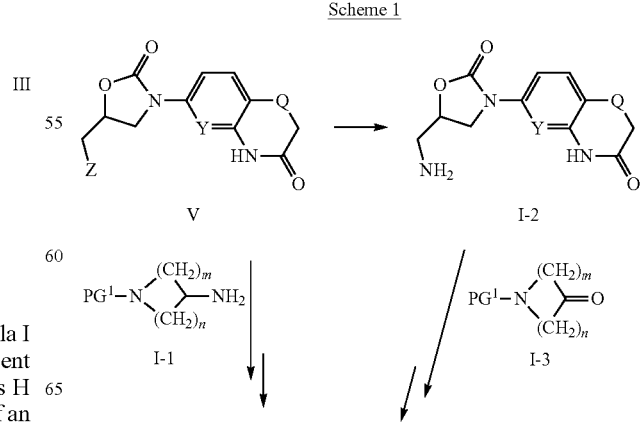

wherein Z represents a halogen such as iodine or a sulfonate such as MsO, TsO or TfO in presence of an organic base such TEA or DIPEA using general reaction technique 1.

Preparation of the Intermediates Used in the Preparation of the Compounds of Formula I:

Compounds of Formulae II and V:

The compounds of formula V can be prepared as described in or in analogy to literature procedures (WO 2008/126034 or WO 2010/041194).

The compounds of formula II can be prepared according to WO 2008/126034 (m=n=1) or by one of the general routes described in Schemes 1 and 2 hereafter.

Scheme 1

-continued

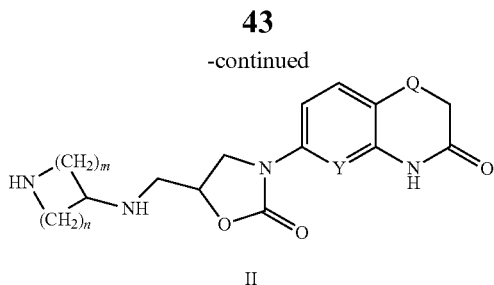

II

Scheme 3

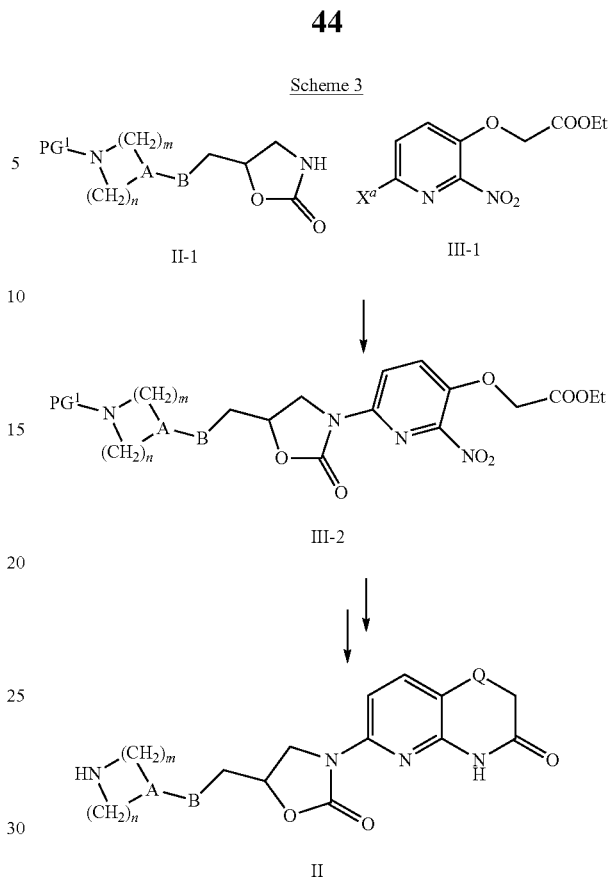

In Scheme 1, Z represents iodine or a sulfonate such as OMs or OTs and $PG^1$ represents an amine protecting group such as Cbz or Boc.

The compounds of formula V can be reacted (Scheme 1) with the amines of formula I-1 (commercially available) in presence of a base such TEA using general reaction technique 1 followed by removal of the amine protecting group using general reaction technique 2. Alternatively the compounds of formula V can be transformed into the corresponding amines of formula I-2 using general reaction technique(s) 3 or 4 and 5 and reacted with the ketones of formula I-3 (commercially available) using general reaction technique 6 followed by removal of the amine protecting group using general reaction technique 2.

Scheme 2

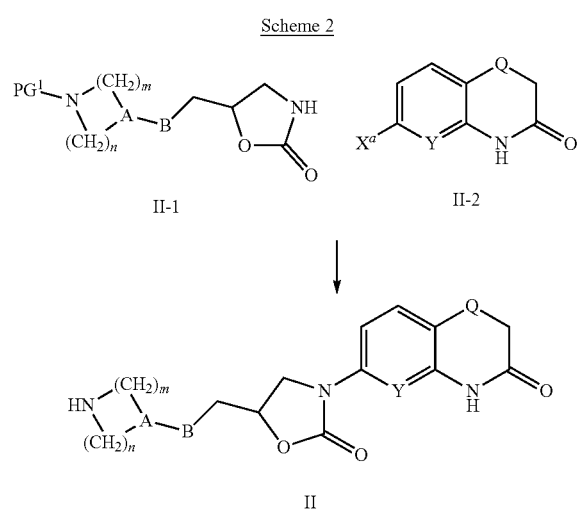

In Scheme 2, $X^a$ represents a halogen such as chlorine or bromine, $PG^1$ represents an amine protecting group such as Alloc or Boc and m, n, A, B, Y and Q have the same meanings as in formula I.

The compounds of formula II can be obtained by reacting the compounds of formula II-1 with the compounds of formula II-2 (described in WO 2010/041194). This reaction can be performed in the presence of a NaH when Y=N; when Y=CH, it can be performed under conditions described for the metal catalyzed N-arylation of 2-oxazolidinones or amides, in particular by using CuI and 1,1,1-tris(hydroxymethyl)ethane in the presence of $Cs_2CO_3$ (Chen et al., Org. Lett. (2006), 8, 5609), or $Pd(OAc)_2$ and DPEphos in the presence of $K_3PO_4$.

In the particular case wherein Y=N and Q=O, the compounds of formula II can furthermore be prepared as described in Scheme 3 hereafter.

In Scheme 3, Xa represents a halogen such as chlorine or bromine, $PG^1$ represents an amine protecting group such as Alloc or Boc and m, n, A and B have the same meanings as in formula I.

The oxazolidinones of formula II-1 can be reacted (Scheme 3) with the nitropyridine derivatives of formula III-1 (prepared as described in WO 2007/118130) in presence of a base such as $K_2CO_3$, $Pd(OAc)_2$ and DPEphos. The resulting oxazolidinones of formula III-2 can be treated with ammonium chloride and powdered iron followed by removal of the nitrogen protecting group using general reaction technique 2, affording the compounds of formula II wherein Y=N and Q=O.

Compounds of Formula III:

The compounds of formula III wherein $R^{1a}$ represents carboxy and $R^{1b}$ represents H are commercially available or can be prepared by hydrolysis of their corresponding known alkyl esters (e.g. III wherein U=N, $R^2$=cyclopropyl and $R^3$=H: EP 607825) in the presence of conc. aq. HCl. The compounds of formula III wherein each of $R^{1a}$ and $R^{1b}$ represents H can be prepared by decarboxylation under thermal conditions (between 150° C. and 250° C.) of the corresponding compounds of formula III wherein $R^{1a}$ represents carboxyl. The compounds of formula III wherein $R^{1a}$ and $R^{1b}$ represent together either the group *—C(O)—NH—S—# or the group *—C(OH)=N—S—# wherein "*" represents the point of attachment of $R^{1a}$ and "#" represents the point of attachment of $R^{1b}$ can be prepared according to or in analogy to J. Heterocycl. Chem. (1990), 27(5), 1191-1195.

Compounds of Formula IV:

The compounds of formula IV are commercially available or can be prepared as described in EP 235762, DE 2362553, DE 2840910, EP 241206 or *Chemical & Pharmaceutical Bulletin* (1988), 36(3), 1223-8.

Compounds of Formula II-1:

The compounds of formula II-1 can be prepared as described in Scheme 4 hereafter.

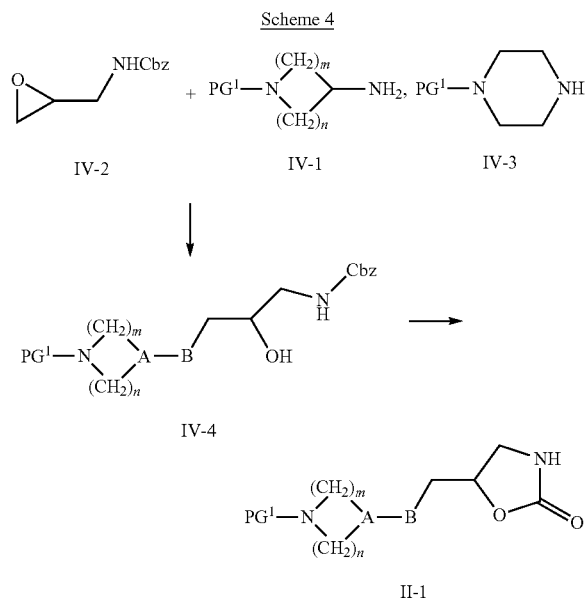

Scheme 4

In Scheme 4, PG$^1$ represents an amine protecting group such as Alloc or Boc and m, n, A and B have the same meanings as in formula I.

The commercially available piperidine derivatives of formula IV-1 or IV-3 can be reacted (Scheme 4) with the commercially available epoxide of formula IV-2 in the presence of MgSO$_4$. The resulting aminoalcohol derivatives of formula IV-4 can be reacted with K$_2$CO$_3$, affording the oxazolidinone derivatives of formula II-1.

General Reaction Techniques:

General Reaction Technique 1 (Alkylation of an Amine with a Mesylate or an Iodide):

The amine derivative is reacted with the required iodide derivatives or alcohol derivatives activated as a sulfonate (OMs, ONf, ONs, OBs, OTf, OTs) in presence of an inorganic base such as K$_2$CO$_3$ or an org. base such as TEA or DIPEA in a solvent such as THF, DMF or DMSO between 0° C. and +80° C. Further details can be found in *Comprehensive Organic Transformations. A guide to Functional Group Preparations;* 2$^{nd}$ Edition, R. C. Larock, Wiley-VC; New York, Chichester, Weinheim, Brisbane, Singapore, Toronto, (1999) Section Amines p. 779.

General Reaction Technique 2 (Removal of Amino Protecting Group):

The Cbz protecting group is removed by hydrogenolysis over a noble metal catalyst (e.g. Pd/C or Pd(OH)$_2$/C). The Boc group is removed under acidic conditions such as HCl in an org. solvent such as MeOH or dioxane, or TFA neat or diluted in a solvent such DCM. The Alloc group is removed in presence of tetrakis(triphenylphosphine) palladium(0) in presence of an allyl cation scavenger such as morpholine, dimedone or tributyltin hydride between 0° C. and 50° C. in a solvent such as THF. Further general methods to remove amine protecting groups have been described in *Protecting Groups in Organic Synthesis,* 3$^{rd}$ Ed (1999), 494-653; T. W. Greene, P. G. M. Wuts; (Publisher: John Wiley and Sons, Inc., New York, N.Y.).

General Reaction Technique 3 (Formation of Azides):

The activated alcohol (activated either as a sulfonate or an iodide derivative) is reacted with sodium azide in presence of an org. base such as DIPEA or TEA or an inorganic base such as Na$_2$CO$_3$ in a solvent such as DMSO or DMF between 20 and 100° C. Alternatively, the azide can also be obtained by activation of the alcohol under Mitsunobu conditions in presence of PPh$_3$ and DEAD or DIAD in a solvent such as THF, DMF, DCM or DME between −20 and +60° C. as reviewed in *Synthesis* (1981), 1-28. Alternatively, the alcohol is directly reacted with DPPA in presence of a base such as TEA or DBU in a solvent such as THF between −20 and +60° C. as described in *J. Org. Chem.* (1993), 58, 5886-5888.

General Reaction Technique 4 (Formation of Phthalimides):

The activated alcohol (activated either as a sulfonate or an iodide derivative) is reacted with potassium phthalimide in a solvent such as DMSO or DMF between 20 and 100° C.

General Reaction Technique 5 (Formation of Amines):

The azides are hydrogenated over a noble metal catalyst such as Pd/C in a solvent such as MeOH or EA. In case the molecule is containing an unsaturated double or triple bond, the reduction can be performed using PPh$_3$ in the presence of water as described in *J. Med. Chem.* (1993), 36, 2558-68. Besides, the phthalimide derivatives are treated between 50 and 120° C. with a hydrazine derivative such as hydrazine hydrate, methylhydrazine or an amine such as N$^1$,N$^1$-dimethylpropane-1,3-diamine in a solvent such as MeOH or EtOH. Further general methods have been described in *Protecting Groups in Organic Synthesis,* 3$^{rd}$ Ed (1999), 564-566; T. W. Greene, P. G. M. Wuts (Publisher: John Wiley and Sons, Inc., New York).

General Reaction Technique 6 (Reductive Amination):

The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or a mixture of solvents such as DCE/MeOH. The reaction can be catalyzed by traces of acid (usually AcOH). The intermediate imine is reduced with a suitable reducing agent (e.g. NaBH$_4$, NaBH$_3$CN, or NaBH(OAc)$_3$ or through hydrogenation over a noble metal catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

Particular embodiments of the invention are described in the following Examples, which serve to illustrate the invention in more detail without limiting its scope in any way.

EXAMPLES

Abbreviations (As Used Herein and in the Description Above):

Ac acetyl
Alloc allyloxycarbonyl
aq. aqueous
Boc tert-butoxycarbonyl
Bs 4-bromobenzenesulfonyl (brosylate)
Bu butyl
Cbz benzyloxycarbonyl
CC column chromatography over silica gel Cipro ciprofloxacin
DAD diode array detection
DBU 1,8-diazabicyclo[5.4.0]undec-7-ene
DCE 1,2-dichloroethane
DCM dichloromethane
DEAD diethyl azodicarboxylate
dil. diluted
DPEphos bis(2-diphenylphosphinophenyl)ether
DIAD diisopropyl azodicarboxylate
DIPEA N,N-diisopropylethylamine
DME 1,2-dimethoxyethane
DMF N,N-dimethylformamide
DMSO dimethylsulfoxide
DPPA diphenyl phosphoryl azide
EA ethyl acetate
ELSD evaporative light scattering detector
ESI electron spray ionisation
eq. equivalent
Et ethyl
Hept heptane
Hex hexane
HPLC high pressure liquid chromatography
LC liquid chromatography
Me methyl
MS mass spectroscopy
Ms methanesulfonyl (mesyl)
Nf nonafluorobutanesulfonyl
Ns 4-nitrobenzenesulfonyl (nosylate)
org. organic
Pd/C palladium on carbon
Pd(OH)$_2$/C palladium dihydroxide on carbon
Ph phenyl
PPh$_3$ triphenylphosphine
Pyr pyridine
rac racemic
rt room temperature
sat. saturated
TBME tert-butylmethylether
tBu tert-butyl
TEA triethylamine
Tf trifluoromethanesulfonyl (triflyl)
TFA trifluoroacetic acid
THF tetrahydrofuran
TLC thin layer chromatography
Ts para-toluenesulfonyl
wt % percent in weight All temperatures are stated in ° C. All temperatures are stated in ° C. Unless otherwise indicated, the reactions take place at rt.

Analytical TLC characterisations were performed with 0.2 mm plates: Merck, Silica gel 60 F$_{254}$. Elution is performed with EA, Hept, DCM, MeOH or mixtures thereof. Detection was done with UV or with a solution of KMnO$_4$ (3 g), K$_2$CO$_3$ (20 g), 5% NaOH (3 mL) and H$_2$O (300 mL) with subsequent heating.

CCs are performed using Brunschwig 60A silica gel (0.032-0.63 mm); elution is performed with EA, Hept, DCM, MeOH or mixtures thereof. In the cases of compounds containing an acid function, 1% of AcOH is added to the eluent(s).

Compounds are characterized by $^1$H-NMR (300 MHz) (Varian Oxford); or by $^1$H-NMR (400 MHz) (Bruker Advance 400). Chemical shifts δ are given in ppm relative to the solvent used; multiplicities: s=singlet, d=doublet, t=triplet, q=quadruplet, p=pentuplet, hex=hexet, hep=heptet, m=multiplet, br.=broad, coupling constants are given in Hz. Alternatively compounds are characterized by LC-MS (Sciex API 2000 with Agilent 1100 Binary Pump with DAD and ELSD or an Agilent quadrupole MS 6140 with Agilent 1200 Binary Pump, DAD and ELSD); by TLC (TLC plates from Merck, Silica gel 60 F$_{254}$); or by melting point. Compounds are purified by chromatography on Silica gel 60A. NH$_4$OH as used for CC is 25% aq.

The LC-MS data have been performed using the following three respective methods:
Method 1 (MS1):
  Pump: Waters Acquity Binary, Solvent Manager; MS: Waters SQ Detector; DAD: Acquity UPLC PDA Detector; ELSD: Acquity UPLC ELSD.
  Column: Acquity UPLC CSH C18 1.7 μm, 2.1×50 mm from Waters, thermostated in the Acquity UPLC Column Manager at 60° C.
  Eluents: A: H$_2$O+0.05% formic acid; B: MeCN+0.045% formic acid. Gradient: 2% B→98% B over 3.0 min. Flow: 0.6 mL/min.
  Detection: UV 214 nm, ELSD and MS; the retention time $t_R$ is given in min.
Method 2 (MS2):
  Thermo MSQ Plus with Dionex GHP 3200 Binary Pump, DAD and ELSD.
  Eluents: A: H$_2$O+0.04% TFA; B: MeCN; Gradient: 2% B→98% B over 3.0 min. Flow: 0.6 mL/min
  Column: ZorbaxSB-Aq, 3.7 μm, 4.6×50 mm/USXA001358
Method 3 (MS3):
  Same method as MS2 but
  Column: Waters Atlantis T3, 5 μm, 4.6×30 mm/01273031412503.

The number of decimals given for the corresponding [M+H+] peak(s) of each tested compound depends upon the accuracy of the LC-MS device actually used.

The HPLCs are done over a stationary phase such as a rapid resolution Zorbax SB C18 (1.8 μm) column, or a rapid resolution Zorbax Eclipse Plus C18 (1.8 μm) column. Typical HPLC conditions are a gradient of eluent A (water:MeCN 95:5 with 0.1% of formic acid, in the presence or absence of 5 mmol/L ammonium formate) and eluent B (MeCN:water 95:5 with 0.1% of formic acid, in the presence or not of 5 mmol/L ammonium formate), at a flow rate of 0.8 to 5 mL/min.

Example 1

1-cyclopropyl-6-fluoro-4-oxo-7-{4-[(R)-2-oxo-3-(3-oxo-3,4-dihydro-2H-benzo[1,4]thiazin-6-yl)-oxazolidin-5-ylmethyl]-piperazin-1-yl}-1,4-dihydro-quinoline-3-carboxylic acid A mixture of 1-cyclopropyl-6-fluoro-1,4-dihydro-7-(1-piperazinyl)-4-oxo-3-quinoline carboxylic acid (commercial; 331 mg), 6-((S)-5-iodomethyl-2-oxooxazolidin-3-yl)-4H-benzo[1,4]thiazin-3-one (prepared according to WO 2008/126034; 395 mg) and DIPEA (0.5 ml) in DMSO (6 ml) was heated at 80° C. for 24 h. The reaction mixture was allowed to reach rt, poured on 0.1N HCl (50 ml) and filtered. The resulting solid was purified by CC (DCM/MeOH 19:1 to 9:1 to 4:1, followed by DCM/MeOH 19:1+1% AcOH), affording after concentration under reduced pressure and subsequent stirring in MeOH/EA a beige solid.
$^1$H NMR (DMSO-d$_6$) δ: 11.40 (s, 1H); 10.55 (s, 1H); 8.68 (s, 1H); 7.95-7.80 (m, 1H); 7.59-7.45 (m, 1H); 7.36-7.25 (m, 2H); 7.15-7.06 (m, 1H); 4.99-4.79 (m, 1H); 4.18-4.01 (m, 1H); 3.81-3.62 (m, 2H); 3.41 (s, 2H); 3.34-3.18 (m, 4H);

2.83-2.62 (m, 6H); 1.37-1.21 (m, 2H); 1.13-0.97 (m, 2H). MS (ESI, m/z): 594.4 [M+H$^+$] for $C_{29}H_{28}N_5O_6FS$; $t_R$=0.65 min (MS2).

Example 2

1-cyclopropyl-6-fluoro-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-[1,8]naphthyridine-3-carboxylic acid A mixture of 7-chloro-1-cyclopropyl-6-fluoro-4-oxo-1,4-dihydro-[1,8]naphthyridine-3-carboxylic acid (commercial; 141 mg), 6-[(5R)-5-[(3-azetidinylamino)methyl]-2-oxo-3-oxazolidinyl]-2H-1,4-benzothiazin-3(4H)-one (prepared according to WO 2008/126034; 167 mg) and TEA (0.15 ml) in MeCN (4 ml) was heated at 75° C. for 2 h. The reaction mixture was allowed to reach rt, diluted with water, filtered and the solid was washed with MeOH and EA, affording a beige solid.

$^1$H NMR (DMSO-d$_6$) δ: 10.54 (s, 1H); 8.54 (s, 1H); 7.94 (d, J=11.5 Hz, 1H); 7.32-7.26 (m, 2H); 7.11 (dd, J=2.3 Hz, J=8.6 Hz, 1H); 4.79-4.62 (m, 1H); 4.59-4.36 (m, 2H); 4.17-3.92 (m, 3H); 3.89-3.70 (m, 2H); 3.70-3.56 (m, 1H); 3.41 (s, 2H); 2.95-2.75 (m, 3H); 1.21-0.98 (m, 4H). MS (ESI, m/z): 582.2 [M+H$^+$] for $C_{27}H_{25}N_6O_6FS$; $t_R$=0.64 min (MS2).

Example 3

1-cyclopropyl-6-fluoro-4-oxo-7-{4-[(R)-2-oxo-3-(3-oxo-3,4-dihydro-2H-pyrido[3,2-b][1,4]thiazin-6-yl)-oxazolidin-5-ylmethyl]-piperazin-1-yl}-1,4-dihydro-quinoline-3-carboxylic acid In analogy to Example 1, starting from 1-cyclopropyl-6-fluoro-1,4-dihydro-7-(1-piperazinyl)-4-oxo-3-quinoline carboxylic acid (commercial; 166 mg) and 6-[(5R)-5-[[(methylsulfonyl)oxy]methyl]-2-oxo-3-oxazolidinyl]-2H-pyrido[3,2-b]-1,4-thiazin-3(4H)-one (prepared in analogy to its (S) enantiomer described in WO 2010/041194; 180 mg), the title compound was obtained as a beige solid after CC (DCM/MeOH 9:1) and crystallization from EtOH.

$^1$H NMR (DMSO-d$_6$) δ: 11.40 (s, 1H), 10.84 (s, 1H); 8.65 (s, 1H); 7.89 (d, J=13.3 Hz, 1H); 7.81-7.74 (m, 1H); 7.70-7.64 (m, 1H), 7.55 (d, J=7.4 Hz, 1H); 4.97-4.81 (m, 1H); 4.26-4.13 (m, 1H); 3.89-3.74 (m, 2H); 3.51 (s, 2H); 3.36-3.22 (m, 4H); 2.82-2.65 (m, 6H); 1.37-1.22 (m, 2H); 1.22-1.11 (m, 2H). MS (ESI, m/z): 595.18 [M+H$^+$] for $C_{28}H_{27}N_6O_6FS$; $t_R$=1.13 min (MS 1).

Example 4

1-cyclopropyl-6-fluoro-4-oxo-7-{4-[(R)-2-oxo-3-(3-oxo-3,4-dihydro-2H-benzo[1,4]thiazin-6-yl)-oxazolidin-5-ylmethyl]-piperazin-1-yl}-1,4-dihydro-[1,8]naphthyridine-3-carboxylic acid 4.1. 4-[(R)-2-oxo-3-(3-oxo-3,4-dihydro-2H-benzo[1,4]thiazin-6-yl)-oxazolidin-5-ylmethyl]-piperazine-1-carboxylic acid tert-butyl ester A solution of 6-((S)-5-iodomethyl-2-oxooxazolidin-3-yl)-4H-benzo[1,4]thiazin-3-one (prepared according to WO 2008/126034; 1.0 g) and Boc-piperazine (1.43 g) in DMF (10 ml) was stirred overnight at rt and 2 h at 60° C. The reaction mixture was allowed to reach rt, diluted with water and extracted with EA (2×). The combined org. layers were washed with water and brine, dried over MgSO$_4$, filtered and evaporated under reduced pressure, affording after stirring the residue in TBME a colourless solid.

$^1$H NMR (CDCl$_3$) δ: 8.15 (s, 1H); 7.41 (d, J=2.3 Hz, 1H); 7.29 (d, J=8.5 Hz, 1H); 6.95 (dd, J=2.3 Hz, J=8.6 Hz, 1H); 4.88-4.67 (m, 1H); 4.05 (t, J=8.7 Hz, 1H); 3.79 (dd, J=7.0 Hz, J=8.8 Hz, 1H); 3.47-3.36 (m, 4H); 3.41 (s, 2H); 2.80-2.67 (m, 2H); 2.64-2.43 (m, 4H); 1.46 (s, 9H). MS (ESI, m/z): 449.1 [M+H$^+$].

4.2. 6-((R)-2-oxo-5-piperazin-1-ylmethyl-oxazolidin-3-yl)-4H-benzo[1,4]thiazin-3-one A solution of intermediate 4.1 (730 mg) in DCM (10 ml) was treated with triethylsilane (0.28 ml) and TFA (3.12 ml). After stirring at rt for 30 min the solution was evaporated under reduced pressure and the residue was taken up in DCM and washed with a dil. NH$_4$OH solution. The aq. layer was extracted with DCM/MeOH (9:1) and the combined org. layers were dried over MgSO$_4$, filtered and evaporated under reduced pressure, affording a colourless foam.

$^1$H NMR (DMSO-d$_6$) δ: 10.52 (s, 1H); 7.35-7.24 (m, 2H); 7.11 (dd, J=2.2 Hz, J=8.6 Hz, 1H); 4.88-4.72 (m, 1H); 4.05 (t, J=8.8 Hz, 1H); 3.68 (dd, J=7.1 Hz, J=8.5 Hz, 1H); 3.42 (s, 2H); 2.72-2.61 (m, 4H); 2.61-2.56 (m, 2H); 2.43-2.31 (m, 4H). MS (ESI, m/z): 349.0 [M+H$^+$] for $C_{16}H_{20}N_4O_3S$.

4.3. 1-cyclopropyl-6-fluoro-4-oxo-7-{4-[(R)-2-oxo-3-(3-oxo-3,4-dihydro-2H-benzo[1,4]thiazin-6-yl)-oxazolidin-5-ylmethyl]-piperazin-1-yl}-1,4-dihydro-[1,8]naphthyridine-3-carboxylic acid In analogy to Example 2, starting from intermediate 4.2 (174 mg) and 7-chloro-1-cyclopropyl-6-fluoro-4-oxo-1,4-dihydro-[1,8]naphthyridine-3-carboxylic acid (commercial; 141 mg), the title compound was obtained as a colourless foam.

$^1$H NMR (DMSO-d$_6$) δ: 11.40 (s, 1H), 10.54 (s, 1H); 8.60 (s, 1H); 8.06 (d, J=13.5 Hz, 1H); 7.33 (d, J=2.2 Hz, 1H); 7.30 (d, J=8.6 Hz, 1H); 7.11 (dd, J=2.3 Hz, J=8.7 Hz, 1H); 4.95-4.78 (m, 1H); 4.14-4.02 (m, 1H); 3.92-3.80 (m, 4H); 3.78-3.62 (m, 2H); 3.42 (s, 2H); 2.79-2.60 (m, 6H); 1.25-1.11 (m, 2H); 1.11-1.02 (m, 2H). MS (ESI, m/z): 595.18 [M+H$^+$] for $C_{28}H_{27}N_6O_6FS$ $t_R$=1.12 min (MS1).

Example 5

6-((R)-5-{[1-(8-cyclopropyl-3-fluoro-5-oxo-5,8-dihydro-[1,8]naphthyridin-2-yl)-azetidin-3-ylamino]-methyl}-2-oxo-oxazolidin-3-yl)-4H-benzo[1,4]thiazin-3-one 5.1. 7-chloro-1-cyclopropyl-6-fluoro-1H-[1,8]naphthyridin-4-one 7-chloro-1-cyclopropyl-6-fluoro-4-oxo-1,4-dihydro-[1,8]naphthyridine-3-carboxylic acid (2.0 g) was added portionwise to a boiling solution of Dowtherm (50 ml heated at 250° C.) and further stirred at this temperature for 1 h. The reaction mixture was allowed to reach rt and diluted with 1N NaOH (100 ml) and extracted with EA. The org. phase was discarded. The aq. phase was acidified with 3N HCl and extracted with ether/EA. The aq. layer was filtered and the filtrate was extracted with ether/EA. The combined org. layers were washed with water and brine dried over MgSO$_4$, filtered and evaporated under reduced pressure affording a solid which was stirred in Hept/EA and filtered. The filtrate was concentrated under reduced pressure and purified by CC (EA to EA/MeOH 9:1), affording a beige solid.

$^1$H NMR (CDCl$_3$) δ: 8.36 (d, J=7.5 Hz, 1H); 7.73 (d, J=8.0 Hz, 1H); 6.25 (d, J=8.0 Hz, 1H); 3.62-3.51 (m, 1H); 1.33-1.20 (m, 2H); 1.03-0.93 (m, 2H).

MS (ESI, m/z): 239.16 [M+H$^+$] for C$_{11}$H$_8$N$_2$OClF; t$_R$=0.67 min (MS3).

5.2. 6-((R)-5-{[1-(8-cyclopropyl-3-fluoro-5-oxo-5,8-dihydro-[1,8]naphthyridin-2-yl)-azetidin-3-ylamino]-methyl}-2-oxo-oxazolidin-3-yl)-4H-benzo[1,4]thiazin-3-one In analogy to Example 2, starting from intermediate 5.1 (30 mg) and 6-[(5R)-5-[(3-azetidinylamino)methyl]-2-oxo-3-oxazolidinyl]-2H-1,4-benzothiazin-3(4H)-one (prepared according to WO 2008/126034; 42 mg), the title compound was obtained as a beige solid.

$^1$H NMR (DMSO-d$_6$) δ: 10.54 (s, 1H); 7.77 (d, J=3.9 Hz, 1H); 7.74 (d, J=7.8 Hz, 1H); 7.36-7.25 (m, 3H); 7.14-7.07 (m, 1H); 4.76-4.63 (m, 1H); 4.44-4.30 (m, 1H); 4.09-3.89 (m, 3H); 3.85-3.69 (m, 2H); 3.47-3.42 (m, 1H); 3.41 (s, 2H); 2.90-2.76 (m, 4H); 1.07-0.85 (m, 4H). MS (ESI, m/z): 537.17 [M+H$^+$] for C$_{26}$H$_{25}$N$_6$O$_4$FS; t$_R$=0.95 min (MS1).

Example 6

1-cyclopropyl-6-fluoro-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid In analogy to Example 2, starting from 7-chloro-1-cyclopropyl-6-fluoro-4-oxo-1,4-dihydro-[1,8]naphthyridine-3-carboxylic acid (70 mg) and 6-[(5R)-5-[(3-azetidinylamino)methyl]-2-oxo-3-oxazolidinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H); 11.16 (s, 1H); 8.54 (s, 1H); 7.94 (d, J=11.5 Hz, 1H); 7.59 (d, J=8.7 Hz, 1H); 7.40 (d, J=8.7 Hz, 1H); 4.78-4.62 (m, 1H); 4.59 (s, 2H); 4.54-4.38 (m, 2H); 4.21-3.95 (m, 3H); 3.91-3.74 (m, 2H); 3.71-3.56 (m, 1H); 2.91-2.81 (m, 2H); 1.21-0.99 (m, 4H). MS (ESI, m/z): 566.18 [M+H$^+$] for C$_{26}$H$_{24}$N$_7$O$_7$F; t$_R$=1.00 min (MS1).

Example 7

1-cyclopropyl-8-methoxy-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-quinoline-3-carboxylic acid The title compound was prepared in analogy to Example 2, starting from 1-cyclopropyl-7-fluoro-1,4-dihydro-8-methoxy-4-oxo-3-quinolinecarboxylic acid anhydride with boric acid (1:1) and with acetic acid (1:2) (101 mg; prepared according to WO 2010/056633) and 6-[(5R)-5-[(3-azetidinylamino)-methyl]-2-oxo-3-oxazolidinyl]-2H-1,4-benzothiazin-3(4H)-one (prepared according to WO 2008/126034; 167 mg). At the end of the reaction, the reaction mixture was concentrated under reduced pressure and the residue was taken up in MeOH and treated with 1N HCl in MeOH (3 ml) for 15 min. The reaction mixture was diluted with water (2 ml) and the solid was filtered off. The org. phase was concentrated under reduced pressure and purified by CC (DCM/MeOH 9:1 followed by DCM/MeOH 9:1+1% AcOH), affording after evaporation and stirring of the residue with MeOH/TBME a beige solid.

$^1$H NMR (DMSO-d$_6$) δ: 11.40 (s, 1H), 10.56 (s, 1H); 8.59 (s, 1H); 7.99-7.83 (m, 1H); 7.33 (d, J=2.3 Hz, 1H); 7.29 (d, J=8.6 Hz, 1H); 7.10 (dd, J=2.3 Hz, J=8.6 Hz, 1H); 6.84-6.68 (m, 1H); 4.78-4.61 (m, 1H); 4.33-4.18 (m, 2H); 4.11-3.98 (m, 2H); 3.83-3.67 (m, 4H); 3.55 (s, 3H); 3.41 (s, 2H); 2.85 (d, J=5.2 Hz, 2H); 1.80 (br. s, 1H); 1.13-0.99 (m, 2H); 0.99-0.86 (m, 2H). MS (ESI, m/z): 592.19 [M+H$^+$] for C$_{29}$H$_{29}$N$_5$O$_7$S; t$_R$=1.01 min (MS1).

Example 8

1-cyclopropyl-8-methoxy-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-quinoline-3-carboxylic acid In analogy to Example 2, starting from 1-cyclopropyl-7-fluoro-1,4-dihydro-8-methoxy-4-oxo-3-quinolinecarboxylic acid anhydride with boric acid (1:1) and with acetic acid (1:2) (101 mg; prepared according to WO 2010/056633) and 6-[(5R)-5-[(3-azetidinylamino)methyl]-2-oxo-3-oxazolidinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H), 11.16 (s, 1H); 8.61 (s, 1H); 7.98-7.86 (m, 1H); 7.62-7.55 (m, 1H); 7.41 (d, J=8.7 Hz, 1H); 6.86-6.69 (m, 1H); 4.78-4.63 (m, 1H); 4.59 (s, 2H); 4.34-4.18 (m, 2H); 4.18-4.03 (m, 2H); 3.91-3.80 (m, 1H); 3.80-3.65 (m, 3H); 3.55 (s, 3H); 2.85 (d, J=4.9 Hz, 2H); 1.86 (s, 1H); 1.15-1.01 (m, 2H); 1.01-0.90 (m, 2H). MS (ESI, m/z): 577.21 [M+H$^+$] for C$_{28}$H$_{28}$N$_6$O$_8$; t$_R$=0.94 min (MS1).

Example 9

1-ethyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid In analogy to Example 2, starting from 7-chloro-1-ethyl-1,4-dihydro-4-oxo-1,8-naphthyridine-3-carboxylic acid (prepared according to U.S. Pat. No. 3,149,104; 63 mg) and 6-[(5R)-5-[(3-azetidinylamino)methyl]-2-oxo-3-oxazolidinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H); 11.22 (s, 1H); 8.93 (s, 1H), 8.31 (d, J=8.9 Hz, 1H); 7.62-7.56 (m, 1H); 7.46-7.39 (m, 1H); 6.75 (d, J=8.9 Hz, 1H); 4.60 (s, 2H); 4.53-4.36 (m, 4H); 4.32-4.15 (m, 4H); 3.83 (dd, J=6.9 Hz, J=10.5 Hz, 1H); 3.48-3.24 (m, 4H); 1.38 (t, J=7.0 Hz, 3H). MS (ESI, m/z): 536.19 [M+H$^+$] for C$_{25}$H$_{25}$N$_7$O$_7$; t$_R$=0.92 min (MS1).

Example 10

1-cyclopropyl-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-[1,8]naphthyridine-3-carboxylic acid

10.1. 7-chloro-1-cyclopropyl-4-oxo-1,4-dihydro-[1,8]naphthyridine-3-carboxylic acid A suspension of 7-chloro-1-cyclopropyl-1,4-dihydro-4-oxo-1,8-naphthyridine-3-carboxylic acid ethyl ester (prepared according to EP 607825; 500 mg) in 6N HCl (6 ml) was stirred at 100° C. for 30 min. The reaction mixture was allowed to reach rt and the resulting crystals were collected by filtration and sequentially washed with water and MeOH, affording a beige solid.

$^1$H NMR (DMSO-d$_6$) δ: 11.40 (s, 1H), 8.81 (s, 1H); 8.70 (d, J=8.4 Hz, 1H); 7.78 (d, J=8.4 Hz, 1H); 3.85-3.74 (m, 1H); 1.27-1.07 (m, 4H). MS (ESI, m/z): 265.1 [M+H$^+$] for C$_{12}$H$_9$N$_2$O$_3$Cl; t$_R$=0.7 min (MS3).

10.2. 1-cyclopropyl-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-[1,8]naphthyridine-3-carboxylic acid In analogy to Example 2, starting from intermediate 10.1 (66 mg) and 6-[(5R)-5-[(3-azetidinylamino)methyl]-2-oxo-3-oxazolidinyl]-2H-1,4-benzothiazin-3(4H)-one (prepared according to WO 2008/126034; 84 mg), the title compound was obtained as a beige solid.

$^1$H NMR (DMSO-d$_6$) δ: 11.40 (s, 1H), 10.54 (s, 1H); 8.53 (s, 1H); 8.22 (d, J=8.9 Hz, 1H); 7.33 (d, J=2.3 Hz, 1H); 7.32-7.26 (m, 1H); 7.10 (dd, J=2.3 Hz, J=8.5 Hz, 1H); 6.65 (d, J=8.9 Hz, 1H); 4.77-4.63 (m, 1H); 4.37-4.27 (m, 2H); 4.05 (t, J=8.7 Hz, 1H); 3.93-3.72 (m, 4H); 3.70-3.58 (m, 1H); 3.42 (s, 2H); 2.91-2.80 (m, 2H); 1.18-0.93 (m, 4H).

MS (ESI, m/z): 563.17 [M+H$^+$] for C$_{27}$H$_{26}$N$_6$O$_6$S; t$_R$=1.01 min (MS1).

Example 11

1-methyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid In analogy to Example 2, starting from 7-chloro-1,4-dihydro-1-methyl-4-oxo-1,8-naphthyridine-3-carboxylic acid (60 mg; prepared according to JP 01165584) and 6-[(5R)-5-[(3-azetidinylamino)methyl]-2-oxo-3-oxazolidinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H), 11.23 (s, 1H); 8.92 (s, 1H); 8.32 (d, J=8.9 Hz, 1H); 7.62-7.56 (m, 1H); 7.44 (d, J=8.8 Hz, 1H); 6.76 (d, J=8.9 Hz, 1H); 5.09-5.97 (m, 1H); 4.61 (s, 2H); 4.52-4.39 (m, 1H); 4.38-4.21 (m, 4H); 3.91 (s, 3H); 3.88-3.78 (m, 1H); 3.55-3.33 (m, 4H). MS (ESI, m/z): 522.16 [M+H$^+$] for C$_{24}$H$_{23}$N$_7$O$_7$; t$_R$=0.47 min (MS3).

Example 12

6-fluoro-1-methyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid In analogy to Example 2, starting from 7-chloro-6-fluoro-1,4-dihydro-1-methyl-4-oxo-1,8-naphthyridine-3-carboxylic acid (64 mg; prepared according to WO 2011/037433) and 6-[(5R)-5-[(3-azetidinylamino)methyl]-2-oxo-3-oxazolidinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H), 11.16 (s, 1H); 8.87 (s, 1H); 7.93 (d, J=11.5 Hz, 1H); 7.62-7.55 (m, 1H); 7.40 (d, J=8.7 Hz, 1H); 4.78-4.61 (m, 1H); 4.58 (s, 2H); 4.55-4.34 (m, 2H); 4.19-3.92 (m, 3H); 3.87 (s, 3H); 3.86-3.74 (m, 2H); 2.93-2.77 (m, 2H).

MS (ESI, m/z): 540.16 [M+H$^+$] for C$_{24}$H$_{22}$N$_7$O$_7$F; t$_R$=0.91 min (MS1).

Example 13

1-benzyl-6-fluoro-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid In analogy to Example 2, starting from 1-benzyl-7-chloro-6-fluoro-4-oxo-1,4-dihydro-[1,8]naphthyridine-3-carboxylic acid (83 mg; commercially available or prepared by hydrolysis of the corresponding ester obtained according to CN 101792443 in the presence of 6M HCl) and 6-[(5R)-5-[(3-azetidinylamino)methyl]-2-oxo-3-oxazolidinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H), 11.16 (s, 1H); 8.87 (s, 1H); 7.93=11.5 Hz, 1H); 7.63-7.56 (m, 1H); 7.40 (d, J=8.7 Hz, 1H); 7.41-7.20 (m, 5H); 5.62 (s, 2H); 4.78-4.61 (m, 1H); 4.59 (s, 2H); 4.55-4.31 (m, 2H); 4.20-4.08 (m, 1H); 4.07-3.91 (m, 2H); 3.90-3.70 (m, 2H); 2.91-2.76 (m, 2H). MS (ESI, m/z): 616.20 [M+H$^+$] for C$_{30}$H$_{26}$N$_7$O$_7$F; t$_R$=1.19 min (MS1).

Example 14

1-cyclopropyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid In analogy to Example 2, starting from intermediate 10.1 (66 mg) and 6-[(5R)-5-[(3-azetidinylamino)methyl]-2-oxo-3-oxazolidinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H), 11.15 (s, 1H); 8.53 (s, 1H); 8.21 (d, J=8.9 Hz, 1H); 7.62-7.55 (m, 1H); 7.40 (d, J=8.7 Hz, 1H); 6.64 (d, J=8.9 Hz, 1H); 4.78-4.62 (m, 1H); 4.59 (s, 2H); 4.37-4.25 (m, 2H); 4.20-4.07 (m, 1H); 3.93-3.72 (m, 4H); 3.71-3.58 (m, 1H); 2.91-2.81 (m, 2H); 1.21-1.08 (m, 2H); 1.08-0.97 (m, 2H).

MS (ESI, m/z): 548.19 [M+H$^+$] for C$_{26}$H$_{25}$N$_7$O$_7$F; t$_R$=0.93 min (MS1).

Example 15

6-fluoro-1-(2-hydroxy-ethyl)-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid 15.1. (Z)-Ethyl 2-(2,6-dichloro-5-fluoronicotinoyl)-3-((2-hydroxyethyl)amino)acrylate A solution of 2,6-dichloro-α-(ethoxymethylene)-5-fluoro-β-oxo-3-pyridinepropanoic acid ethyl ester (1.00 g; prepared according to EP 132845) was treated with ethanolamine (0.18 mL). After a few minutes, the reaction mixture became sticky and was diluted with Hept/ether (1:1; 10 mL). After further stirring at rt for 1.5 h, the solvents were evaporated under reduced pressure and the crude yellow oil was directly used in the next step.

$^1$H NMR (DMSO-d$_6$) δ: 8.22 (s, 1H); 8.02 (d, J=7.9 Hz, 1H); 3.90 (q, J=7.1 Hz, 2H); 3.61-3.45 (m, 4H); 3.34 (t, J=5.7 Hz, 1H); 0.94 (t, J=7.1 Hz, 3H). MS (ESI, m/z): 350.94 [M+H$^+$] (MS3).

15.2. Ethyl 7-chloro-6-fluoro-1-(2-hydroxyethyl)-4-oxo-1,4-dihydro-1,8-naphthyridine-3-carboxylate A solution of intermediate 15.1 (1.04 g) in THF (15 mL) was treated at 0° C. with LiHMDS (3.11 ml). The reaction mixture was further stirred at rt for 1 h, filtered and the solid was washed with THF. The resulting solid was purified by CC (DCM/MeOH 9:1 to 4:1), affording a yellow solid.

$^1$H NMR (DMSO-d$_6$) δ: 8.73 (s, 1H); 8.45 (d, J=7.9 Hz, 1H); 4.98-4.90 (m, 1H); 4.44 (t, J=5.1 Hz, 2H); 4.23 (q, J=7.1 Hz, 2H); 3.78-3.67 (m, 2H); 1.27 (t, J=7.1 Hz, 3H).

MS (ESI, m/z): 314.94 [M+H$^+$] (MS3).

15.3. 7-chloro-6-fluoro-1-(2-hydroxy-ethyl)-4-oxo-1,4-dihydro-[1,8]naphthyridine-3-carboxylic acid A suspension of intermediate 15.2 (330 mg) in 6M HCl (40 ml) was stirred at 100° C. for 1 h. The reaction mixture was allowed to reach rt and the resulting solid was collected by filtration, affording a beige solid.

$^1$H NMR (DMSO-d$_6$) δ: 11.40 (s, 1H); 9.05 (s, 1H); 8.70 (d, J=7.7 Hz, 1H); 4.66-4.55 (m, 2H); 3.76 (t, J=5.2 Hz, 2H). MS (ESI, m/z): 286.91 [M+H$^+$] (MS3).

15.4. 6-fluoro-1-(2-hydroxy-ethyl)-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid In analogy to Example 2, starting from intermediate 15.3 (72 mg) and 6-[(5R)-5-[(3-azetidinylamino)methyl]-2-oxo-3-oxazodinyl]-2H-1,4-benzoxazin-3(4H)-one (prepared according to WO 2008/126034; 89 mg), the title compound was obtained as a beige solid.

$^1$H NMR (DMSO-d$_6$) δ: 11.40 (s, 1H), 11.15 (s, 1H); 8.72 (s, 1H); 7.96 (d, J=11.6 Hz, 1H); 7.63-7.53 (m, 1H); 7.40 (d, J=8.7 Hz, 1H); 4.97-4.83 (m, 1H); 4.78-4.61 (m, 1H); 4.59 (s, 2H); 4.54-4.29 (m, 4H); 4.20-3.90 (m, 3H); 3.89-3.65 (m, 4H); 2.93-2.73 (m, 2H).

MS (ESI, m/z): 570.18 [M+H$^+$] for C$_{25}$H$_{24}$N$_7$O$_8$F; t$_R$=0.87 min (MS1).

Example 16

1-cyclopropyl-6-fluoro-4-oxo-7-{4-[(S)-2-oxo-3-(3-oxo-3,4-dihydro-2H-benzo[1,4]thiazin-6-yl)-oxazolidin-5-ylmethyl]-piperazin-1-yl}-1,4-dihydro-[1,8]naphthyridine-3-carboxylic acid The title compound was obtained as a beige solid in analogy to Example 4 but using 6-((R)-5-iodomethyl-2-oxooxazolidin-3-yl)-4H-benzo[1,4]thiazin-3-one (prepared according to WO 2008/126034) in the first step. Compared to Example 4, for the intermediate and the final compound the yields of preparation were in the same range and identical spectroscopic data (MS, NMR) were collected.

Example 17

1-cyclopropyl-6-fluoro-4-oxo-7-(4-{[(R)-2-oxo-3-(3-oxo-3,4-dihydro-2H-pyrido[3,2-b][1,4]oxazin-6-yl)-oxazolidin-5-ylmethyl]-amino}-piperidin-1-yl)-1,4-dihydro-[1,8]naphthyridine-3-carboxylic acid 17.1. (4-((R)-3-benzyloxycarbonylamino-2-hydroxy-propylamino)-piperidine-1-carboxylic acid tert-butyl ester A solution of [(2S)-oxiranylmethyl]-carbamic acid benzyl ester (15.6 g; prepared according to WO 2004/002973) and 4-(N-Boc-amino)piperidine (15.1 g) in MeOH (100 mL) was treated with MgSO$_4$ (12.3 g) and the white suspension was stirred at rt for 6 h. The mixture was evaporated, suspended in DCM and partionated between water (1 l) and DCM (1 l). The layers were separated and the aq. layer was reextracted with DCM. The combined org. layers were evaporated and purified by CC (EE to EE/MeOH 9:1), affording a yellow oil.

MS (ESI, m/z): 408.12 [M+H$^+$] for C$_{21}$H$_{33}$N$_3$O$_5$; t$_R$=0.66 min (MS2).

17.2. 4-[((R)-2-oxo-oxazolidin-S-ylmethyl)-amino]-piperidine-1-carboxylic acid tert-butyl ester A solution of intermediate 17.1 (3.2 g) in MeOH (36 ml) was treated with K$_2$CO$_3$ (1.24 g) and stirred at 60° C. for 3.5 h. The reaction mixture was concentrated in vacuo and the residue was taken up in EA/water. The aq. layer was extracted 2× with EA. The combined org. layers were washed with brine, dried over MgSO$_4$, filtered, evaporated and purified by CC (EA/MeOH 9:1), affording a yellow oil.

MS (ESI, m/z): 300.06 [M+H$^+$] for C$_{14}$H$_{25}$N$_3$O$_4$; t$_R$=0.49 min (MS2).

17.3. 4-{[(R)-3-(5-ethoxycarbonylmethoxy-6-nitro-pyridin-2-yl)-2-oxo-oxazolidin-5-ylmethyl]-amino}-piperidine-1-carboxylic acid tert-butyl ester A 50 ml flask was charged with ethyl (6-bromo-2-nitropyridin-3-yloxy)acetate (1.1 g; prepared as described in WO 2007/118130), intermediate 17.2 (1.2 g) and diluted in dioxane (18 ml). Pd(OAc)$_2$ (41.2 mg), DPEphos (198 mg) and powdered K$_2$CO$_3$ (621 mg) were added and the suspension was degassed with argon. The mixture was heated in a sealed flask at 85° C. for 2 h. The reaction mixture was cooled to rt and partitioned between EA and water. The org. layer was washed with brine, dried over MgSO$_4$, concentrated under reduced pressure and purified by CC (EA to EA/MeOH 9:1), affording an off-white foam.

MS (ESI, m/z): 524.14 [M+H$^+$] for C$_{23}$H$_{33}$N$_5$O$_9$; t$_R$=0.72 min (MS2).

17.4. 4-{[(R)-2-oxo-3-(3-oxo-3,4-dihydro-2H-pyrido[1,4]oxazin-6-yl)-oxazolidin-5-ylmethyl]-amino}-piperidine-1-carboxylic acid tert-butyl ester Iron powder (720 mg) was added to a solution of ammonium chloride (1.15 g) in H$_2$O/MeOH (1:1; 18 ml). The suspension was heated to 40° C. and treated dropwise with a solution of intermediate 17.3 (1.5 g) in MeOH (28.7 ml). The reaction was further stirred at 70° C. for 5 h. The reaction mixture was filtered over a pad of Celite and washed with MeOH. The filtrate was acidified with AcOH (9 ml) and the yellow solution was stirred overnight at 85° C. The solvent was concentrated under reduced pressure and the suspension was triturated with H₂O, cooled to 0° C. and filtrated. The filter cake was then washed with water and ether, affording an off-white solid.

MS (ESI, m/z): 448.04 [M+H⁺] for $C_{21}H_{29}N_5O_6$; $t_R$=0.61 min (MS2).

17.5. 6-[(R)-2-oxo-5-(piperidin-4-ylaminomethyl)-oxazolidin-3-yl]-4H-pyrido[3,2-b][1,4]oxazin-3-one hydrochloride A suspension of intermediate 17.4 (900 mg) in dioxane/MeOH (1:1; 20 ml) was treated at rt with 4M HCl in dioxane (5.2 ml) and further stirred for 6 h. The reaction mixture was diluted with ether and the beige crystals were collected by filtration, washed with ether and MeOH, affording off-white crystals.

MS (ESI, m/z): 348.07 [M+H⁺] for $C_{15}H_{22}N_5O_4$; $t_R$=0.38 min (MS2).

17.6. 1-cyclopropyl-6-fluoro-4-oxo-7-(4-{[(R)-2-oxo-3-(3-oxo-3,4-dihydro-2H-pyrido[3,2-b][1,4]oxazin-6-yl)-oxazolidin-5-ylmethyl]-amino}-piperidin-1-yl)-1,4-dihydro-[1,8]naphthyridine-3-carboxylic acid In analogy to Example 2, starting from intermediate 17.5 (166 mg) and 7-chloro-1-cyclopropyl-6-fluoro-4-oxo-1,4-dihydro-[1,8]naphthyridine-3-carboxylic acid (commercial; 100 mg), the title compound was obtained as an off-white solid.

¹H NMR (DMSO-d₆) δ: 11.17 (s, 1H), 8.59 (s, 1H), 8.04 (d, J=13.6 Hz, 1H), 7.58 (d, J=8.7 Hz, 1H), 7.40 (d, J=8.7 Hz, 1H), 4.27 (br., 1H), 4.59 (s, 2H), 4.42 (m, 2H), 4.14 (m, 1H), 3.85 (m, 1H), 3.68 (m, 1H), 3.28 (m, 2H), 2.93 (m, 3H), 2.00 (m, 3H), 1.40 (m, 2H), 1.12 (m, 4H). MS (ESI, m/z): 594.09 [M+H⁺] for $C_{28}H_{28}N_7O_7F$; $t_R$=0.64 min (MS2).

Example 18

1-cyclopropyl-6-fluoro-4-oxo-7-{4-[(R)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1,8]naphthyridine-3-carboxylic acid

18.1. 4-((S)-3-benzyloxycarbonylamino-2-hydroxypropyl)-piperazine-1-carboxylic acid tert-butyl ester The compound was prepared in analogy to Example 17, step 17.1, starting from 1-Boc-piperazine (20.41 g) and [(2S)-oxiranylmethyl]-carbamic acid benzyl ester (22.75 g). A yellowish oil (16.0 g; 37% yield) was obtained.

MS (ESI, m/z): 394.12 [M+H⁺] for $C_{20}H_{31}N_3O_5$; $t_R$=0.67 min (MS2).

18.2. 4-((S)-2-oxo-oxazolidin-5-ylmethyl)-piperazine-1-carboxylic acid tert-butyl ester The compound was prepared in analogy to Example 17, step 17.2, starting from intermediate 18.1 (16.0 g). A colourless solid (5.11 g; 44% yield) was obtained.

MS (ESI, m/z): 259.22 [M-CO] for $C_{13}H_{23}N_3O_4$; $t_R$=0.68 min (MS2).

18.3. 4-[(R)-3-(5-ethoxycarbonylmethoxy-6-nitropyridin-2-yl)-2-oxo-oxazolidin-5-ylmethyl]-piperazine-1-carboxylic acid tert-butyl ester The compound was prepared in analogy to Example 17, step 17.3, starting from intermediate 18.2 (6.44 g) and ethyl (6-bromo-2-nitropyridin-3-yloxy)acetate (6.22 g; prepared as described in WO 2007/118130). A beige foam (9.71 g; 93.5% yield) was obtained.

MS (ESI, m/z): 510.15 [M+H⁺] for $C_{22}H_{31}N_5O_9$; $t_R$=0.70 min (MS2).

18.4. 4-[(R)-2-oxo-3-(3-oxo-3,4-dihydro-2H-pyrido[3,2-b][1,4]oxazin-6-yl)-oxazolidin-5-ylmethyl]-piperazine-1-carboxylic acid tert-butyl ester The compound was prepared in analogy to Example 17, step 17.4, starting from intermediate 18.3 (9.71 g). A beige solid (6.27 g; 75.9% yield) was obtained.

MS (ESI, m/z): 434.03 [M+H⁺] for $C_{20}H_{27}N_5O_6$; $t_R$=0.59 min (MS2).

18.5. 6-((R)-2-oxo-S-piperazin-1-ylmethyl-oxazolidin-3-yl)-4H-pyrido[3,2-b][1,4]oxazin-3-one The compound was prepared in analogy to Example 17, step 17.5, starting from intermediate 18.4 (579 mg). A yellow solid (130 mg; 29% yield) was obtained.

MS (ESI, m/z): 334.04 [M+H⁺] for $C_{15}H_{19}N_5O_4$; $t_R$=0.45 min (MS2).

18.6. 1-cyclopropyl-6-fluoro-4-oxo-7-{4-[(R)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1,8]naphthyridine-3-carboxylic acid In analogy to Example 2, starting from intermediate 18.5 (117 mg) and 7-chloro-1-cyclopropyl-6-fluoro-4-oxo-1,4-dihydro-[1,8]naphthyridine-3-carboxylic acid (commercial; 90 mg), the title compound was obtained as an off-white solid (80 mg; 43.3% yield).

¹H NMR (DMSO-d₆) δ: 11.17 (s, 1H), 8.59 (s, 1H), 8.06 (d, J=13.8 Hz, 1H), 7.59 (d, J=8.8 Hz, 1H), 7.41 (d, J=8.8 Hz, 1H), 4.87 (m, 1H), 4.59 (s, 2H), 4.20 (m, 1H), 3.82 (m, 5H), 3.69 (m, 1H), 2.70 (m, 6H), 1.13 (m, 4H). MS (ESI, m/z): 580.07 [M+H⁺] for $C_{27}H_{26}N_7O_7F$; $t_R$=0.62 min (MS2).

Example 19

1-cyclopropyl-6-fluoro-4-oxo-7-{4-[(S)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1,8]naphthyridine-3-carboxylic acid

19.1. 6-*(S)-2-oxo-5-piperazin-1-ylmethyl-oxazolidin-3-yl)-4H-pyrido[3,2-b][1,4]oxazin-3-one The compound was prepared in analogy to steps 18.1 to 18.5 of Example 18, starting from [(2R)-oxiranylmethyl]-carbamic acid benzyl ester. The respective yields for the 5 steps were the following: 59% (yellowish oil; epoxide opening), 28% (colourless solid; oxazolidinone formation), 23% (brown oil; arylation), 59% (beige solid; oxazinone formation) and 99% (beige solid; HCl treatment).

MS (ESI, m/z): 334.04 [M+H⁺] for $C_{15}H_{19}N_5O_4$; $t_R$=0.45 min (MS2).

19.2. 1-cyclopropyl-6-fluoro-4-oxo-7-{4-[(S)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1, 8]naphthyridine-3-carboxylic acid In analogy to Example 18, step 18.6, starting from intermediate 19.1 (101 mg) and 7-chloro-1-cyclopropyl-6-fluoro- 4-oxo-1,4-dihydro-[1,8]naphthyridine-3-carboxylic acid (commercial; 77 mg), the title compound was obtained as a beige solid (130 mg; 82% yield).

$^1$H NMR (DMSO-d$_6$) δ: 11.17 (s, 1H); 8.59 (s, 1H); 8.06 (d, J=13.8 Hz, 1H); 7.59 (d, J=8.8 Hz, 1H); 7.41 (d, J=8.8 Hz, 1H); 4.87 (m, 1H); 4.59 (s, 2H); 4.20 (m, 1H); 3.82 (m, 5H); 3.69 (m, 1H); 2.70 (m, 6H); 1.13 (m, 4H). MS (ESI, m/z): 580.07 [M+H$^+$] for C$_{27}$H$_{26}$N$_7$O$_7$F; t$_R$=0.62 min (MS2).

Example 20

1-cyclopropyl-6-fluoro-4-oxo-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-1,4-dihydro-[1,8]naphthyridine-3-carboxylic acid 20.1. 6-[(S)-2-oxo-5-(piperidin-4-ylaminomethyl)-oxazolidin-3-yl]-4H-pyrido[3,2-b][1,4]oxazin-3-one dihydrochloride The compound was prepared in analogy to steps 17.1. to 17.5 of Example 17, starting from [(2S)-oxiranylmethyl]-carbamic acid benzyl ester. The respective yields for the 5 steps were the following: 71% (colourless oil; epoxide opening), 96% (yellowish oil; carbamate formation), 93% (yellow foam; arylation), 81% (beige solid; cyclisation) and 81% (yellow foam; HCl treatment).

MS (ESI, m/z): 348.27 [M+H$^+$] for C$_{15}$H$_{19}$N$_5$O$_4$; t$_R$=0.61 min (MS2).

20.2. 1-cyclopropyl-6-fluoro-4-oxo-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-1,4-dihydro-[1,8]naphthyridine-3-carboxylic acid In analogy to Example 17, step 17.6, starting from intermediate 20.1 (1.76 g) and 7-chloro-1-cyclopropyl-6-fluoro-4-oxo-1,4-dihydro-[1,8]naphthyridine-3-carboxylic acid (commercial; 1.13 g), the title compound was obtained as a beige solid (1.05 g; 44% yield).

$^1$H NMR (DMSO-d$_6$) δ: 11.17 (s, 1H), 8.59 (s, 1H), 8.04 (d, J=13.6 Hz, 1H), 7.58 (d, J=8.7 Hz, 1H), 7.40 (d, J=8.7 Hz, 1H), 4.27 (br., 1H), 4.59 (s, 2H), 4.42 (m, 2H), 4.14 (m, 1H), 3.85 (m, 1H), 3.68 (m, 1H), 3.28 (m, 2H), 2.93 (m, 3H), 2.00 (m, 3H), 1.40 (m, 2H), 1.12 (m, 4H). MS (ESI, m/z): 594.09 [M+H$^+$] for C$_{28}$H$_{28}$N$_7$O$_7$F; t$_R$=0.63 min (MS2).

Example 21

1-cyclopropyl-6-fluoro-4-oxo-7-((RS)-3-{[(S)-2-oxo-3-(3-oxo-3,4-dihydro-2H-pyrido[3,2-b][1,4]oxazin-6-yl)-oxazolidin-5-ylmethyl]-amino}-pyrrolidin-1-yl)-1,4-dihydro-[1,8]naphthyridine-3-carboxylic acid 21.1. (RS)-3-((S)-3-benzyloxycarbonylamino-2-hydroxy-propylamino)-pyrrolidine-1-carboxylic acid tert-butyl ester The title compound was prepared in analogy to Example 17, step 17.1, starting from [(2R)-oxiranylmethyl]-carbamic acid benzyl ester (8.23 g; prepared according to WO 2004/002973) and rac-3-amino-1-Boc-pyrrolidine (7.40 g; commercial) in MeCN (300 mL), affording a colourless oil (10.7 g; 68% yield).

MS (ESI, m/z): 394.19 [M+H$^+$] for C$_{20}$H$_{31}$N$_3$O$_5$; t$_R$=0.64 min (MS2).

21.2. (RS)-3-[((S)-2-oxo-oxazolidin-5-ylmethyl)-amino]-pyrrolidine-1-carboxylic acid tert-butyl ester A solution of intermediate 21.1 (10.7 g) in THF (175 mL) was treated at 0° C. with KOtBu (3.05 g) and further stirred at rt for 1 h. The reaction mixture was concentrated in vacuo and the residue was taken up in EA/water. The aq. layer was extracted twice with EA. The combined org. layers were washed with brine, dried over MgSO$_4$, filtered, evaporated and purified by CC (EA/MeOH 19:1 to 9:1+1% NH$_4$OH), affording a colourless glass (6.90 g; 89% yield).

MS (ESI, m/z): 331.20 [M+H$^+$] for C$_{13}$H$_{23}$N$_3$O$_4$; t$_R$=0.50 min (MS2).

21.3. (RS)-3-{[(S)-3-(5-ethoxycarbonylmethoxy-6-nitro-pyridin-2-yl)-2-oxo-oxazolidin-5-ylmethyl]-amino}-pyrrolidine-1-carboxylic acid tert-butyl ester The title compound was prepared in analogy to Example 17, step 17.1, starting from ethyl (6-bromo-2-nitropyridin-3-yloxy)acetate (6.84 g; prepared as described in WO 2007/118130) and intermediate 21.2 (6.4 g), affording a yellowish foam (11.34 g; 99% yield).

MS (ESI, m/z): 454.08 [M+H$^+$] for C$_{22}$H$_{31}$N$_5$O$_9$; t$_R$=0.70 min (MS2).

21.4. (RS)-3-{[(S)-2-oxo-3-(3-oxo-3,4-dihydro-2H-pyrido[3,2-b][1,4]oxazin-6-yl)-oxazolidin-5-ylmethyl]-amino}-pyrrolidine-1-carboxylic acid tert-butyl ester In analogy to Example 17, step 17.4, the title compound was prepared from intermediate 21.3 (11.34 g), affording a yellowish foam (7.13 g; 74% yield).

MS (ESI, m/z): 434.16 [M+H$^+$] for C$_{20}$H$_{27}$N$_5$O$_6$; t$_R$=0.57 min (MS2).

21.5. 6-((S)-2-oxo-5-(((RS)-pyrrolidin-3-ylamino)methyl)oxazolidin-3-yl)-2H-pyrido[3,2-b][1,4]oxazin-3(4H)-one dihydrochloride In analogy to Example 17, step 17.5, the title compound was prepared from intermediate 21.4 (7.0 g), affording a yellowish solid (6.7 g, 100% yield).

MS (ESI, m/z): 334.22 [M+H$^+$] for C$_{15}$H$_{21}$N$_5$O$_4$Cl$_2$; t$_R$=0.40 min (MS2).

21.6. 1-cyclopropyl-6-fluoro-4-oxo-7-((RS)-3-{[(S)-2-oxo-3-(3-oxo-3,4-dihydro-2H-pyrido[3,2-b][1,4]oxazin-6-yl)-oxazolidin-5-ylmethyl]-amino}-pyrrolidin-1-yl)-1,4-dihydro-[1,8]naphthyridine-3-carboxylic acid In analogy to Example 2, starting from intermediate 21.5 (406 mg) and 7-chloro-1-cyclopropyl-6-fluoro-4-oxo-1,4-dihydro-[1,8]naphthyridine-3-carboxyl ic acid (commercial; 283 mg), the title compound was obtained as a beige solid (mixture of diastereomers; 398 mg; 68% yield).

MS (ESI, m/z): 580.07 [M+H$^+$] for C$_{27}$H$_{26}$N$_7$O$_7$F; t$_R$=0.62 min (MS2).

Example 22

1-cyclopropyl-6-fluoro-4-oxo-7-[(S)-3-({[(S)-2-oxo-3-(3-oxo-3,4-dihydro-2H-pyrido[3,2-b][1,4]oxazin-6-yl)-oxazolidin-5-ylmethyl]-amino}-methyl)-pyrrolidin-1-yl]-1,4-dihydro-[1,8]naphthyridine-3-carboxylic acid

22.1. (S)-3-[((S)-3-benzyloxycarbonylamino-2-hydroxy-propylamino)-methyl]-pyrrolidine-1-carboxylic acid tert-butyl ester The title compound was prepared in analogy to Example 17, step 17.1, starting from [(2R)-oxiranylmethyl]-carbamic acid benzyl ester (5.17 g; prepared according to WO 2004/002973) and (S)-3-aminoethylpyrrolidine-1-carboxylic acid tert-butyl ester (5.00 g; commercial) in MeCN (120 mL), affording a colourless oil (6.4 g; 63% yield).
MS (ESI, m/z): 408.21 [M+H$^+$] for $C_{21}H_{33}N_3O_5$; $t_R$=0.66 min (MS2).

22.2. (S)-3-{[((S)-2-oxo-oxazolidin-5-ylmethyl)-amino]-methyl}-pyrrolidine-1-carboxylic acid tert-butyl ester A solution of intermediate 22.1 (6.4 g) in THF (100 mL) was treated at 0° C. with KOtBu (1.76 g) and further stirred at rt for 1 h. The reaction mixture was concentrated in vacuo and the residue was taken up in EA/water. The aq. layer was extracted twice with EA. The combined org. layers were washed with brine, dried over MgSO$_4$, filtered, evaporated and purified by CC (EA/MeOH 19:1 to 9:1+1% NH$_4$OH), affording a colourless oil (4.34 g; 92% yield).
MS (ESI, m/z): 300.17 [M+H$^+$] for $C_{14}H_{25}N_3O_4$; $t_R$=0.50 min (MS2).

22.3. (S)-3-({[(S)-3-(5-ethoxycarbonylmethoxy-6-nitro-pyridin-2-yl)-2-oxo-oxazolidin-5-ylmethyl]-amino}-methyl)-pyrrolidine-1-carboxylic acid tert-butyl ester The title compound was prepared in analogy to Example 17, step 17.3, starting from ethyl (6-bromo-2-nitropyridin-3-yloxy)acetate (4.01 g; prepared according to WO 2007/118130) and intermediate 22.2 (3.94 g), affording a yellowish foam (7.01 g; 100% yield).
MS (ESI, m/z): 524.22 [M+H$^+$] for $C_{23}H_{33}N_5O_9$; $t_R$=0.71 min (MS2).

22.4. (S)-3-({[(S)-2-oxo-3-(3-oxo-3,4-dihydro-2H-pyrido[3,2-b][1,4]oxazin-6-yl)-oxazolidin-5-ylmethyl]-amino}-methyl)-pyrrolidine-1-carboxylic acid tert-butyl ester In analogy to Example 17, step 17.4, the title compound was prepared from intermediate 22.3 (7.01 g), affording a yellowish foam (4.1 g; 68% yield).
MS (ESI, m/z): 448.18 [M+H$^+$] for $C_{21}H_{29}N_5O_6$; $t_R$=0.61 min (MS2).

22.5. 6-((S)-2-oxo-5-{[((R)-1-pyrrolidin-3-ylmethyl)-amino]-methyl}-oxazolidin-3-yl)-4H-pyrido[3,2-b][1,4]oxazin-3-one dihydrochloride In analogy to Example 17, step 17.5, the title compound was prepared from intermediate 22.4 (4.0 g), affording a colourless solid (3.87 g; 100% yield).
MS (ESI, m/z): 348.26 [M+H$^+$] for $C_{16}H_{23}N_5O_4Cl_2$; $t_R$=0.40 min (MS2).

22.6. 1-cyclopropyl-6-fluoro-4-oxo-7-[(S)-3-({[(S)-2-oxo-3-(3-oxo-3,4-dihydro-2H-pyrido[3,2-b][1,4]oxazin-6-yl)-oxazolidin-5-ylmethyl]-amino}-methyl)-pyrrolidin-1-yl]-1,4-dihydro-[1,8]naphthyridine-3-carboxylic acid In analogy to Example 2, starting from intermediate 22.5 (420 mg) and 7-chloro-1-cyclopropyl-6-fluoro-4-oxo-1,4-dihydro-[1,8]naphthyridine-3-carboxylic acid (commercial; 283 mg), the title compound was obtained as a beige solid (440 mg; 74% yield).
$^1$H NMR (DMSO-d$_6$) δ: 11.15 (s, 1H), 8.52 (s, 1H), 7.91 (d, J=12.7 Hz, 1H), 7.57 (d, J=8.7 Hz, 1H), 7.39 (d, J=8.7 Hz, 1H), 4.77 (br., 1H), 4.59 (s, 2H), 4.14 (m, 1H), 3.77 (m, 6H), 2.95 (m, 2H), 2.94 (m, 2H), 2.73 (m, 2H), 2.05 (s, 1H), 1.85 (m, 1H), 1.09 (m, 4H). MS (ESI, m/z): 594.06 [M+H$^+$] for $C_{28}H_{28}N_7O_7F$; $t_R$=0.64 min (MS2).

Example 23

9-cyclopropyl-6-fluoro-3-hydroxy-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-9H-1-thia-2,8,9-triaza-cyclopenta[b]naphthalen-4-one In analogy to Example 2, starting from intermediate 20.1 (151 mg) and 7-chloro-9-cyclopropyl-6-fluoro-isothiazolo[5,4-b][1,8]naphthyridine-3,4(2H,9H)-dione (93 mg; prepared according to Chu et al., *J. Heterocycl. Chem.* (1990), 27(5), 1191-1195), the title compound was obtained as a beige solid (110 mg; 59% yield).
$^1$H NMR (DMSO-d$_6$) δ: 11.16 (s, 1H), 7.89 (d, J=12.7 Hz, 1H), 7.58 (d, J=8.7 Hz, 1H), 7.40 (d, J=8.7 Hz, 1H), 4.68 (m, 1H), 4.58 (s, 2H), 4.33 (m, 2H), 4.11 (m, 1H), 3.86 (m, 1H), 3.27 (m, 5H), 2.88 (d, J=5.2 Hz, 2H), 2.76 (m, 1H), 1.95 (m, 2H), 1.36 (m, 2H), 1.17 (m, 4H). MS (ESI, m/z): 622.98 [M+H$^+$] for $C_{28}H_{27}N_8O_6FS$; $t_R$=0.61 min (MS2).

Example 24

9-cyclopropyl-6-fluoro-3-hydroxy-7-(3-{[(S)-2-oxo-3-(3-oxo-3,4-dihydro-2H-pyrido[3,2-b][1,4]oxazin-6-yl)-oxazolidin-5-ylmethyl]-amino}-azetidin-1-yl)-9H-1-thia-2,8,9-triaza-cyclopenta[b]naphthalen-4-one In analogy to Example 2, starting from 6-[(5S)-5-[(3-azetidinylamino)methyl]-2-oxo-3-oxazolidinyl]-2H-1,4-benzoxazin-3(4H)-one (prepared in analogy to WO 2008/126034; 128 mg) and 7-chloro-9-cyclopropyl-6-fluoro-isothiazolo[5,4-b][1,8]naphthyridine-3,4(2H,9H)-dione (93 mg; prepared according to Chu et al., *J. Heterocycl. Chem.* (1990), 27(5), 1191-1195), the title compound was obtained as a beige solid (100 mg; 56% yield).
$^1$H NMR (DMSO-d$_6$) δ: 7.83 (d, J=11.7 Hz, 1H), 7.59 (d, J=8.6 Hz, 1H), 7.40 (d, J=8.6 Hz, 1H), 4.71 (m, 1H), 4.59 (s, 2H), 4.41 (m, 2H), 4.14 (m, 1H), 4.01 (m, 2H), 3.84 (m, 2H), 3.32 (m, 8H), 2.87 (m, 2H), 1.16 (m, 4H). MS (ESI, m/z): 594.88 [M+H$^+$] for $C_{26}H_{23}N_8O_6FS$; $t_R$=0.58 min (MS2).

Example 25

9-cyclopropyl-6-fluoro-3-hydroxy-7-{4-[(S)-2-oxo-3-(3-oxo-3,4-dihydro-2H-pyrido[3,2-b][1,4]oxazin-6-yl)-oxazolidin-5-ylmethyl]-piperazin-1-yl}-9H-1-thia-2,8,9-triaza-cyclopenta[b]naphthalen-4-one In analogy to Example 2, starting from 6-((S)-2-oxo-5-piperazin-1-ylmethyl-oxazolidin-3-yl)-4H-pyrido[3,2-b][1,4]oxazin-3-one (intermediate 19.1; 133 mg) and 7-chloro-9-cyclopropyl-6-fluoro-isothiazolo[5,4-b][1,8]naphthyridine-3,4(2H,9H)-dione (93 mg; prepared according to Chu et al., *J. Heterocycl. Chem.* (1990), 27(5), 1191-1195), the title compound was obtained as a beige solid (90 mg; 49% yield).

$^1$H NMR (DMSO-d$_6$) δ: 11.23 (s, 1H), 8.03 (d, J=13.2 Hz, 1H), 7.57 (m, 1H), 7.43 (m, 1H), 4.61 (s, 2H), 4.55 (m, 2H), 4.29 (m, 1H), 3.54 (m, 10H), 1.21 (m, 4H).

MS (ESI, m/z): 608.97 [M+H$^+$] for C$_{27}$H$_{25}$N$_8$O$_6$FS; t$_R$=0.59 min (MS2).

Pharmacological Properties of the Invention Compounds
In vitro Assays
Bacterial Growth Minimal Inhibitory Concentrations:
Experimental Methods:

Minimal inhibitory concentrations (MICs; mg/l) were determined in cation-adjusted Mueller-Hinton Broth by a microdilution method following the description given in "Methods for Dilution Antimicrobial Susceptibility Tests for Bacteria that Grow Aerobically", Approved standard, 7$^{th}$ ed., Clinical and Laboratory Standards Institute (CLSI) Document M7-A7, Wayne, Pa., USA, 2006.

All Example compounds were tested against several Gram positive and Gram negative bacteria. Typical antibacterial test results are given in the table hereafter (MIC in mg/l). *Staphylococcus aureus* A798 and *Acinetobacter baumanii* T6474 are multiply-resistant strains, in particular quinolone resistant.

| Example No. | MIC for S. aureus A798 | MIC for A. baumanii T6474 |
|---|---|---|
| 1 | ≤0.016 | 0.125 |
| 2 | ≤0.016 | 0.125 |
| 3 | ≤0.016 | 0.063 |
| 4 | ≤0.016 | 0.125 |
| 5 | ≤0.016 | 1 |
| 6 | ≤0.016 | 0.031 |
| 7 | 0.063 | 0.25 |
| 8 | 0.063 | 0.25 |
| 9 | 0.063 | 0.06 |
| 10 | 0.063 | 0.25 |
| 11 | 0.063 | 0.063 |
| 12 | ≤0.016 | ≤0.016 |
| 13 | ≤0.016 | 1 |
| 14 | 0.031 | 0.06 |
| 15 | 0.25 | 4 |
| 16 | ≤0.016 | 0.125 |
| 17 | ≤0.016 | ≤0.016 |
| 18 | 0.031 | 0.25 |
| 19 | ≤0.016 | 0.063 |
| 20 | ≤0.016 | ≤0.016 |
| 21 | 0.125 | 0.25 |
| 22 | 0.125 | 0.031 |
| 23 | ≤0.016 | ≤0.016 |
| 24 | ≤0.016 | 0.063 |
| 25 | ≤0.016 | 0.125 |
| Cipro | >32 | >32 |

The invention claimed is:

1. A compound of formula I

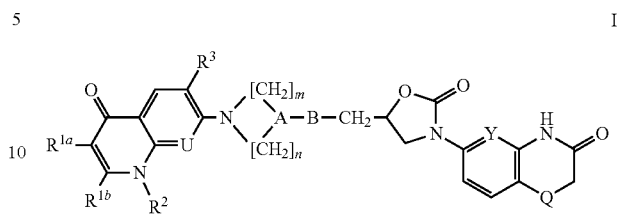

wherein
R$^{1a}$ represents H or carboxy and R$^{1b}$ represents H, or R$^{1a}$ and R$^{1b}$ represent together either the group *—C(O)—NH—S—# or the group *—C(OH)=N—S—# wherein "*" represents the point of attachment of R$^{1a}$ and "#" represents the point of attachment of R$^{1b}$;
R$^2$ represents H, (C$_1$-C$_3$)alkyl, hydroxy-(C$_1$-C$_3$)alkyl, benzyl or (C$_3$-C$_5$)cycloalkyl;
R$^3$ represents H or halogen;
U represents N or CR$^4$; wherein R$^4$ is H or (C$_1$-C$_3$)alkoxy;
A represents CH, B represents NH, m represents 1 or 2 and n represents 1 or 2; or A represents N, B is absent, m represents 2 and n represents 2;
Y represents CH or N; and
Q represents O or S;
or a salt of such a compound.

2. The compound according to claim 1, wherein:
R$^{1a}$ represents H or carboxy;
R$^{1b}$ represents H; and
A represents CH, B represents NH and m represents 1 and n represents 1 or m represents 2 and n represents 2; or A represents N, B is absent, m represents 2 and n represents 2;
or a salt of such a compound.

3. The compound according to claim 1, wherein R$^1$ represents carboxy;
or a salt of such a compound.

4. The compound according to claim 1, wherein R$^2$ represents (C$_1$-C$_3$)alkyl or (C$_3$-C$_5$)cycloalkyl;
or a salt of such a compound.

5. The compound according to claim 4, wherein R$^2$ represents cyclopropyl;
or a salt of such a compound.

6. The compound according to one claim 1, wherein R$^3$ represents halogen;
or a salt of such a compound.

7. The compound according to claim 1, wherein U represents N;
or a salt of such a compound.

8. The compound according to claim 1, wherein U represents CR$^4$, wherein R$^4$ is H or (C1-C3)alkoxy;
or a salt of such a compound.

9. The compound according to claim 1, wherein the group is selected from

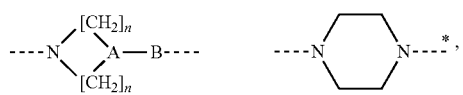

-continued

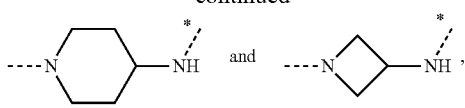

wherein the asterisks denote the bond linking said group to the CH$_2$ group which is attached to the oxazolidinone moiety;
or a salt of such a compound.

10. The compound according to claim 1, wherein Y represents CH or N and Q represents O, or Y represents CH and Q represents S;
or a salt of such a compound.

11. The compound according to claim 1, wherein:
R$_{1a}$ represents carboxy and R$^{1b}$ represents H, or R$^{1a}$ and R$^{1b}$ represent together either the group *—C(O)—NH—S—$^{\#}$ or the group *—C(OH)=N—S—$^{\#}$ wherein "*" represents the point of attachment of R$^{1a}$ and "$^{\#}$" represents the point of attachment of R$^{1b}$;
R$^2$ represents cyclopropyl;
R$^3$ represents fluorine;
U represents N;
A represents CH, B represents NH, m represents 1 or 2 and n represents 1 or 2;
Y represents N; and
Q represents O;
or a salt of such a compound.

12. The compound according to claim 1, wherein the compound is:
1-cyclopropyl-6-fluoro-4-oxo-7-{4-[(R)-2-oxo-3-(3-oxo-3,4-dihydro-2H-benzo[1,4]thiazin-6-yl)-oxazolidin-5-ylmethyl]-piperazin-1-yl}1-1,4-dihydro-quinoline-3-carboxylic acid;
1-cyclopropyl-6-fluoro-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-[1,8]naphthyridine-3-carboxylic acid;
1-cyclopropyl-6-fluoro-4-oxo-7-{4-[(R)-2-oxo-3-(3-oxo-3,4-dihydro-2H-pyrido[3,2-b][1,4]thiazin-6-yl)-oxazolidin-5-ylmethyl]-piperazin-1-yl}-1,4-dihydro-quinoline-3-carboxylic acid;
1-cyclopropyl-6-fluoro-4-oxo-7-{4-[(R)-2-oxo-3-(3-oxo-3,4-dihydro-2H-benzo[1,4]thiazin-6-yl)-oxazolidin-5-ylmethyl]-piperazin-1-yl}-1,4-dihydro-[1,8]naphthyridine-3-carboxylic acid;
6-((R)-5-{[1-(8-cyclopropyl-3-fluoro-5-oxo-5,8-dihydro-[1,8]naphthyridin-2-yl)-azetidin-3-ylamino]-methyl}-2-oxo-oxazolidin-3-yl)-4H-benzo[1,4]thiazin-3-one;
1-cyclopropyl-6-fluoro-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;
1-cyclopropyl-8-methoxy-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-quinoline-3-carboxylic acid;
1-cyclopropyl-8-methoxy-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-quinoline-3-carboxylic acid;
1-ethyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;
1-cyclopropyl-4-oxo-7-(3-{[(R)-2-oxo-3-(3-oxo-3,4-dihydro-2H-benzo[1,4]thiazin-6-yl)-oxazolidin-5-ylmethyl]-amino}-azetidin-1-yl)-1,4-dihydro-[1,8]naphthyridine-3-carboxylic acid;
1-methyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;
6-fluoro-1-methyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;
1-benzyl-6-fluoro-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro[1,8]naphthyridine-3-carboxylic acid;
1-cyclopropyl-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;
6-fluoro-1-(2-hydroxy-ethyl)-4-oxo-7-(3-{[(R)-2-oxo-3-(3-oxo-3,4-dihydro-2H-pyrido[3,2-b][1,4]oxazin-6-yl)-oxazolidin-5-ylmethyl]-amino}-azetidin-1-yl)-1,4-dihydro-[1,8]naphthyridine-3-carboxylic acid;
1-cyclopropyl-6-fluoro-4-oxo-7-{4-[(S)-2-oxo-3-(3-oxo-3,4-dihydro-2H-benzo[1,4]thiazin-6-yl)-oxazolidin-5-ylmethyl]-piperazin-1-yl}-1,4-dihydro-[1,8]naphthyridine-3-carboxylic acid;
1-cyclopropyl-6-fluoro-4-oxo-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-1,4-dihydro[1,8]naphthyridine-3-carboxylic acid;
1-cyclopropyl-6-fluoro-4-oxo-7-{4-[(R)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1,8]naphthyridine-3-carboxylic acid;
1-cyclopropyl-6-fluoro-4-oxo-7-{4-[(S)-2-oxo-3-(3-oxo-3,4-dihydro-2H-pyrido[3,2-b][1,4]oxazin-6-yl)-oxazolidin-5-ylmethyl]-piperazin-1-yl}-1,4-dihydro-[1,8]naphthyridine-3-carboxylic acid;
1-cyclopropyl-6-fluoro-4-oxo-7-(4-{[(S)-2-oxo-3-(3-oxo-3,4-dihydro-2H-pyrido[3,2-b][1,4]oxazin-6-yl)-oxazolidin-5-ylmethyl]amino}-piperidin-1-yl)-1,4-dihydro-[1,8]naphthyridine-3-carboxylic acid;
1-cyclopropyl-6-fluoro-4-oxo-7-(3-{[(S)-2-oxo-3-(3-oxo-3,4-dihydro-2H-pyrido[3,2-b][1,4]oxazin-6-yl)-oxazolidin-5-ylmethyl]-amino}-pyrrolidin-1-yl)-1,4-dihydro-[1,8]naphthyridine-3-carboxylic acid;
1-cyclopropyl-6-fluoro-4-oxo-7-[(S)-3-({[(S)-2-oxo-3-(3-oxo-3,4-dihydro-2H-pyrido[3,2-b][1,4]oxazin-6-yl)-oxazolidin-5-ylmethyl]-amino}-methyl)-pyrrolidin-1-yl]-1,4-dihydro-[1,8]naphthyridine-3-carboxylic acid;
9-cyclopropyl-6-fluoro-3-hydroxy-7-(4-{[(S)-2-oxo-3-(3-oxo-3,4-dihydro-2H-pyrido[3,2-b][1,4]oxazin-6-yl)-oxazolidin-5-ylmethyl]-amino}-piperidin-1-yl)-9H-1-thia-2,8,9-triaza-cyclopenta[b]naphthalen-4-one;
9-cyclopropyl-6-fluoro-3-hydroxy-7-(3-{[(S)-2-oxo-3-(3-oxo-3,4-dihydro-2H-pyrido[3,2-b][1,4]oxazin-6-yl)-oxazolidin-5-ylmethyl]-amino}-azetidin-1-yl)-9H-1-thia-2,8,9-triaza-cyclopenta[b]naphthalen-4-one; or
9-cyclopropyl-6-fluoro-3-hydroxy-7-{4-[(S)-2-oxo-3-(3-oxo-3,4-dihydro-2H-pyrido[3,2-b][1,4]oxazin-6-yl)-oxazolidin-5-ylmethyl]-piperazin-1-yl}-9H-1-thia-2,8,9-triaza-cyclopenta[b]naphthalen-4-one;
or a salt of such a compound.

13. A medicament comprising the compound according to claim 1, or a pharmaceutically acceptable salt thereof.

14. A pharmaceutical composition comprising, as active principle, the compound according to claim 1, or a pharmaceutically acceptable salt thereof, and at least one therapeutically inert excipient.

15. A method of treating a bacterial infection comprising administering an effective amount of a compound or a salt thereof according to claim 1 to a subject in need thereof.

16. A method of treating a bacterial infection comprising administering an effective amount of the pharmaceutical composition according to claim 14 to a subject in need thereof.

* * * * *